US012653412B2

(12) United States Patent
Yu et al.

(10) Patent No.: US 12,653,412 B2
(45) Date of Patent: Jun. 16, 2026

(54) SYSTEM AND METHOD FOR NON-INVASIVE DETERMINATION OF INTRACRANIAL PRESSURE

(71) Applicant: LIONS EYE INSTITUTE LIMITED, Nedlands (AU)

(72) Inventors: Dao-Yi Yu, Nedlands (AU); William Huxley Morgan, Nedlands (AU); Anmar Abdul-Rahman, Nedlands (AU)

(73) Assignee: Lions Eye Institute Limited, Nedlands (AU)

( * ) Notice: Subject to any disclaimer, the term of this patent is extended or adjusted under 35 U.S.C. 154(b) by 0 days.

(21) Appl. No.: 18/550,369

(22) PCT Filed: Mar. 17, 2022

(86) PCT No.: PCT/AU2022/050238
§ 371 (c)(1),
(2) Date: Sep. 13, 2023

(87) PCT Pub. No.: WO2022/192959
PCT Pub. Date: Sep. 22, 2022

(65) Prior Publication Data
US 2024/0164653 A1 May 23, 2024

(30) Foreign Application Priority Data

| Mar. 18, 2021 | (AU) | ................................. | 2021900788 |
| Oct. 22, 2021 | (AU) | ................................. | 2021903392 |

(51) Int. Cl.
*A61B 5/03* (2006.01)
*A61B 3/00* (2006.01)
(Continued)

(52) U.S. Cl.
CPC ............ *A61B 5/031* (2013.01); *A61B 3/0025* (2013.01); *A61B 3/1241* (2013.01); *A61B 3/14* (2013.01);
(Continued)

(58) Field of Classification Search
CPC ..... A61B 5/031; A61B 3/0025; A61B 3/1241; A61B 3/14; A61B 5/0053; A61B 5/7221;
(Continued)

(56) References Cited

U.S. PATENT DOCUMENTS

| 2004/0230124 A1 | 11/2004 | Querfurth |
| 2006/0206037 A1 | 9/2006 | Braxton |
| 2013/0144185 A1 | 6/2013 | Fuller et al. |
| 2016/0128587 A1 | 5/2016 | Kuenen et al. |
| 2017/0065193 A1* | 3/2017 | Yu ............................ A61B 3/12 |
| 2017/0188860 A1 | 7/2017 | Fuller et al. |

OTHER PUBLICATIONS

Matthew Schwartz (Lecture 5: Fourier series, Harvard, 2016). (Year: 2016).*

(Continued)

*Primary Examiner* — Alexei Bykhovski
(74) *Attorney, Agent, or Firm* — Clark Hill PLC

(57) ABSTRACT
A method, system, and computer product for determining intracranial pressure (ICP) of a subject non-invasively. The method including: applying at least one selected controlled force to an eye of the subject; imaging retinal vascular pulsation of the eye of the subject over at least one cardiac cycle at the at least one selected controlled force; processing the retinal vascular pulsation images to produce retinal vascular pulsation amplitude data as a time-varying signal; decomposing the time-varying signal into at least two frequency components representing the time-varying signal; determining intracranial pressure from a data basis which includes at least information associated with the frequency components, and wherein the retinal vascular pulsation data includes at least retinal arterial pulsation data.

22 Claims, 27 Drawing Sheets

(51) Int. Cl.
| | |
|---|---|
| *A61B 3/12* | (2006.01) |
| *A61B 3/14* | (2006.01) |
| *A61B 5/00* | (2006.01) |

(52) U.S. Cl.
CPC .......... *A61B 5/0053* (2013.01); *A61B 5/7221* (2013.01); *A61B 5/7257* (2013.01); *A61B 5/7267* (2013.01); *A61B 5/7278* (2013.01)

(58) Field of Classification Search
CPC ... A61B 5/7257; A61B 5/7267; A61B 5/7278; A61B 5/022; A61B 5/02416; A61B 5/14551; A61B 5/7275; A61B 3/125; A61B 5/0205; A61B 5/0261; A61B 5/0295; A61B 5/315; A61B 5/6821; A61B 5/7285; A61B 3/16; A61B 5/02216; G06N 5/01; G06N 20/00; G16H 50/20
See application file for complete search history.

(56) References Cited

OTHER PUBLICATIONS

Golzan, S. et al., (Non-invasive Cerebrospinal Fluid Pressure Estimation Using Multi-Layer Perceptron Neural Networks, Engineering in Medicine and Biology Society (EMBC), 2013 34th Annual international Conference of ihe IEEE, Aug. 28, 2012, [EEE pp. 5278-5281. (Year: 2012).*

International Search Report dated Jun. 8, 2022 (5 pages) from PCT Priority Application PCT/AU02022/050238 filed Mar. 17, 2022.

Written Opinion dated Jun. 27, 2022 (6 pages) from PCT Priority Application PCT/AU02022/050238 filed Mar. 17, 2022.

Golzan, S. et al., *"Non-Invasive Cerebrospinal Fluid Pressure Estimation Using Multi-Layer Perception Neural Networks"*, Engineering in Medicine and Biology Society (EMBC), 2013 34th Annual International Conference of the IEEE, Aug. 28, 2012, IEEE, pp. 5278-5281. NPL Reference No. XP032464128 Publication Date: Aug. 28, 2012 DOI: https://dx.doi.org/10.1109/EMBC.2012.6347185.

Journal Article, Golzan, S. et al. *"Non-invasive Estimation of Cerebrospinal Fluid Pressure Waveforms by Means of Retinal Venous Pulsatility and Central Aortic Blood Pressure"*, Annals of Biomedical Engineering, 2012, vol. 40, No. 9, pp. 1940-1948. NPL Reference No. XP035096910 Publication Date: Apr. 13, 2012 DOI: https://dx.doi.org/10.1007/s10439-012-0563-y ISSN 1573-9686.

Article, McHugh, J. et al. *"Spontaneous Venous Pulsations Detected with Infrared Videography,"* Journal of Neuro-Opthalmology, 2020, vol. 40(2), pp. 174-177. NPL Reference No. XP055971094 Publication Date: Jun. 1, 2020 DOI: https://dx.doi.org/10.1097/WNO.0000000000000815 ISSN 1070-8022.

Office Action received in counterpart Japanese Patent Appln No. 2023-557313, issued on Feb. 17, 2026 (14 pages total, including machine translation).

* cited by examiner

Violin plots of
harmonic regression
wave form amplitude (HRWa)

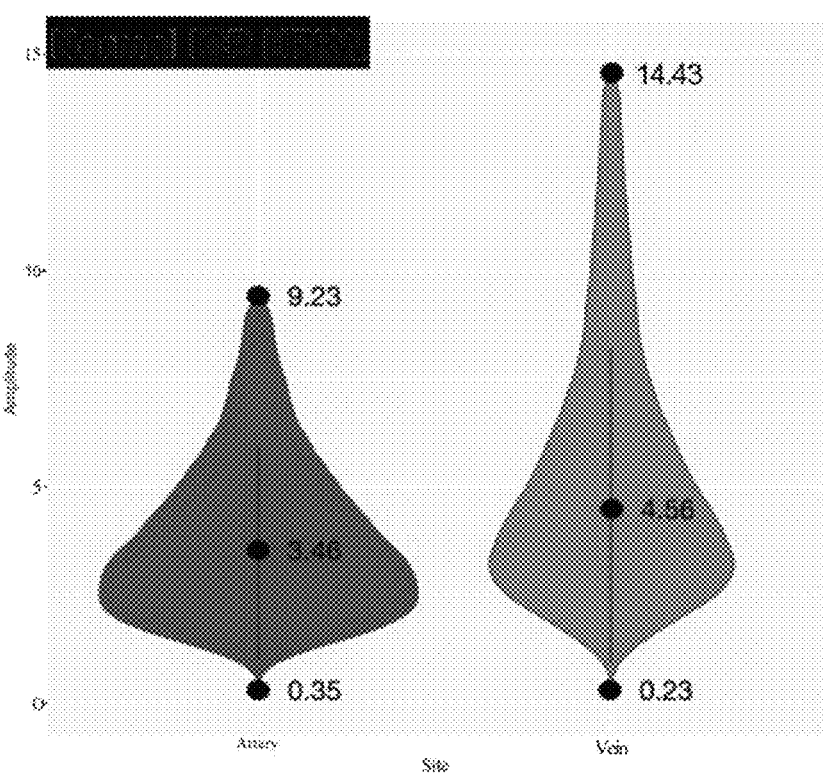
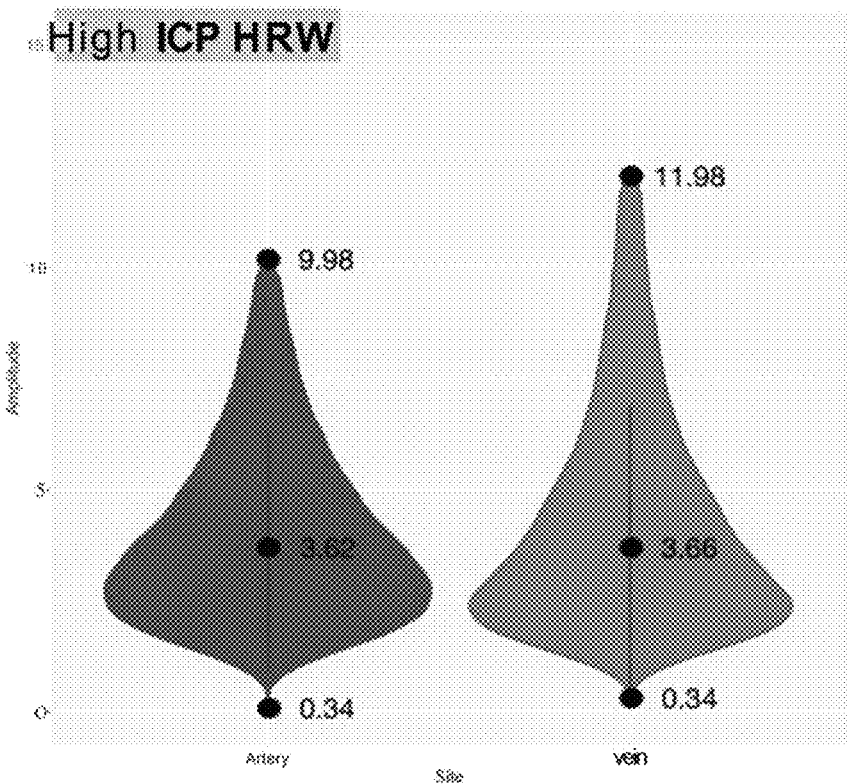
Fig. 21

<u>Fig. 24</u>

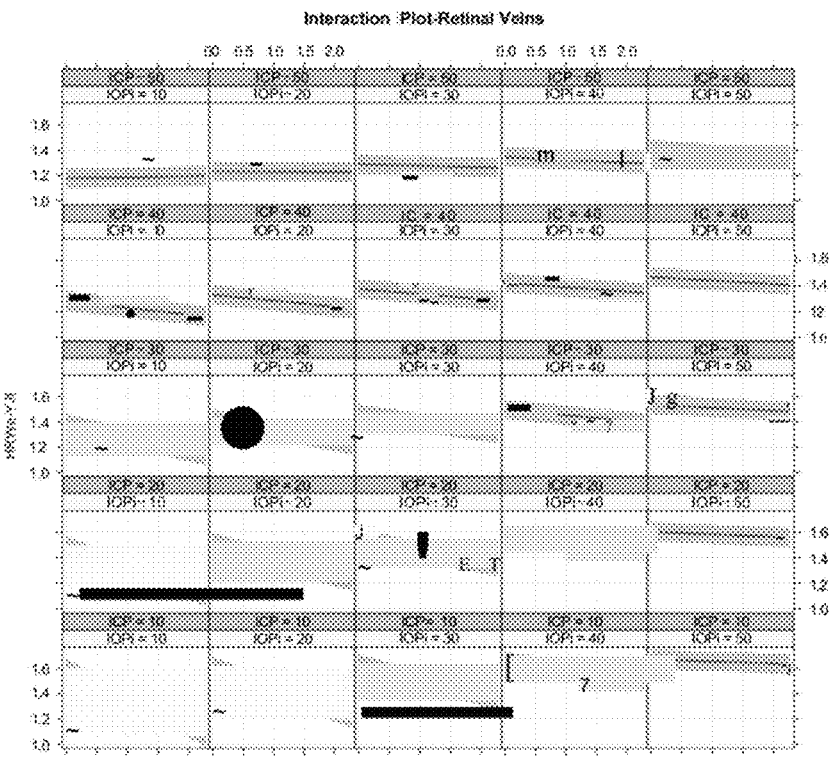
Fig. 25
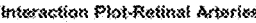
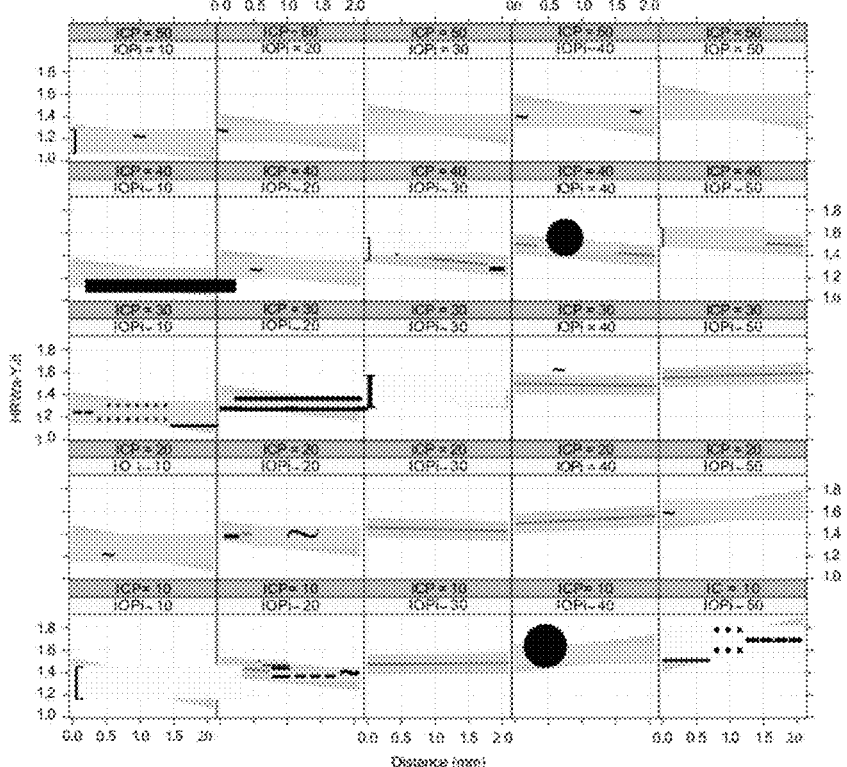
Fig. 26

SYSTEM AND METHOD FOR NON-INVASIVE DETERMINATION OF INTRACRANIAL PRESSURE

This application is a national application based on Patent Cooperation Treaty Patent Application No. PCT/AU2022/050238, filed on Mar. 17, 2022, the entire contents of which are incorporated herein by reference.

This application claims under 35 U.S.C. § 119(a) the benefit of the filing dates of: 1) Australian Patent Application No. 2021900788, filed on Mar. 18, 2021; and 2) Australian Patent Application No. 2021903392, filed on Oct. 22, 2021, the entire contents of each of which are incorporated herein by reference.

BACKGROUND OF THE INVENTION

Field of the Invention

The present invention generally relates to a system and method for determining intracranial pressure. The invention also relates to a non-invasive method and system for determining intercranial pressure.

Description of Related Art

The measurement and monitoring of intracranial pressure (ICP) for instantaneous absolute) pressures as well as changes in pressure among patients with head injury, stroke oedema, idiopathic intracranial hypertension, hydrocephalus, papilloedema, acute intracranial haemorrhage and other conditions, provides necessary, and often vital information upon which medical and surgical treatment can be based.

Currently, invasive techniques are used to measure ICP despite the many shortcomings of such practices. Continuous ICP measurement devices to monitor these conditions require a surgeon to drill a hole through the skull to implant transducers within brain tissue or to locate fluid connected tubes into the central brain ventricles. Intermittent measures can be obtained by needle puncture of the lumbar dura by lumbar puncture, to measure the cerebrospinal fluid (CSF) pressure. CSF pressure and ICP are known to be equivalent so the terms are used interchangeably.

Such procedures carry the risk of brain haemorrhage (up to 6%), malfunction, brain herniation and/or infection (up to 27%) and, furthermore, are expensive. Invasive ICP measuring devices comprise external ventricular drains (EVD) coupled to transducers and tissue micro-transducers (e.g. Camino, Cadman, Raumedic) all inserted through skull burr holes. Relevant diseases (described above) involve disorders of elevated ICP, but other disorders such as glaucoma, normal tension hydrocephalus and ventriculoperitoneal shunt overdrain require ICP monitoring and are partly caused by low ICP.

Other non-invasive approaches have been proposed to estimate ICP, including using the combination or retinal arterial flow velocities and venous pulsation pressure (Cerepress), tympanic membrane displacement in the ear, ultrasonic detection of cranial pulsations, transcranial Doppler (TCD) ultrasonography of the middle cerebral artery, optic nerve sheath diameter and CT or MRI assessment of CSF volume. However, none of these has been shown to be sufficiently accurate at high ICP and none gives any useful measurements at low ICP. Furthermore, existing non-invasive technologies have poor accuracy. For example, the tympanic membrane displacement method is based on acoustic stapedial reflex that, in theory, can measure intraranial pressure indirectly by measuring displacement of the eardrum since ICP is transmitted from the CSF to the perilymphatic fluid of the scala tympana in the labyrinth. However, this method has drawbacks due to the indirect nature of the measurement, poor accuracy and the necessity of having a patent, unobstructed cochlear aqueduct.

An ophthalmodynamometric method for estimating ICP was first described in 1925 by Baurmann. More recent techniques combine ophthalmodynamometry with reflectance oximetry of the retina or ultrasound measurement of blood flow in the central retinal artery (see US 2004/0230124) or automate the method by adding a camera and image processing software for detecting venous pulsations from a sequence of images of the eye fundus (see US 2006/0206037). However, the accuracy of ophthalmodynamometry combined with reflectance oximetry or central retinal artery flow appears little different from ophthalmodynamometry alone. Classically, an ophthalmodynamometer has been used to apply force (ODF) on the eye, and elevate intraocular pressure (IOP), while an observer views the central retinal vein and notes the force when retinal vein pulsation just begins. The induced IOP is then calculated from the baseline IOP and ODF and termed the venous pulsation pressure (VPP). VPP determination is very subjective due to varying abilities of observers to detect the threshold at which veins pulsate. This adds one element of error to the measurement. Any automated method using blood column analysis suffers from the variation in human retinal vein anatomy, with there being markedly varying shapes and sizes of the retinal veins. Some more recent techniques rely upon detecting changes within the central retinal vein wall, but this is a small venous segment with great variation between individuals so both human judgement of its pulsation or machine judgement of size variation using threshold change detection is prone to wide variation and hence inaccuracy.

Analysis of modified photoplethysmographic data presents further unique analytic challenges, including considerable intra- and inter-individual variability of the pulsation amplitude and timing characteristics (known as heteroscedasticity). While there are numerous reasons why heteroscedasticity can exist, a common explanation is that the error range changes proportionally with a variable in the model. Although heteroscedasticity does not cause bias in the coefficient estimates, it does make the estimates less precise. This property poses limitations on the ability to apply deterministic mathematical models to both the interpretation of computational findings and the generation of accurate predictions.

It is desirable for embodiments of the present invention to address at least partially one or more of the disadvantages of the methods or systems above. Further it is preferred that embodiments of the present invention provide methods and systems, which can determine intracranial pressure non-invasively and more accurately.

It is to be understood that, if any prior art publication is referred to herein, such reference does not constitute an admission that the publication forms a part of the common general knowledge in the art, in Australia or any other country.

SUMMARY OF THE INVENTION

According to a first aspect of the present invention there is provided a method for determining intracranial pressure (ICP) of a subject non-invasively, the method including the steps of:

applying at least one selected controlled force to an eye of the subject;

imaging retinal vascular pulsation of the eye of the subject over at least one cardiac cycle at the at least one selected controlled force;

processing the retinal vascular pulsation images to produce retinal vascular pulsation amplitude data as a time-varying signal;

decomposing the time-varying signal into at least two frequency components representing the time-varying signal;

determining intracranial pressure from a data basis which includes at least information associated with the frequency components, and wherein the retinal vascular pulsation data includes at least retinal arterial pulsation data.

The selected controlled force applies pressure to the eye and by applying one or more eye pressure settings multiple pressure settings can be produced by applying multiple selected known, controlled forces.

In an embodiment the retinal vascular pulsation data is primarily retinal arterial pulsation data.

In an embodiment, the decomposition of the time-varying signal into at least two frequency components representing the time-varying signal comprises decomposition with respect to frequency. Such decomposition with respect to frequency is often termed analysis in the frequency domain or Fourier domain analysis. Frequency domain or Fourier domain analysis provides information on the quantity of the signal which lies within a frequency band over a range of frequencies.

Decomposing the time-varying signal into at least two frequency components provides a frequency domain characterisation of the retinal vascular pulsation amplitude data. Thereby enabling analysis of this characterisation of the vascular pulsation amplitude data in the frequency domain, rather than analysis in the time domain. The data basis includes at least two frequency components characterising the retinal vascular pulsation amplitude data in the frequency domain.

Conversion of the time-varying signal, time domain signal, into the frequency domain signal also enables selection of separate frequency components for analysis, thus enabling frequency components, including harmonics and Fourier coefficients of the harmonics, to be utilised in linear modelling to interpret intracranial pressure results. For example, applying a hierarchical linear mixed-effects model. And from such modelling, identifying the most significant frequency components to enable prediction of intracranial pressure. Identification of these most significant frequency components can inform selection of training data set parameters for training a machine learning model for prediction of intracranial pressure. As is described below, frequency domain characterisation can have a standardising effect on comparisons between different series. Thus, simplifying analysis of the signals using mathematical techniques. The standardising effect of frequency domain analysis can have advantages in enabling machine learning based intracranial pressure predictions.

In another embodiment, the data basis includes subject state data. The subject state data can include any information recorded from the subject including induced intraocular pressure of the eye, laterality or hemiretina location of the recorded segment of artery or vein of the eye, pulse, oxygen saturation of haemoglobin or blood pressure. Laterality or hemiretina location refers to whether it is the left or right eye, or which half of the eye respectively. The information can also include whether the retinal vascular pulsation data is recorded from which vessel type, i.e. artery or vein.

The method can include the step of determining intracranial pressure includes using a trained model, which has been trained to define a relationship between the intracranial pressure and the data basis. The method can also include, prior to applying the trained model, the step of retrieving a training data set and executing a model learning process to train the model based on the training data set to define the relationship between the intracranial pressure and the data basis. The data basis and training data set can be substantially the same types of values.

Preferably, the training data set includes the measured intracranial pressure of the subject. More preferably, the training data set includes induced intraocular pressure of the eye of the subject. In a preferred embodiment, the data basis and/or subject state data includes induced intraocular pressure of the eye of the subject. The induced intraocular pressure is preferably calculated from the at least one selected controlled force applied to the eye of the subject.

Decomposition with respect to frequency, (also known as Fourier or frequency domain analysis) can include that each of the at least two frequency components can be a harmonic of the retinal vascular pulsation amplitude data. The at least two frequency components can be harmonics of a Fourier series expansion. Preferably, the Fourier series expansion has first and second harmonics as follows:

$$\mathcal{F}\left(f(t)_p\right) = a_0 + \sum_{n=1}^{\infty} a_n \cdot \cos(n\pi t) + b_n \cdot \sin(n\pi t)$$

wherein $f(t)_p$=the periodic component of the time series, $a_0$=coefficient representing the mean of $f(t)_p$, $a_n$=coefficient of the cosine function of $f(t)_p$, $b_n$=coefficient of the sine function of $f(t)_p$ and n=integer 0, 1, 2 . . . etc representing the harmonic component. The Fourier series expansion can include third and/or higher order harmonics.

Preferably, the training data set includes information associated with the frequency components, for example, at least one coefficient associated with the frequency components. Information associated with the frequency components principally includes at least one of the following: amplitude, timing information, harmonic and Fourier analysis fit coefficients. More preferably, the training data set includes harmonic regression waveform amplitude data, $HRW_a$, which is defined as the combination of the coefficients $a_{n,1}$, $a_{n,2}$, $b_{n,1}$ and $b_{n,2}$ of the frequency components. The data basis can also include the harmonic regression waveform amplitude data, $HRW_a$. Even more preferably, the training data set includes retinal vascular pulsation amplitude data as a function of different distances relative to a centre of an optic nerve of the eye i.e. the location of the recorded segment of artery or vein of the eye. The data basis can also include the distance relative to a centre of an optic nerve of the eye of the recorded segment of artery or vein. In other words, the data basis can include pulsation amplitude information measured at multiple locations from the retinal arteries, veins and their tributary vessels within the optic disc and surrounding retina. Moreover, the training data set can include laterality or hemiretina location of the recorded segment of artery or vein of the eye. The data basis/patient state data can include information on the laterality or hemiretina location of the recorded segment of artery or vein of the eye. The information can also include whether the retinal vascular pulsation data is recorded from which vessel type, i.e. artery or vein. The data basis and training data set can be substantially the same types of values, or at least information type of the data basis is a subset of the information type of the training data set.

In another embodiment, the retinal vascular pulsation amplitude data is correlated by laterality location of the recorded segment of artery or vein of the eye.

In yet another embodiment, the retinal vascular pulsation amplitude data is correlated by hemiretina location of the recorded segment of artery or vein of the eye.

In a preferred embodiment, the model learning process is a regression model learning process. The model learning process is preferably a decision tree regression model learning process.

The method may comprise the step of imaging retinal vascular pulsation of an eye of the subject over at least three cardiac cycles. Preferably, the method comprises the step of measuring a pulse of the subject and utilising the pulse to synchronise cardiac cycle timing to the retinal vascular pulsation amplitude data. The time-varying signal may be based on the cardiac cycle.

The method may comprise the step of imaging retinal vascular pulsation of the eye using an ophthalmodynamometer force (ODF) device for applying the selected force to the eye of the subject. Preferably, imaging retinal vascular pulsation including imaging at a range of selected force (ODF) values to obtain a range of induced intraocular pressures.

In an embodiment, the ODF device is a video ophthalmodynamometer force device having a camera attached to a contact lens within a force transducer ophthalmodynamometer.

In a preferred embodiment, the method includes determining intracranial pressure by use of a further trained modelling process wherein the retinal vascular pulsation amplitude data is primarily retinal venous pulsation data.

In a second aspect of the present invention there is provided a method of determining accuracy of a non-invasive determination of intracranial pressure, including the step of:

applying at least one selected controlled force to an eye of the subject;

taking a first plurality of measurements associated with the retinal arterial pulsation data taken from eyes of a subject at the at least one selected controlled force;

taking a second plurality of measurements associated with the retinal venous pulsation data taken from the eyes of the subject at the at least one selected controlled force;

determining a first plurality of determined intracranial pressures from the arterial data by a first trained model using the method as described above;

determining a second plurality of determined intracranial pressures from the venous data by a second trained model as described above; and determining the accuracy of the intracranial pressure by comparing the first and second pluralities of intracranial pressures.

According to an embodiment, the method can include comparing the first and second pluralities of intracranial pressure using a mode of central tendency, such as the mean or median. Preferably, the method includes the step of comparing the peak densities of the first and second pluralities of determined intracranial pressures.

According to a third aspect of the present invention there is provided a system for determining intracranial pressure non-invasively, including:

a contact lens;

at least one force transducer for controllably applying a selected force to an eye of a subject;

a camera for imaging retinal vascular pulsation of an eye of the subject over at least one cardiac cycle at the at least one selected force;

a control module for controlling the force applied to the eye by the force transducers; and a processing module for determining intracranial pressure (ICP) of the subject, the processing module being configured to:

receive the retinal vascular pulsation images from the camera;

process the retinal vascular pulsation images to produce retinal vascular pulsation amplitude data as a time-varying signal at the at least one selected force;

decompose the time-varying signal into at least two frequency components representing the time-varying signal; and determine an intracranial pressure from a data basis which includes at least information associated with the frequency components; and wherein retinal vascular pulsation data includes at least retinal arterial pulsation data.

In a preferred embodiment the processing module determines intracranial pressure from the data basis using a trained model which has been trained to define a relationship between the intracranial pressure and the data basis. The processing module can determine the intracranial pressure according to the method as described above. Preferably, the processing module decomposes the time-varying signal into at least two frequency components with respect to frequency (frequency/Fourier domain analysis).

The system may be a self-contained portable apparatus, and/or the control or processing module is in the form of a hand-held device. The system may further include a communication module configured to communicate between the camera and the processing module. In an embodiment, the processing module is located external to the camera.

According to a third aspect of the present invention there is provided an non-invasive intracranial pressure-determining computer software product configured to:

receive retinal vascular pulsation images from a camera of an ODF device;

receive controlled selected force information applied to the eye or associated pressure data;

process the retinal vascular pulsation images to produce retinal vascular pulsation amplitude data as a time-varying signal;

decompose the time-varying signal into at least two frequency components representing the time-varying signal;

determine an intracranial pressure from a data basis which includes at least information associated with the frequency components;

wherein the retinal vascular pulsation data includes at least retinal arterial pulsation data.

The software product can preferably include that determining the intracranial pressure comprises using a trained model which has been trained to define a relationship between the intracranial pressure and the data basis. Preferably, the software product decomposes the time-varying signal into at least two frequency components with respect to frequency (frequency/Fourier domain analysis).

The data basis can include one or more of the following: induced intraocular pressure (IOP$_i$), at least one coefficient of the frequency components, a combination of the frequency components (harmonic regression waveform amplitude data ($HRW_a$)), location of the recorded segment of artery or vein of the eye, information on laterality location of the recorded segment of artery or vein of the eye of the eye, information on the hemiretina, location of the recorded segment of artery or vein of the eye of the eye, and distance of the recorded segment of artery or vein from the central optic nerve.

Prior to applying the trained model, the software product can be configured to retrieve a training data set and execute a model learning process based on the training data set to define the relationship between the intracranial pressure and the data basis to train the model.

The training data set can include one or more values of the following: induced intraocular pressure ($IOP_i$), at least one coefficient of the frequency components, harmonic regression waveform amplitude data ($HRW_a$), location of the recorded segment of artery or vein of the eye information on laterality location of the recorded segment of artery or vein of the eye, information on the hemiretina, location of the recorded segment of artery or vein of the eye, measured intracranial pressure, and distance of the recorded segment of artery or vein from the central optic nerve.

The model learning process is preferably a decision tree regression model learning process.

According to a yet further aspect of the present invention there is provided a method as described above or a software product as described above, wherein the measured intracranial pressure is measured by an invasive process, such as a lumbar puncture.

BRIEF DESCRIPTION OF THE DRAWINGS

One or more embodiments of the present invention will hereinafter be described with reference to the accompanying Figures, as follows.

FIG. 21 are violin plots of the distribution of $HRW_a$ with respect to normal ICP and high ICP.

FIG. 25 shows trellis graphs demonstrating the mixed-effects linear regression model with interactions of the Yeo-Johnson transformed venous harmonic regression waveform amplitude ($HRW_{a-YJt}$) with respect to venous arteries.

FIG. 26 shows a trellis graph demonstrating the mixed-effects linear regression model with interactions of the Yeo-Johnson transformed arterial harmonic regression waveform amplitude ($HRW_{a-YJt}$) with respect to retinal arteries.

DETAILED DESCRIPTION

Referring now to FIGS. 1 to 26, there is described methods and systems for determining intracranial pressure of a subject non-invasively according to preferred embodiments of the present invention.

The preferred methods and systems are based on extensive clinical studies conducted by the applicants involving participants were recruited from the Lions Eye Institute over a period of five years (2015-2020). Prior to lumbar puncture, subjects underwent modified photo-plethysmography, which consists of contact lens ophthalmodynamometry to vary induced intraocular pressure (IOP), with concomitant imaging of the retinal vascular pulsation. Details of the system for modified photo-plethymography will be described in the following paragraphs. These studies provided data sets that were utilised by the inventors in the conception and reduction to practice of the present invention.

Figure 5:
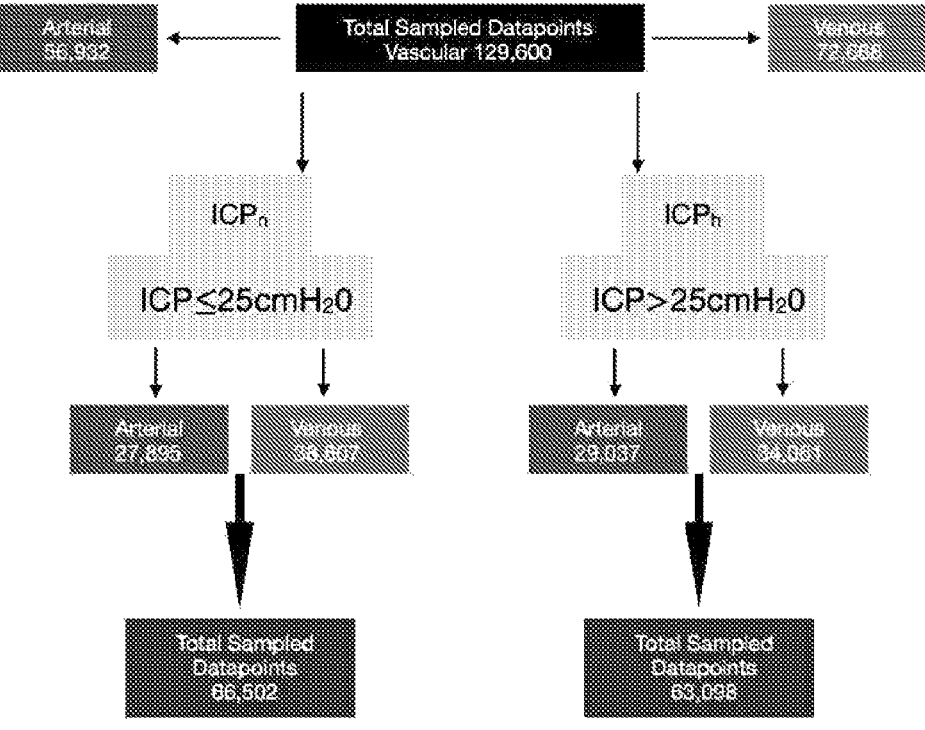
FIG. 5 shows the classification of the study population image data points according to the second example of the present invention.

The methods described herein are a practical application of discoveries and insights gained from the study, and the study is therefore referred to in paragraphs below. Participants in the study were required to have clear ocular media, no prior history of co-existing retina or optic nerve disease and were needed to be able to cooperate with the imaging protocol. There was a total of 21 patients in the training and test study groups, of these, ten cases were in the high intracranial pressure group (ICP$_h$>25 cmwater) and eight in the normal intracranial pressure group (ICP$_n$_25 cmwater), see FIGS. 4 and 5. An ICP of 25 cm water was considered the upper normal limit. Three cases overlapped both groups because of interchanging between the ICP$_n$ to the ICP$_h$ groups over five years (2015-2020) of observation (see FIG. 4). A total of 129,600 data points was sampled from the images from the study group, 56,932 arterial and 72,668 venous data-points (FIG. 5).

Image Acquisition

The optic nerve was imaged under a dynamic range of intraocular pressures using a Meditron ophthalmodynamometer (ODF device) (Meditron GmbH, Poststrasse, Volklingen, Germany).

Figure 1:
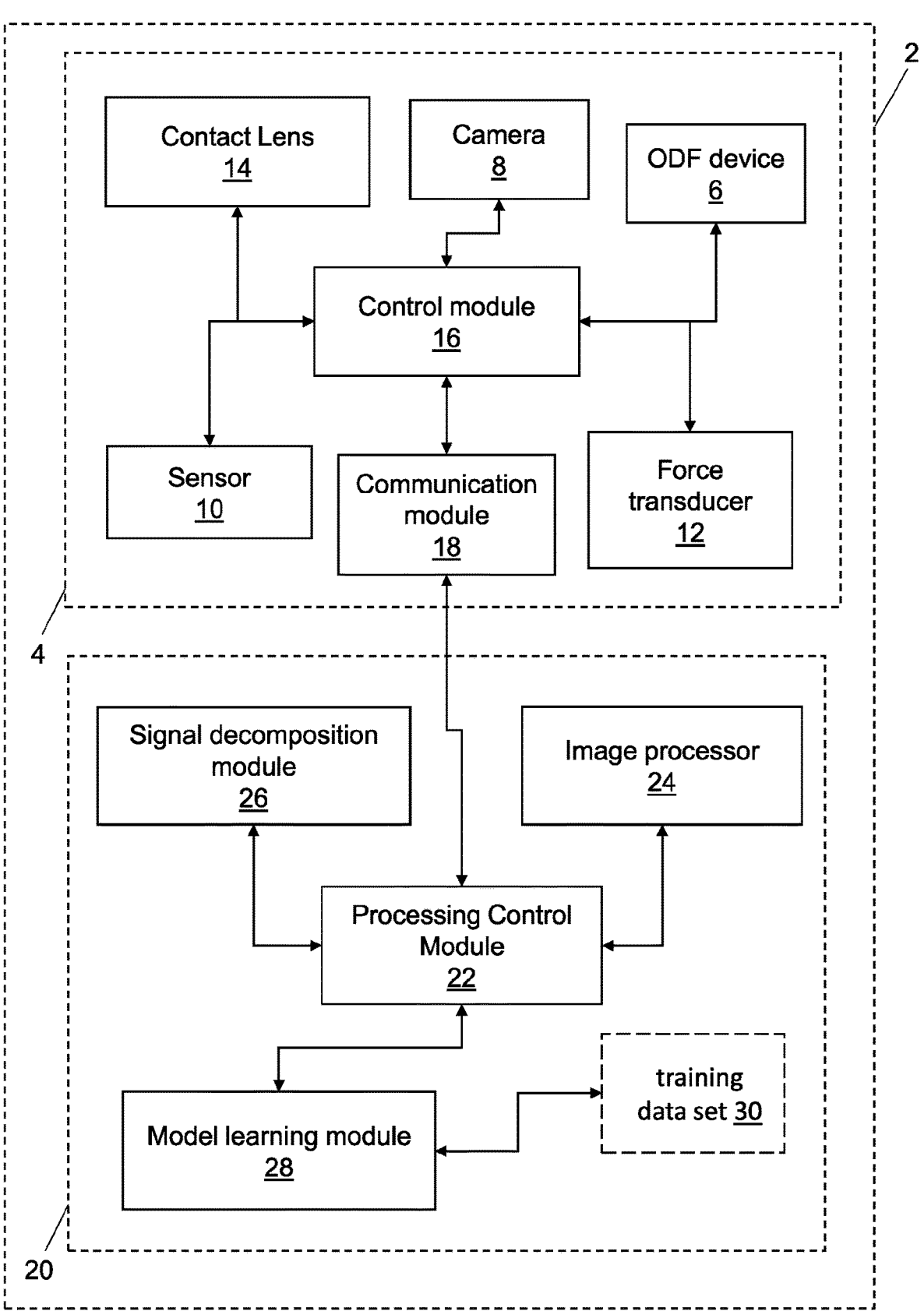
FIG. 1 is a schematic diagram of the system for determining intracranial pressure according to a preferred embodiment of the present invention.

FIG. 1 is a schematic of the system 2 for acquiring images and from these images determining intracranial pressure. The system includes a video ophthalmodynamometer force (ODF) measuring apparatus 4 in form of an ODF device 6, a camera 8, at least one sensor 10 and a force transducer 12 for controllably applying a force to an eye of the subject via contact lens 14, and a control module 16. The control module 16 can include a processor, memory for data storage and an interface if necessary in the form of a display, output or data input (not shown). The control module 16 is adapted to allow the inputting of information about the subject, such as blood pressure, location of the recorded segment of artery or vein of the eye, laterality or hemiretina information of the eye (i.e. lateral or hemiretina location of the recorded segment of artery or vein of the eye), and haemoglobin concentration, and can display video images collected by ODF device of the optic disc blood vessels and allow the manual selection of venous and arterial segments if required. The control module 16 is also adapted to log data associated with image capture, such as ODF force applied, timing etc. An operator can do any one or more of the following: adjust the ODF force settings of ODF device using the control module 16, instruct the camera 8 to commence or cease recording and to adjust any of the settings in respect of the images and/or camera 8, save the images as data into the memory, instruct the at least one sensor 10 to commence or cease recording sensor data and to adjust any of the settings in respect of the sensor 10 and/or sensor data and transmit information/instructions to and from the control module 16 to a communication module 18. The control module 16 can be in a form of a computer. The control module 16 can include a portable computer such as a laptop or hand-held personal device such as a tablet, smart phone or the like.

The ophthalmodynamometer consists of a sensor 10 in the form of a sensor ring, which measures the compression force on the eye. The sensor surrounds a central Goldmann three-mirror fundus contact lens 14. The ophthalmodynamometric force (ODF) displayed as Meditron units (mu), which were then converted to induced intraocular pressure (IOPi) using the following formula: IOP$_i$=0:89*ODF+IOP$_b$. where IOP$_b$ is the baseline intraocular pressure in millimeters mercury (mmHg).

In the embodiment used in the study, video of the optic nerve was captured with an imaging slit-lamp (Carl Zeiss, Germany) with a mounted digital camera 8 (Canon 5D Mark III, Japan). However, alternative equipment suitable to capture images of the optic nerve and vascular pulses may be used and are contemplated within system embodiments. In this study, several sequences of at least three cardiac cycles in length were taken, each at a rate of 25 frames/second. When possible, recordings were taken from both eyes. A range of induced intraocular pressure values was between 7-73 mmHg were obtained from each subject. The camera 8 is configured for imaging retinal vascular pulsation of an eye of the subject over at least one cardiac cycle. Videos showing motion artifact, reflection from the optical media, or decentration of the optic nerve in the image sequence for preferably three or more consecutive cardiac cycles.

The at least one sensor 10 for monitoring properties of the subject can include a sphygmomanometer for measuring the blood pressure of the subject, a pulse oximeter for monitoring the saturation of the subject's haemoglobin, or an intraocular pressure measurement, for example a tonometer for determining a baseline value of the intraocular pressure of the subject. The pulse oximeter can have an indicator which can indicate the peak of the systole and which can be used to synchronise the images captured by the camera 8 with the cardiac cycle, preferably in communication with the control module. The at least one sensor 10 may include other sensors which can be configured to collect state data of the subject as would be known to a person skilled in the art.

In this study a pulse oximeter 10 (Nellcor N65, Covidien, Mansfield, MA) was applied to the right index finger; the audio signal from the pulse oximeter 10 was recorded with the video sequence of the optic nerve. This allowed synchronization of the retinal vascular pulse with the cardiac cycle. Timing of the cardiac cycle was generated from the audio signal from the subject's pulse oximetry recorded on the audio trace of the video segment, which in turn enabled the mathematical analysis of the periodic component from green channel transmittance. It is preferred that a single high-quality three-cardiac cycle length video recording is extracted from each recording session.

Image Analysis

The system 2 can also include a processing module 20 for processing the images captured by the camera 8.

The processing module 20 can be connected directly to the video ophthalmodynamometer apparatus 4 or can be connected via the communication module which can transmit information therebetween either wirelessly or wired communication to the control module 16 which can be located proximal to the video ophthalmodynamometer force (ODF) measuring apparatus 4 or can be located remote from it. Therefore, the communication module 18 may include a wireless communication module for example, WIFI router module, or other mobile communication modules used for data transfer, including satellite, broadband networks, mobile networks and the like. If the control module 16 is a computer having communication means such as a smart phone or laptop, then the communications module 18 is therefore may be integrally part of the control module 16.

Figure 2:
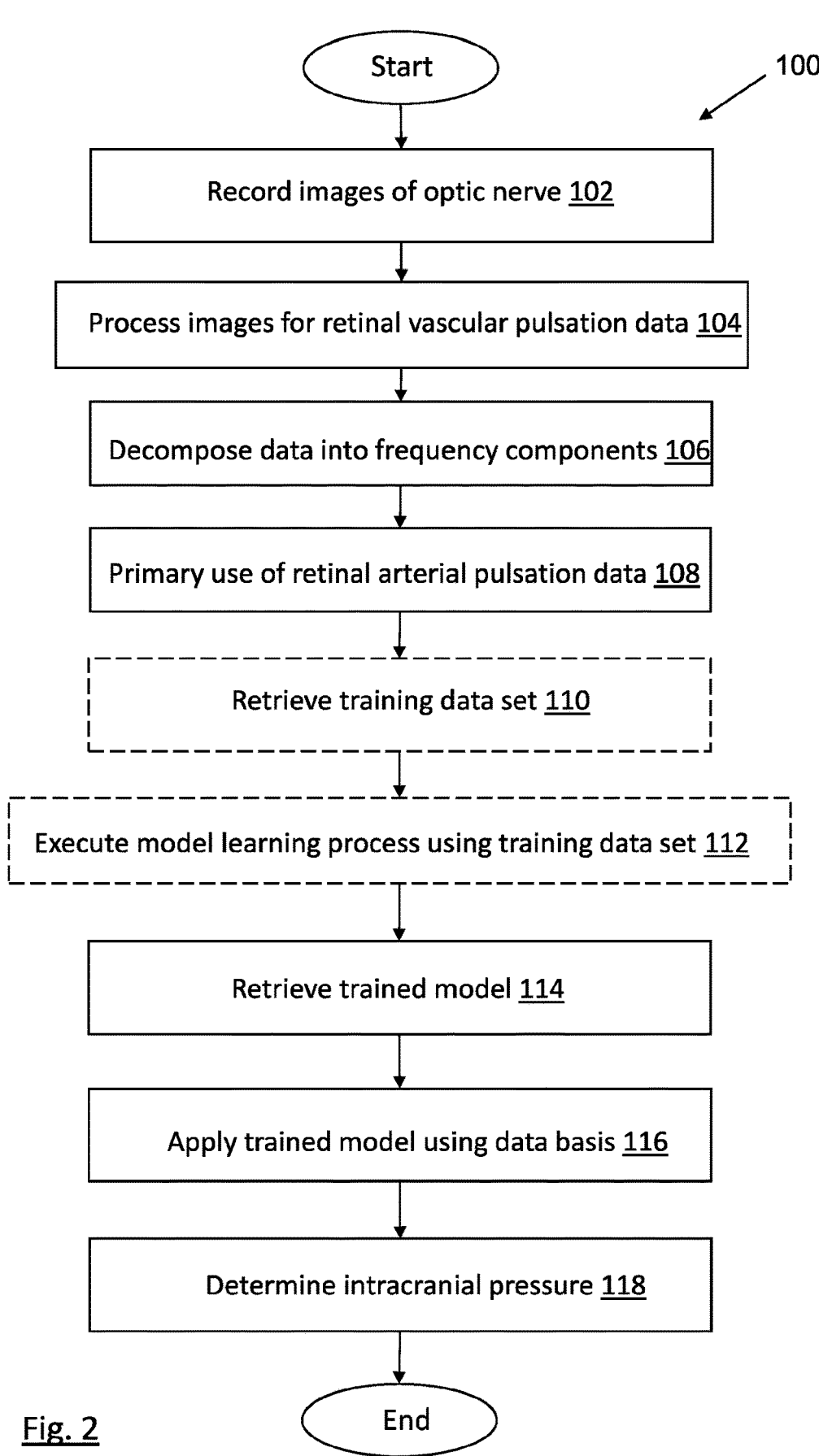
FIG. 2 is a flowchart of a method for determining intracranial pressure according to another preferred embodiment of the present invention.

FIG. 2 is a flow diagram of an example method 100 of determining intracranial pressure of the subject using the processing module 20 of the example system outlined in FIG. 1. It is envisaged that an intracranial pressure-determining computer product can be written as a set of instructions to be able to carry out the method described in this disclosure by a processing module in any computing device, including those available in personal mobile devices such as laptops, tablets, smart phones and the like.

At step 102, the apparatus 4, as instructed by the control module 16, can record images of the optic nerve of a selected eye of the subject, specifically the retinal veins and retinal artery branches, at varying selected intraocular pressures (by varying ODF) which can be processed to produce retinal vascular pulsation amplitude data of the eye of the subject as discussed in the above paragraphs.

It is necessary to apply selected controlled force, at at least one selected ODF value, to the eye of the subject to observe the retinal vascular pulsation. In short, the retinal vascular pulsation is unable to be observed without applying the controlled force to the eye. Preferably, a range of selected ODF is applied to the eye to induce a range of intraocular pressures. This is advantageous because there is a relationship between intraocular pressure and actual intracranial pressure, and where the intraocular pressure and actual intracranial pressure are similar or the same, the pulsation amplitude will be more measurable. As the actual intracranial pressure is not typically known at the time of measurement, a range of applied controlled forces must be applied to eye to induce a range of intraocular pressures, and thereby optimising the amplitude of the retinal vascular pulsation and increasing the accuracy of the images taken.

In a particularly preferred embodiment, video images of the optic nerve are taken in several sequences of at least one, and preferably three or more cardiac cycles in length, each at a rate of 25 frames/second. Sequences of one cardiac cycle can be taken, although may produce results with less accuracy. When possible, images were taken from both eyes of the subject. A pulse oximeter 10 was applied to the right index finger; the audio signal from the pulse oximeter was recorded with the video sequence of the optic nerve. This allows synchronisation of the retinal vascular pulsation with the cardiac cycle. Timing of the cardiac cycle was generated from the audio signal from the subject's pulse oximetry recorded on the audio trace of the video segment, which in turn enabled the mathematical analysis of the periodic component from green channel transmittance. It is preferable to extract at least a single high quality three cardiac cycle length video images was extracted from each recording session of a subject.

In the preferred embodiment, the image processing was done in Adobe Photoshop CS6 where individual image frames were extracted from each video sequence and saved as Tagged Image File Format (TIFF) files. Each of these images was cropped to an array of pixels. All images from three cardiac cycles were analysed in R statistical package using custom software. Each data point was represented by the mean of the green channel intensity at time measured as a fraction of the cardiac cycle, rather than in seconds.

The video recordings can be stored in the memory of the control module 16 as data and then transmitted to the processing module by the communication module 18. The system 2 also can collect the images with respect to the cardiac cycle via the pulse oximeter 10 along with other information in respect of the subject.

The processing control module 20 can then control the processing of the images to produce retinal vascular pulsation amplitude data in step 104 by image processing module 24. This image processing step can include that the images are processed to identify hemiretinal vein and tributaries using colour channel separation, in particular, whether the vessels are arteries or veins so that the data can be identified as retinal arterial pulsation data or retinal venous pulsation data. The image processing step can also include identification of segments of the arteries and veins with respect to their distance from the central optic nerve. Multiple segments of arteries and veins can be identified in each step. This process is further detailed in the paragraphs below in the examples carried out by the Applicant.

The processing step 104 can also include signal processing which assists to prepare data for further processing, for example signal averaging, noise reduction and other types of signal processing which would be known by a person skilled in the art.

The retinal vascular pulsation amplitude data is imaged over at least one cardiac cycle but three cardiac cycles or more can also be used for assisting in accounting for any variations. The retinal vascular pulsation amplitude data is thus configured to be presented as a time-varying signal. By timing the collection of the data with the pulse of the subject, the data is also synchronised as a function of the cardiac cycle. The time-varying signal can be converted from a time domain characterisation to a corresponding frequency domain characterisation for analysis in the frequency domain.

The retinal vascular pulsation amplitude data representation as a time-varying signal can then be decomposed into frequency components in step 106 by signal decomposition module 26 to enable analysis in the frequency (analysis in the frequency/Fourier domain). There are several advantages to performing the frequency component decomposition. Characterising the time-varying signals with respect to frequency (otherwise also described as analysis in the Fourier domain) most importantly, through its sine and cosine coefficient magnitudes, standardizes comparisons between different series, and expresses the contribution from a single frequency.

This decomposition is modelled separately for the arteries and veins. The decomposition into frequency (periodic) components with respect to frequency (analysis in the frequency/Fourier domain) is preferably a harmonic regression waveform expansion, also known as a Fourier series expansion. It is preferred that the Fourier series expansion is represented by the following equation (1):

$$\mathcal{F}\left(f(t)_p\right) = a_0 + \sum_{n=1}^{\infty} a_n \cdot \cos(n\pi t) + b_n \cdot \sin(n\pi t) + \epsilon$$

wherein $f(t)_p$=The periodic component of the time series, $a_0$=Coefficient representing the mean of $f(t)_p$, $a_n$=coefficient of the cosine function of $f(t)_p$, $b_n$=coefficient of the sine function of $f(t)_p$, n=integer 0, 1, 2 . . . etc representing the harmonic component $\epsilon$=error term. It is preferred that decomposition is made on the basis of at least two of the frequency components, n≥2, i.e. the first and second order frequencies. Higher harmonic frequency model comparisons were conducted using Akaike Information Criterion (AIC) which showed models with first and second order frequencies were preferred so final analysis was thus limited to first and second harmonics. However, the applicant considers higher orders could also be utilised. The amplitude of the composite (combined first and second harmonic waveforms) was termed the harmonic regression wave amplitude ($HRW_a$).

The study performed by the applicant demonstrated that analysis of photoplethysmographic data in the frequency domain showed positive correlations between retinal vascular pulsatile characteristics in the frequency domain and intracranial pressure. The system disclosed herein is an application of the insights from this study to enable training and utilising of a machine learning model for predicting intercranial pressure from non-invasively obtained photoplethysmographic data. The section below entitled USING A LINEAR MODEL TO INTERPRET INTRACRANIAL PRESSURE RESULTS explains the analysis of study results and identification of positive correlations between frequency domain characteristics of retinal vascular pulsation data and intracranial pressure. This study also indicated the most influential characteristics. Applying these insights, the inventor developed a machine learning approach to train a model to be used to predict intracranial pressure based on non-invasively obtained photoplethysmographic data.

Embodiments provide a system and method for training and application of a machine based leaning model for predicting intracranial pressure. In an embodiment, determining intracranial pressure includes using a trained model, which has been trained to define a relationship between the intracranial pressure and the data basis. For example, a trained regression model. In a preferred embodiment this is a decision tree-based regression model, trained based on a data set including data characterising positive correlations between frequency domain characteristics of retinal vascular pulsation data and intracranial pressure.

In a particularly preferred embodiment, the boost algorithm used is the extreme gradient boost algorithm (XGB) which is an ensemble machine learning regression method based on decision trees, to establish a prediction of ICP and feature importance from the model. Boosting builds decision trees sequentially such that each subsequent tree aims to reduce the errors of the previous tree and the residual errors are then updated. The decision tree is tuned by three hyperparameters, which are lambda ($\lambda$), this parameter reduces the influence of outliers by factoring in the denominator of the similarity score, gamma ($\gamma$), controls branch depth via the gain, and eta ($\eta$), the m learning rate, controls the rate of the branch convergence by scaling the leaf output. The main fine-tuned parameters in the present study included maximum tree depth (maximum depth=10), over 70 iterations, all the other parameters may remain at their default values. R statistical package was used to generate the model for each vascular system independently.

The mathematical principle of XGB depends on defining the objective function (obj($\theta$)), which measures goodness of model fit to the training data ($x_i$). In the preferred embodiments the training data set consisted of nine features (IOP$_i$, HRW$_a$, the cosine and sine coefficients of the first and second harmonic waves ($a_{n1,2}$), ($b_{n1,2}$), hemiretinal location of the vessel (superior or inferior retina), and laterality (right or left eye)). The training labels ($y_i$), which was ICP in our study, were ultimately used to generate predictions of ICP measurements ($\hat{y}_i$). In the XGB algorithm the objective function has two parts: a training loss (L($y_i$; $\hat{y}_i$)) and regularization term (($\Omega/(\theta)$)) as follows.

$$\text{obj}(\theta)=L(y_i,\hat{y}_i)+\Omega(\theta)$$

The regularization term (($\Omega(\theta)$)), through the built-in L1 (lasso regression) and L2 (ridge regression), prevents model overfitting. The training loss (L($y_i$; $\hat{y}_i$)) measures predictive power of the model with respect to the training data $$\sum_{i=1}^{n} L(y_i, \hat{y}_i) = \frac{1}{2}(y_i - \hat{y}_i)^2$$

Model fit begins by generating a base model ($M_0$), which is calculated from the mean for $\hat{y}_i$ from which the residual values ($e=y_i-\hat{y}_i$) are computed. The residuals are then used to estimate a parameter called the similarity score (s) where $n_e$ is the number of residuals:

$$s = \frac{\sum e^2}{n_e + \lambda}$$

At successive decision tree branches, the gain (g) is calculated from the difference between the sum of the branch similarity score and the root similarity score ($g=s_{branch}-s_{root}$). Further branching will not proceed if the gain value is less than the gamma value ($\gamma$, (described below)), which thereby controls the branch depth. The gain is compared for several branching threshold values to maximize this parameter. At each iteration (t) the following function is minimised:

$$L^t = \sum_{i=1}^{n} L(y_i, \hat{y}_i) + T\gamma + \frac{1}{2}\lambda(O_v)^2$$

where, (T) is the number of terminal nodes, ($\gamma$) is a user-defined penalty, which encourages pruning of decision tree branches. The hyperparameter ($\lambda$) has the effect of neutralizing the influence of outlier values. The goal of the computation is to find the scaled output value ($O_v$) of the leaf that minimizes the above equation for $L^t$.

XGB uses the second-order Taylor approximation to solve the equation for optimal output values, this step transforms the objective function to a function in the Euclidean domain where traditional optimization techniques can be used. In general, for the base model ($M_0$) the second-order Taylor approximation is a polynomial of the loss function, where its first and second derivatives are represented by the equation:

$$L(y_0, \hat{y}_0) + O_v = L(y_0, \hat{y}_0) + \left[\frac{\partial}{\partial\hat{y}_0}L(y_0,\hat{y}_0)\right]O_v + \frac{1}{2}\left[\frac{\partial^2}{\partial\hat{y}_0^2}L(y_0,\hat{y}_0)\right]O_v^2$$

The loss function is represented by the gradient ($gO_v$) and the Hessian ($hO_v$) to represent the first and second derivatives respectively. This approximates the equation for $L^t$ with a second-order Taylor polynomial as follows:

$$L(y_0, \hat{y}_0 + O_v) \approx L(y_0, \hat{y}_0) + g_0 O_v + \frac{1}{2}h_0 O_v^2 + L(y_1, \hat{y}_1) +$$

$$g_1 O_v + \frac{1}{2}h_1 O_v^2 + \dots + L(y_n, \hat{y}_n) + g_n O_v + \frac{1}{2}h_n O_v^2 + \frac{1}{2}\lambda(O_v)^2$$

After omitting all terms without output value coefficients, re-arranging and finding the function minimum with respect to $O_v$:

$$\frac{\partial}{\partial O_v}(g_0 + g_1 + g_2 \dots + g_n)O_v \bigg| + \frac{1}{2}(h_0 + h_1 + h_2 \dots + h_n + \lambda)O_v^2 = 0$$

Therefore $O_v$ is as follows:

$$O_v = \frac{(g_0 + g_1 + g_2 \dots + g_n)}{(h_0 + h_1 + h_2 \dots + h_n + \lambda)}$$

A final prediction for each data point is calculated adding the initial prediction to the output value scaled by a third hyper-parameter, learning rate ($\eta$), which determines the model's rate of convergence. Successively trained models ($M_n$) aim to minimize the residuals. Computation stops when the residuals are minimized or when the maximum number of iterations is reached.

Figure 3:
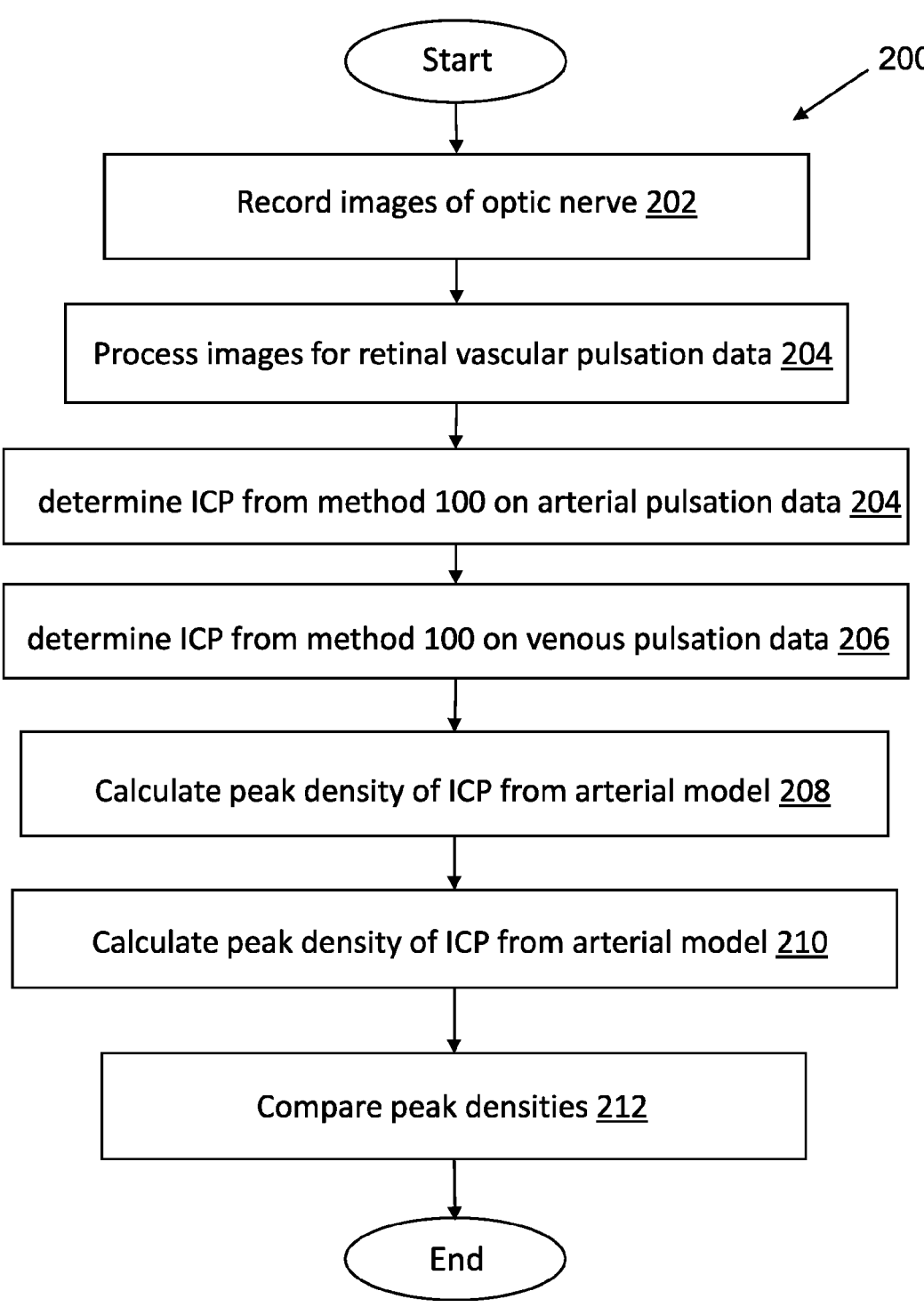
FIG. 3 is a flowchart of a method for determining the accuracy of the determined intracranial pressure according to yet another embodiment of the present invention.
Figure 4:
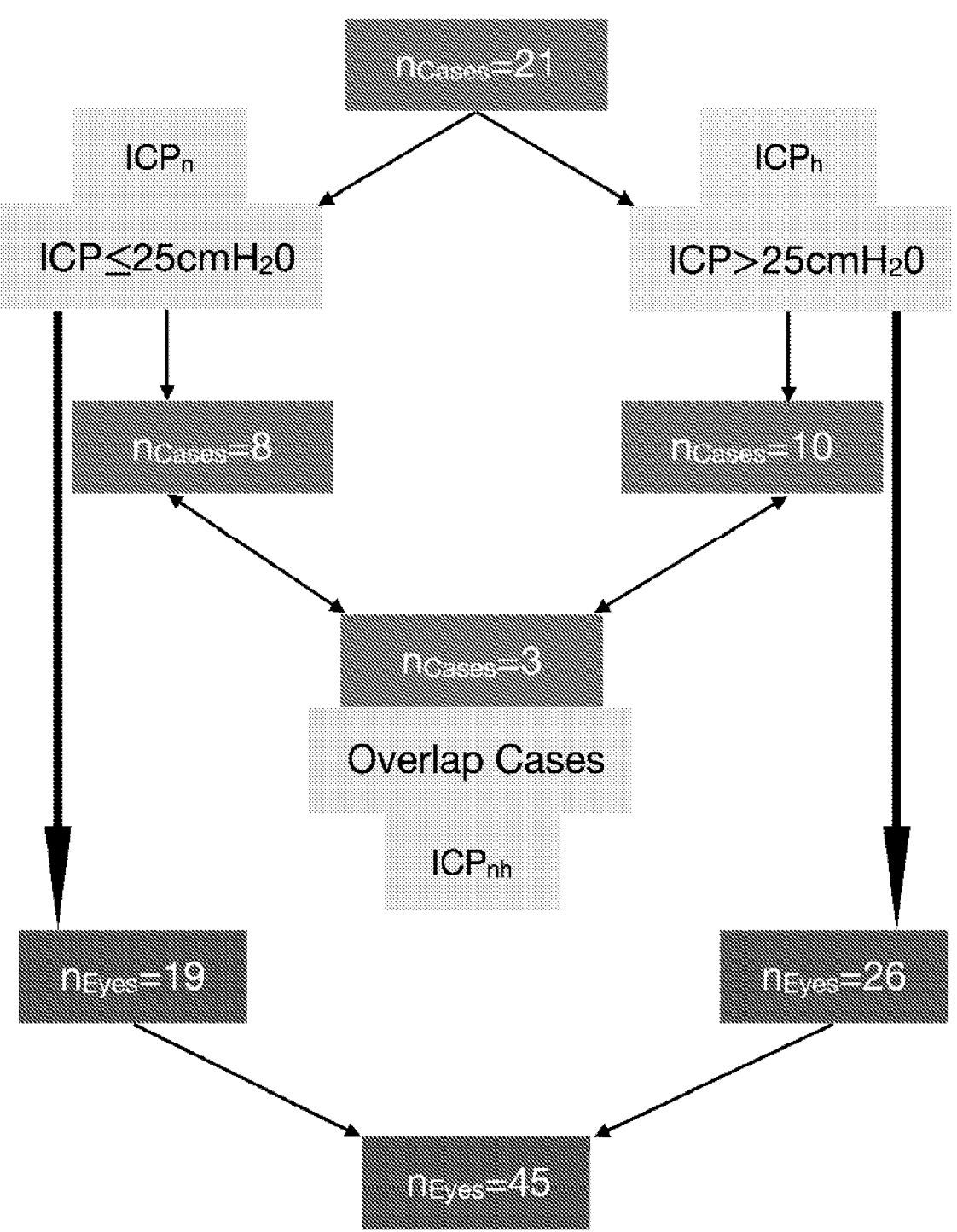
FIG. 4 shows the classification of the study population according to a second example of the present invention.
Figure 16A:
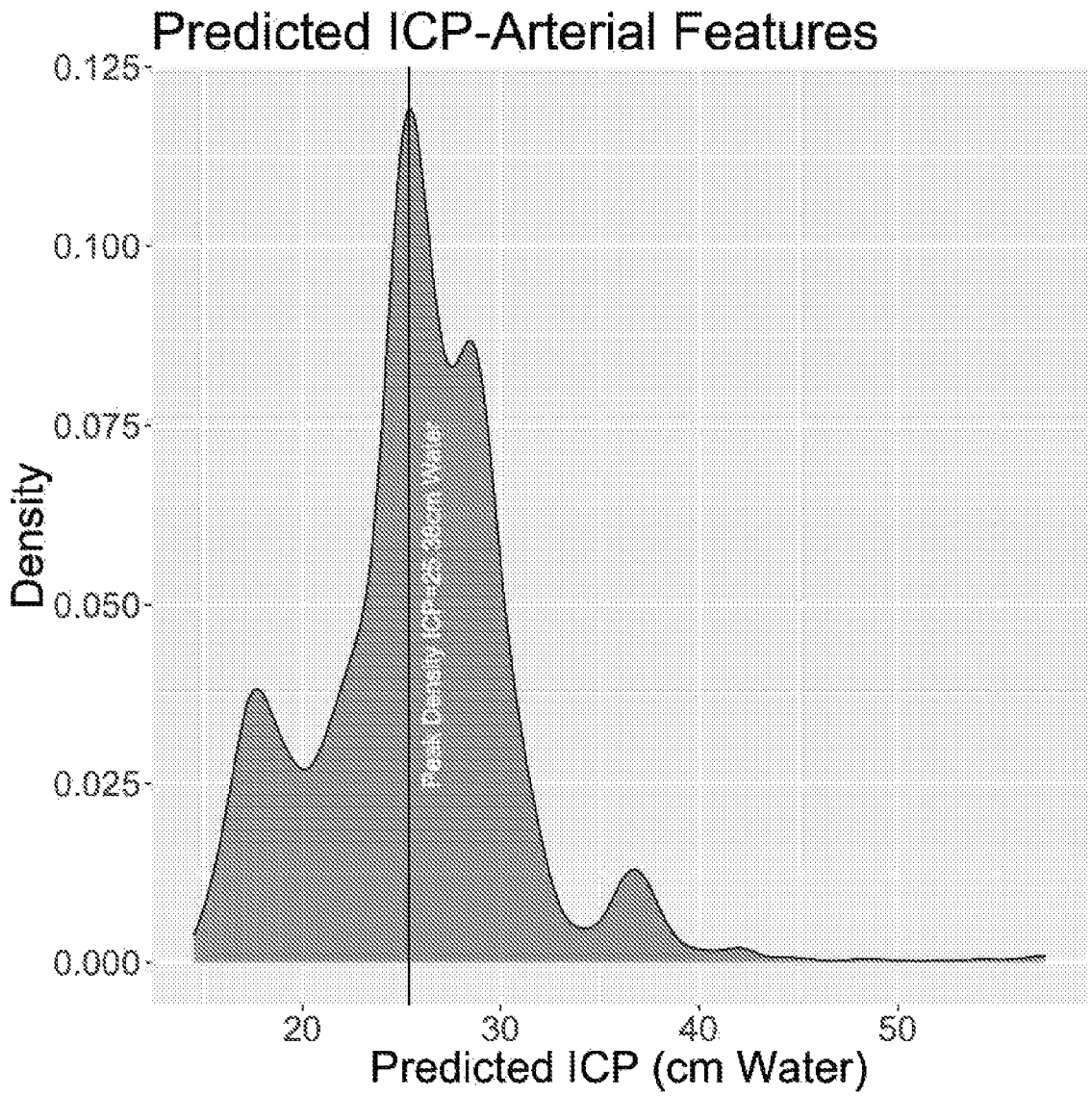
FIG. 16A shows a density plot of predicted ICP for an example case—arterial features.
Figure 16B:
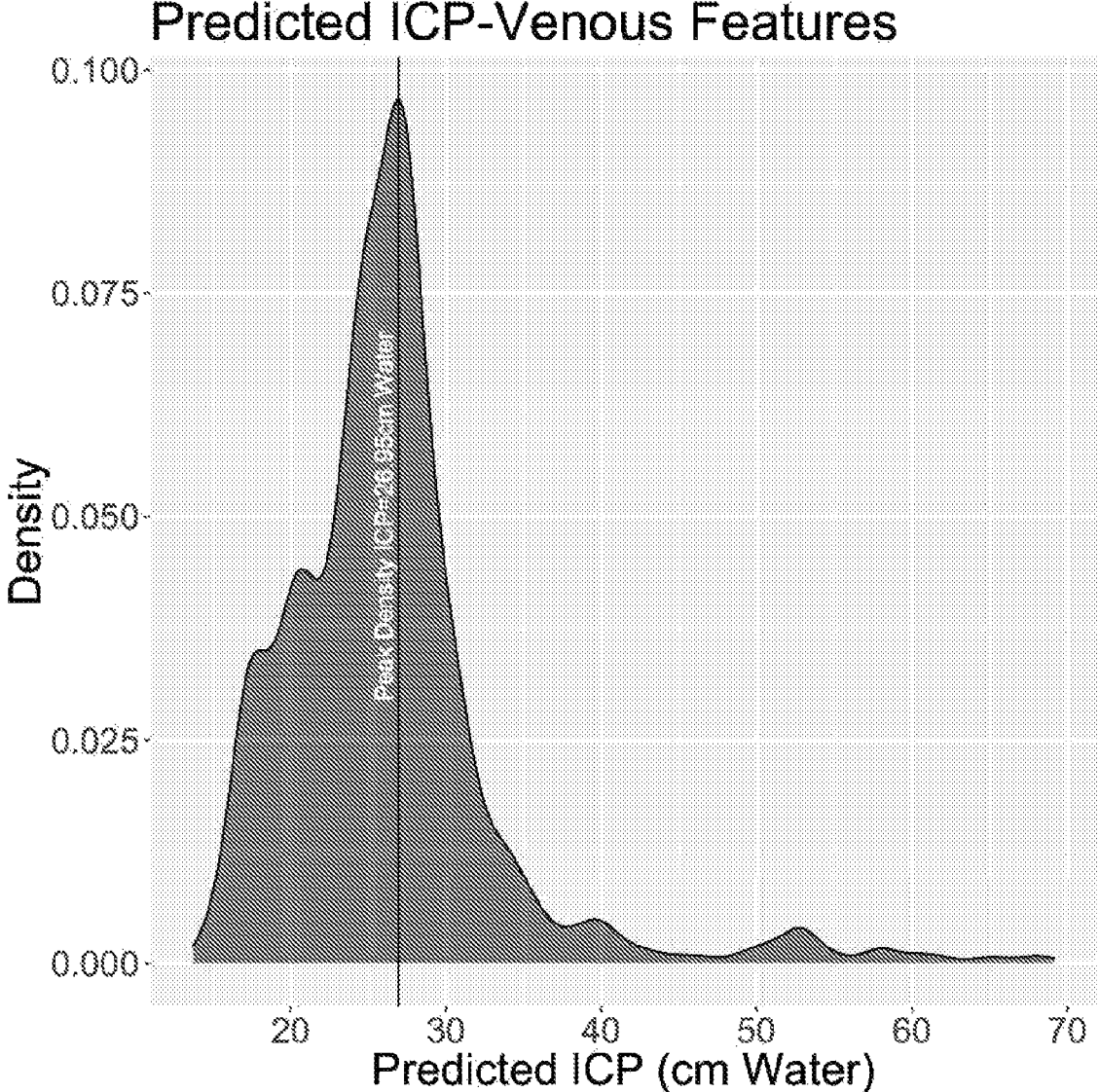
FIG. 16B shows a density plot of predicted ICP for an example case—venous features.
Figure 17:
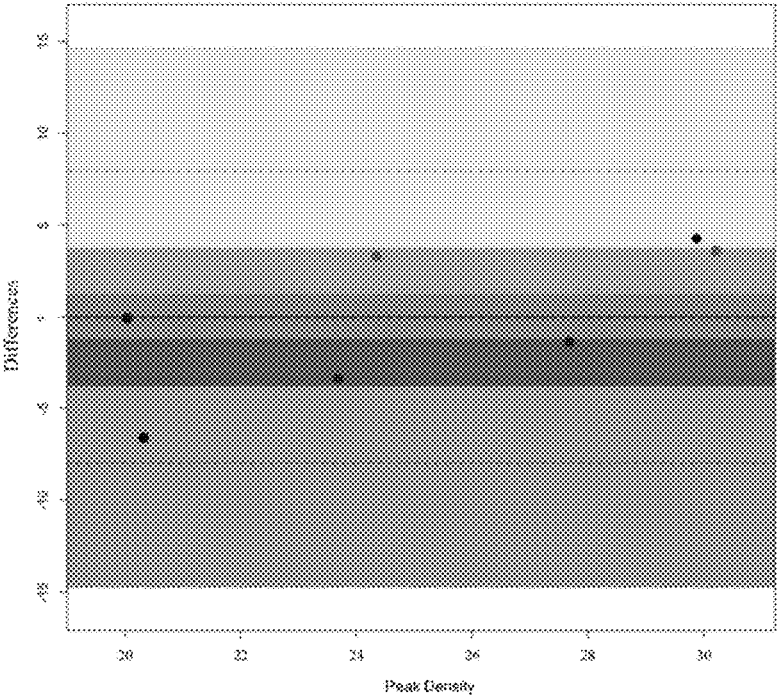
FIG. 17 is a Bland-Altman plot of predicted ICP peak density for the arterial model for cases 1-7.
Figure 18:
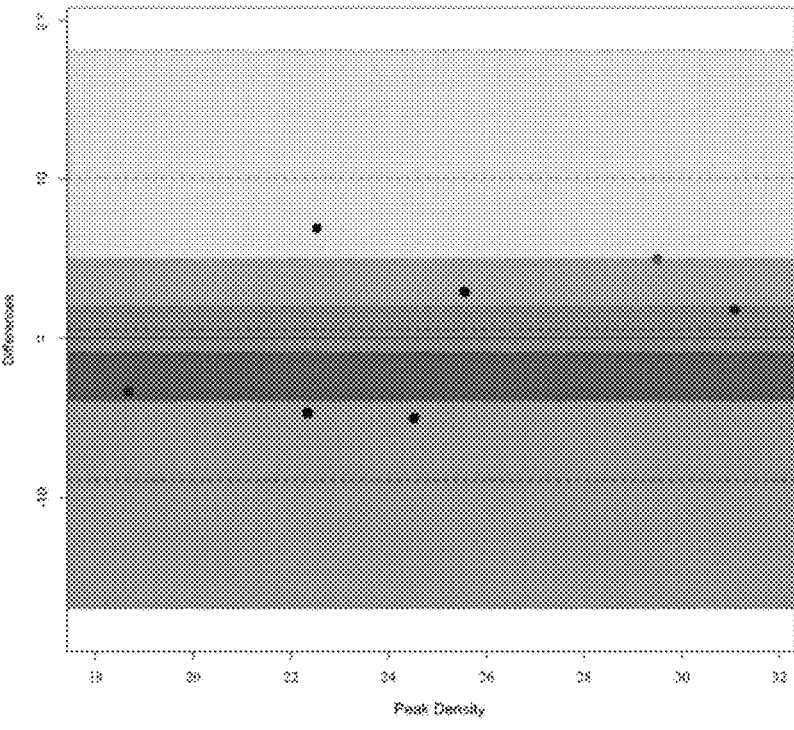
FIG. 18 is a Bland-Altman plot of predicted ICP peak density for the venous model for cases 1-7.

The training set consisted of 85% of randomly selected vascular pulsation points, the testing set consisted of the remaining 15% of the data points. From the validation set mean, median and peak density of the predicted ICP were compared to the measured ICP. The peak density was measured from the highest value of a density plot of the predicted ICP. (FIGS. 3, 16A and 16B). Both Bland-Altman plots and the t-test were used to measure agreement between measured ICP and the mean, median and peak density of the estimated ICP for both the arteries and the veins separately.

Feature importance is a ranking score representing the contribution from the selected feature to the model prediction. It is calculated for a single decision tree by the amount that each attribute split point improves the performance measure, weighted by the number of observations for which the node is responsible. There are three methods for measuring feature importance in XGBoost, weight, which is the number of times a feature is used to split the data across all trees. Cover is the number of times a feature is used to split the data across all trees weighted by the number of training data points that go through those splits, and gain is the average training loss gained when using a particular feature at a branching point. To identify the principal features driving model prediction, SHAP (SHapley Additive exPlanations) values were calculated, this is an additive feature attribution method that provides a quantitative evaluation of the tree ensemble's overall impact in the form of particular feature contributions.

There are several advantages in generating a decision tree regression model for non-invasive intracranial pressure (ICP) prediction using mPPG data. Photoplethysmographic data is characterised by high inter and intra individual variance, therefore machine learning processes can address heteroscedasticity to a certain extent. Compared to other algorithms, decision trees require less effort for data preparation during pre-processing. Vascular pulsation data is non-normal, this imposes limitations with the choice of statistical analyses using hypothesis testing and regression methods, however, a decision tree approach advantageously requires neither data normalization nor scaling. Pre-processing of data involves identification of missing values with subsequent data exclusion or imputation, with decision tree algorithms missing values do not affect the process of building a decision tree. Thus, this machine learning approach also advantageously is less sensitive to data shortcoming and reduces data pre-processing. Other model learning processes disadvantageously require more data preprocessing before execution.

More specifically with parallel processing inherent to the algorithm allows significant shortening of the analysis time. Further gains are achieved using cross validation, which allows for the exact optimum number of boosting iterations in a single run and effective tree pruning, which allows XGB to make splits up to a maximum depth specified by the user. Further pruning of the decision tree in retrograde allow the identification of splits beyond which there is no positive gain. A maximum depth of 10 nodes over 70 iterations were used in our algorithm. Boosting is an ensemble machine learning regression method where trees that are built sequentially such that each subsequent tree aims to reduce the errors of the previous tree and the residual errors are then updated. In this example of use in these methods and systems, the preferred model learning process is an extreme gradient boost algorithm (known as 'XGB').

As discussed in FIGS. 1 to 18, there are described preferred methods and systems of determination of the intracranial pressure using a data basis, which is a non-invasive process. The information taken from the processing of retinal vascular pulsation images can be processed to produce retinal vascular pulsation amplitude data as a time-varying signal. The time-varying signal is decomposed into at least two frequency components representing the time-varying signal with respect to frequency, otherwise known as analysis in the frequency/Fourier domain, which essentially allows standardized comparisons between different series, and expresses the contribution from a single frequency. The data basis used in the non-invasive determination of the intracranial pressure is at least information associated with the frequency components.

The data basis on which the intracranial pressure is determined can also include other data including information on the subject's state. The subject state data can include the induced intraocular pressure which can be calculated from the selected controlled force applied to the eye as discussed above. The subject state data can also include information on the hemiretina and/or laterality of the eye of the subject, blood pressure, cardiac cycle and the like. The data basis can also include information on the distance relative to a centre of an optic nerve of the eye of the recorded segment of artery or vein, i.e. the distance from the centre of optic nerve where the retinal vascular pulsation data is measured.

Figure 9:
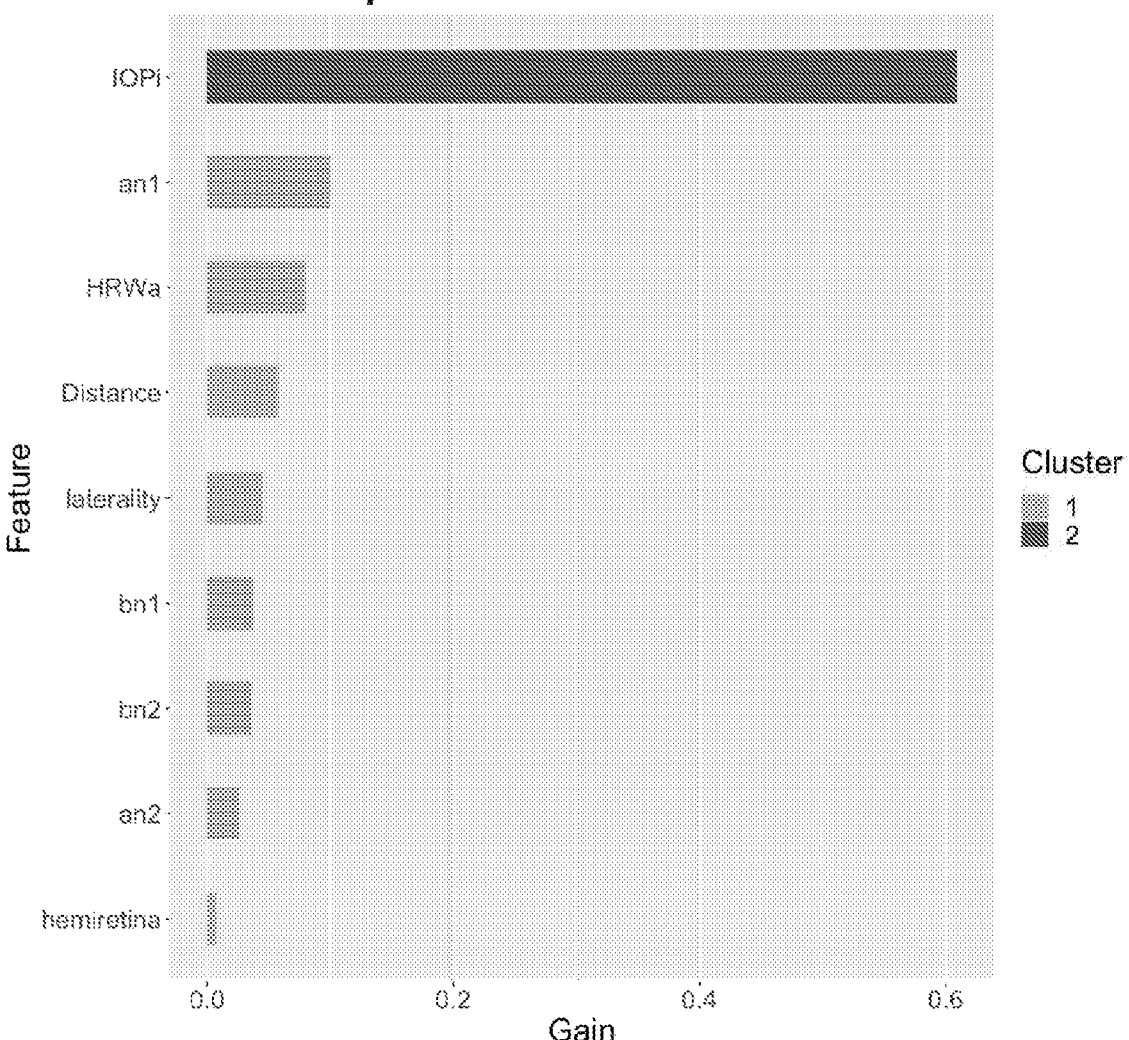
FIG. 9 is an importance plot in respect of the retinal artery.
Figure 10:
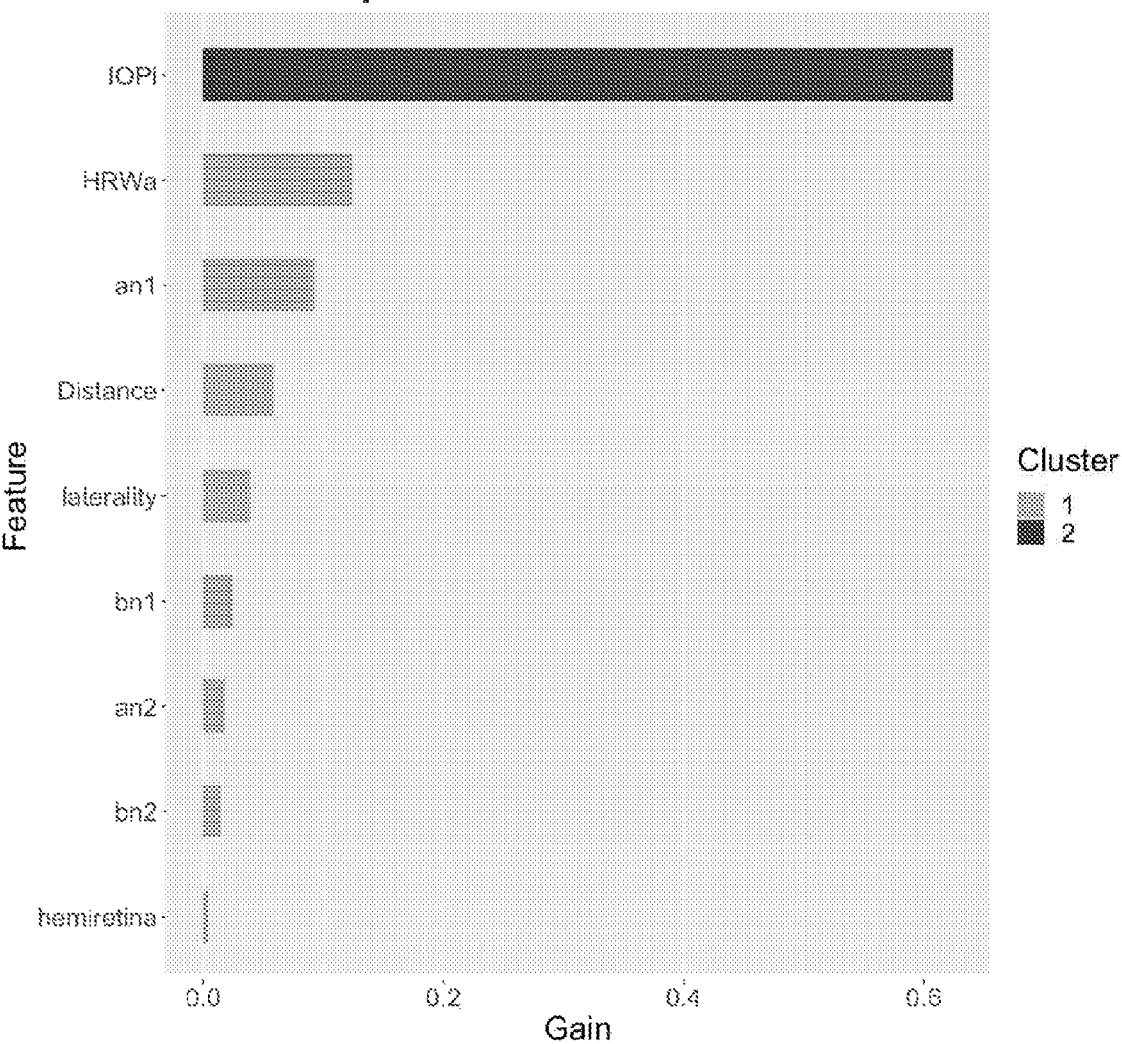
FIG. 10 is an importance plot in respect of the retinal artery.

As discussed by the Applicant with reference to FIGS. 9 and 10 and Table 2, the Applicant has conducted extensive analysis into the feature importance of each feature of the training data set of the models trained with respect to the retinal arteries and retinal veins. The details of this analysis are discussed in the paragraphs that follow however the information relating to the feature importance of the information of the data basis on which the non-invasive determination of the intracranial pressure is obviously highly influential and useful when selecting the data basis. From FIGS. 9 and 10, while the induced intraocular pressure is clearly of primary importance, there are many other features which can significantly influence the determination of intracranial pressure when the data basis includes other information, for instance, the information associated with the frequency components of time-varying signal of the retinal vascular pulsation, and the induced intraocular pressure. On the other hand, the hemiretina appears of lesser importance than laterality, and therefore the hemiretina information may not necessarily be included in the data basis or can be omitted on the understanding that it is likely that its contribution is less influential to the non-invasive intracranial pressure determination. A similar argument can be made when considering the other information such as subject state data.

The data basis for a model trained using the retinal artery data may differ from the data basis for a model trained using the retinal venous data. In a preferred embodiment, the data basis for the non-invasive determination of intracranial pressure for either the model using primarily retinal artery data or primarily retinal venous data, or a combination thereof, can include one or more of the following: induced intraocular pressure ($IOP_i$), a combination of the frequency components (harmonic regression waveform amplitude data ($HRW_a$)), information associated with the frequency components such as at least one coefficient of the frequency components ($a_{n1}$, $b_{n1}$, $a_{n2}$, $b_{n2}$), information on laterality location of the recorded segment of artery or vein of the eye, information on the hemiretina, location of the recorded segment of artery or vein of the eye of the eye, and location of the recorded segment of artery or vein of the eye, i.e. the distance of the recorded segment of artery or vein from the central optic nerve.

In another preferred embodiment, the priority of the importance of the data basis information for use in determination of the intracranial pressure using primarily retinal venous data is as follows: induced intraocular pressure (IOP$_i$), a combination of the frequency components (harmonic regression waveform amplitude data (HRW$_a$)), a$_{n1}$, location of the recorded segment of artery or vein of the eye, i.e. the distance of the recorded segment of artery or vein from the central optic nerve, laterality, b$_{n1}$, a$_{n2}$, b$_{n2}$, hemiretina location of the recorded segment of artery or vein of the eye (see FIG. 10 and Table 2). Thus, the information used in the data basis to determine intracranial pressure from the venous system is preferably selected from the more important features listed in a particular preferred embodiment.

In another preferred embodiment, the priority of the importance of the data basis information for use in determination intracranial pressure using primarily retinal artery data is as follows: induced intraocular pressure (IOP$_i$), a$_{n1}$, laterality, location of the recorded segment of artery or vein of the eye i.e., distance of the recorded segment of artery or vein from the central optic nerve, a combination of the frequency components (harmonic regression waveform amplitude data (HRW$_a$)), b$_{n2}$, b$_{n1}$, a$_{n2}$, hemiretina location of the recorded segment of artery or vein of the eye (see FIG. 9 and Table 2). Thus, the information used in the data basis to determine intracranial pressure from the artery system can include all the listed features, but should limitation of features be required, the features used in the data basis may be preferably selected from the more important features listed.

The identification of the important features that can be selected for use in the data basis for the non-invasive determination of intracranial pressure is one of the advantages of a decision tree model learning process. As discussed in the above paragraphs, the model's ability to provide a ranking score representing the contribution from the selected feature to the model prediction which can provide a measure on the importance of the features. It is calculated for a single decision tree by the amount that each attribute split point improves the performance measure, weighted by the number of observations for which the node is responsible. This informs the selection of the data basis on which the non-invasive determination of intracranial pressure is made, and, as discussed in the following paragraphs, also informs the training data set on which the trained model depends.

Notably, as discussed in a study described in the section USING A LINEAR MODEL TO INTERPRET INTRACRANIAL PRESSURE RESULTS at the end of this disclosure with reference to FIGS. 19 to 26, data from the arterial system has been shown to be surprisingly more accurate in determination of the intracranial pressure via a trained model when compared to using retinal vascular pulsation data from the venous system. In particular, the study discusses the use of a hierarchical linear mixed-effects model to provide interpretative insight into the response of the vascular system to changes in intracranial pressure, which informed the selection of training data set parameters for the machine learning process. The arterial system, being less influenced by high ICP, is expected to be more reliable for use in determining intracranial pressure non-invasively. This is a surprising result as it has been previously understood that either the venous system or a combination of the venous and the arterial system would be most useful in determination of intracranial pressure. Therefore, the determination of the intracranial pressure non-invasively can be conducted on primarily, and preferably, retinal arterial pulsation data. This is validated by the Applicant's work as discussed with reference to Table 5 and FIGS. 16A and 16B in the following paragraphs under the heading of 'Model Validation', which show that the arterial peak density provides the closest estimate of the measured intracranial pressure, which was measured via alternate means such as an invasive method of a lumbar puncture.

So, while retinal vascular pulsation data can be collected for both the veins and the arteries, it is preferred that in an embodiment of the present invention that the method 100 described below is conducted on a data basis or a training data set from at least primarily at least one feature of retinal arterial vascular pulsation data and subject state data which may allow a more accurate ICP prediction non-invasively. Thus, in step 108, the retinal vascular pulsation amplitude data is primarily the retinal arterial pulsation amplitude data. This step 108, of course, may be performed at any step in the process, and its position in this method does not preclude it being performed at any other step in the method.

In the next step 114 of the method, the model is trained to define a relationship between the intracranial pressure and the data basis (discussed above) using a first training data set which has been retrieved in step 110 and used to train a model via a model learning process in step 112 (more details are provided below). A machine learning approach to train the model has the advantage of allowing prediction of the ICP non-invasively, and further, the issues of heteroscedasticity are also addressed. A second model to define a relationship between the intracranial pressure and the retinal venous pulsation data and/or patient state data is then calculated using a second training data set either concurrently or consecutively (steps 110 and 112). The first and second training data sets are directed to arterial and venous systems respectively.

The Applicant's extensive analysis into the feature importance of each feature of the training data set of the models trained with respect to the retinal arteries and retinal veins significantly informs the selection and understanding of the training data sets. From FIGS. 9 and 10 and Table 2, while the induced intraocular pressure is clearly of primary importance, there are many other features which can significantly influence the determination of intracranial pressure. The training data sets include information, for instance, such as at least one or more the coefficients associated with the frequency components of time-varying signal of the retinal vascular pulsation and combination of the coefficients. The retinal vascular system clearly has more influential features that others, i.e., intraocular pressure, and such a system lends itself to use by a decision tree model learning process as the feature importance can be clearly defined and prioritised to allow selection of the more important features when selecting the training data set for training (step 110) either the model of the venous or artery systems. Thus, there may be an intermediate step between steps 110 and 112 which involve selection of the information included in the training data sets especially in view of being informed of the relative importance of that feature information by the analysis conducted by the Applicant.

As an example, the hemiretina location of the recorded segment of artery or vein of the eye appears of lesser importance than laterality, and therefore the hemiretina location information may not necessarily be included in the data basis or can be omitted on the understanding that it is likely that its contribution is less influential to the non-invasive intracranial pressure determination. Similarly, there is an understanding that a sparse or less complete training data set may be nearly as statistically significant in its effect on the accuracy of the non-invasive determination of intracranial pressure depending on the selection of features. Further, as shown in FIGS. 9 and 10, and Table 2, the selection of data in the training data set may differ between models for arterial or venous systems.

Thus, it is generally preferred that a regression model learning process is used to predict the ICP. The applicant found a decision tree regression model had the following advantages to predict the ICP non-invasively using the retinal arterial and venous pulsation data, also described as photoplethysmographic data (mPPG) data. As discussed in the background section above, mPPG data has many analytic challenges including considerable intra- and inter-individual variability of the pulsation amplitude and timing characteristics. In their study, the applicant has found that this machine learning approach, particularly, the decision tree regression model machine learning approach, addresses, at least to some extent, heteroscedasticity, and therefore makes the prediction of ICP more precise. In addition, compared to other learning model algorithms, decision tree regression model machine learning approach requires less effort for data preparation during pre-processing. Vascular pulsation data is non-normal, this imposes limitations with the choice of statistical analyses using hypothesis testing and regression methods, however, a decision tree approach advantageously requires neither data normalization nor scaling.

This means not only is there less work in preparing data for determining ICP, but that there is more likelihood that the process will run smoothly. Other machine learning approaches have been known not to be able to run at all unless the data has been pre-processed to a certain quality. Less requirements on pre-processing can mean that a more complete training data set. Pre-processing of data usually involves identification of missing values with subsequent data exclusion or imputation, with decision tree algorithms missing values do not affect the process of building a decision tree. This further increases the precision of the determination of ICP with the decision tree model learning approach. The preferred decision tree model learning algorithm used is the XGB algorithm.

The applicant has previously attempted to determine intracranial pressure using other model learning processes, such as neural networks. However, the data processing required to generate the model was extensive and required too much processing power resulting in long processing times. For example, the XGB data processing takes only a few seconds compared to the 24 hours required for processing using neural networks. Furthermore, data scaling and normalization is not required using the present method which can take up time and require additional data processing. Data scaling and normalization can be required with other model learning processes.

Statistical Analysis

The training set consisted of 85% of the total vascular pulsation points, and 15% of the data-points were utilised for the test set. Where appropriate the mean and standard deviation was used as a measure of central tendency. The distribution of the $HRW_a$ and the majority of the Fourier coefficients were non-normal, therefore the median was used as a measure of central tendency and the interquartile range (IQR) was used to assess dispersion of this measure. The range, minimum, and maximum of these parameters were also computed. Heteroscedasticity was shown in the multifactorial. Homogeneity of variance test using the Levene test $p < 0{:}0001$. The Kruskal-Wallis test was used in the hypothesis test of the differences in the medians, and the paired Wilcoxon test with Bonferroni-Holm correction was used for post-hoc analysis. Model fit was assessed using $R^2$ square, which is a comparison of residual sum of squares (SSres) with total sum of squares (SStot). Model Prediction accuracy was estimated by calculating the Mean Squared Error (MSE), defined as the square of the difference between the predicted and actual values of the test set, it assigns more weight to larger errors. Root mean square error (RMSE), which is the standard deviation of the residuals (prediction errors), the higher the number the greater the standard deviation $\sigma$ of the distribution of errors. MSE and RMSE are used to evaluate the influence of outliers on predictions. The mean absolute error (MAE) calculated by the magnitude average difference between the predicted and actual values of the test set.

Figure 11:
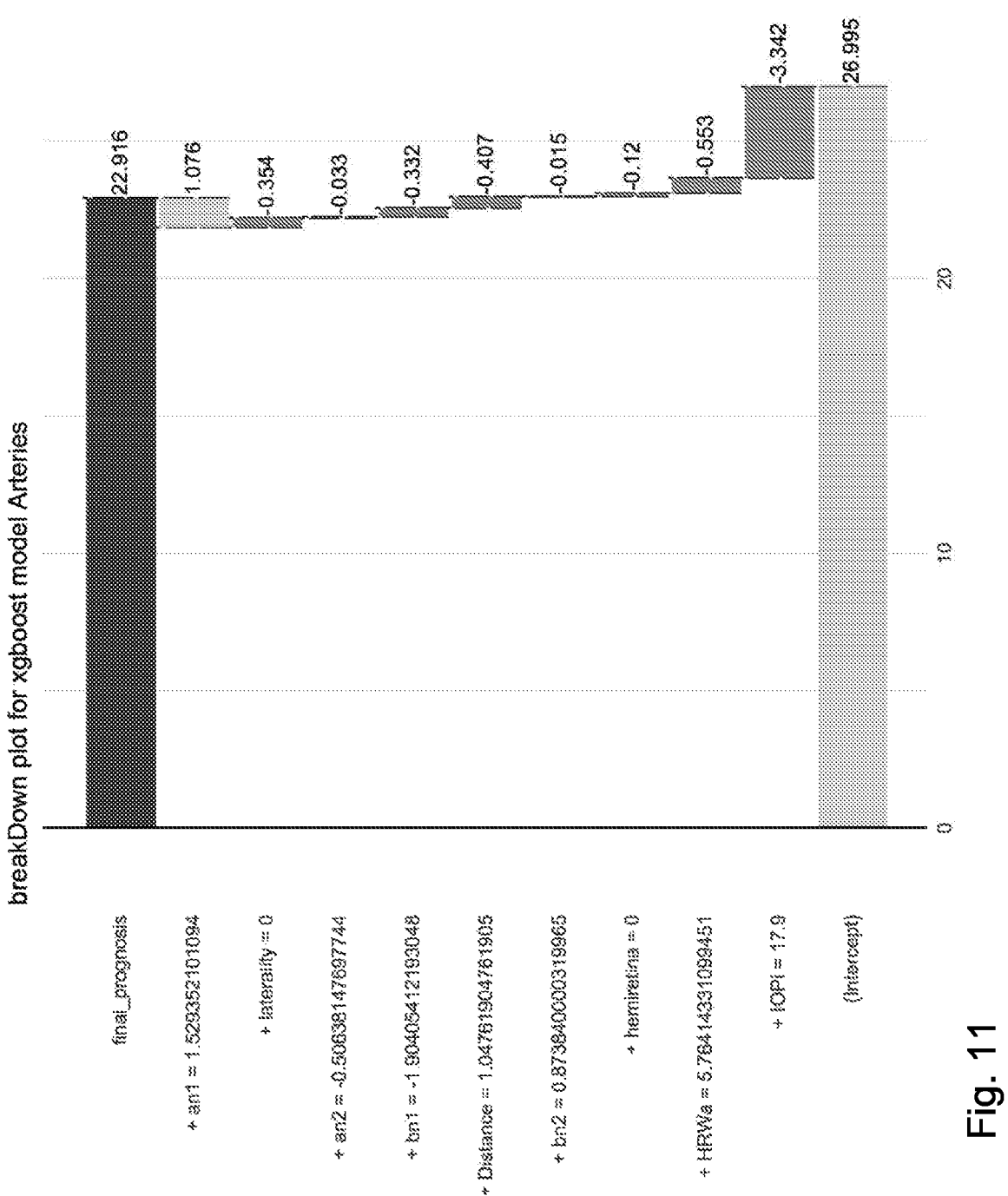
FIG. 11 is a breakdown plot of the retinal artery for XGBoost.
Figure 12:
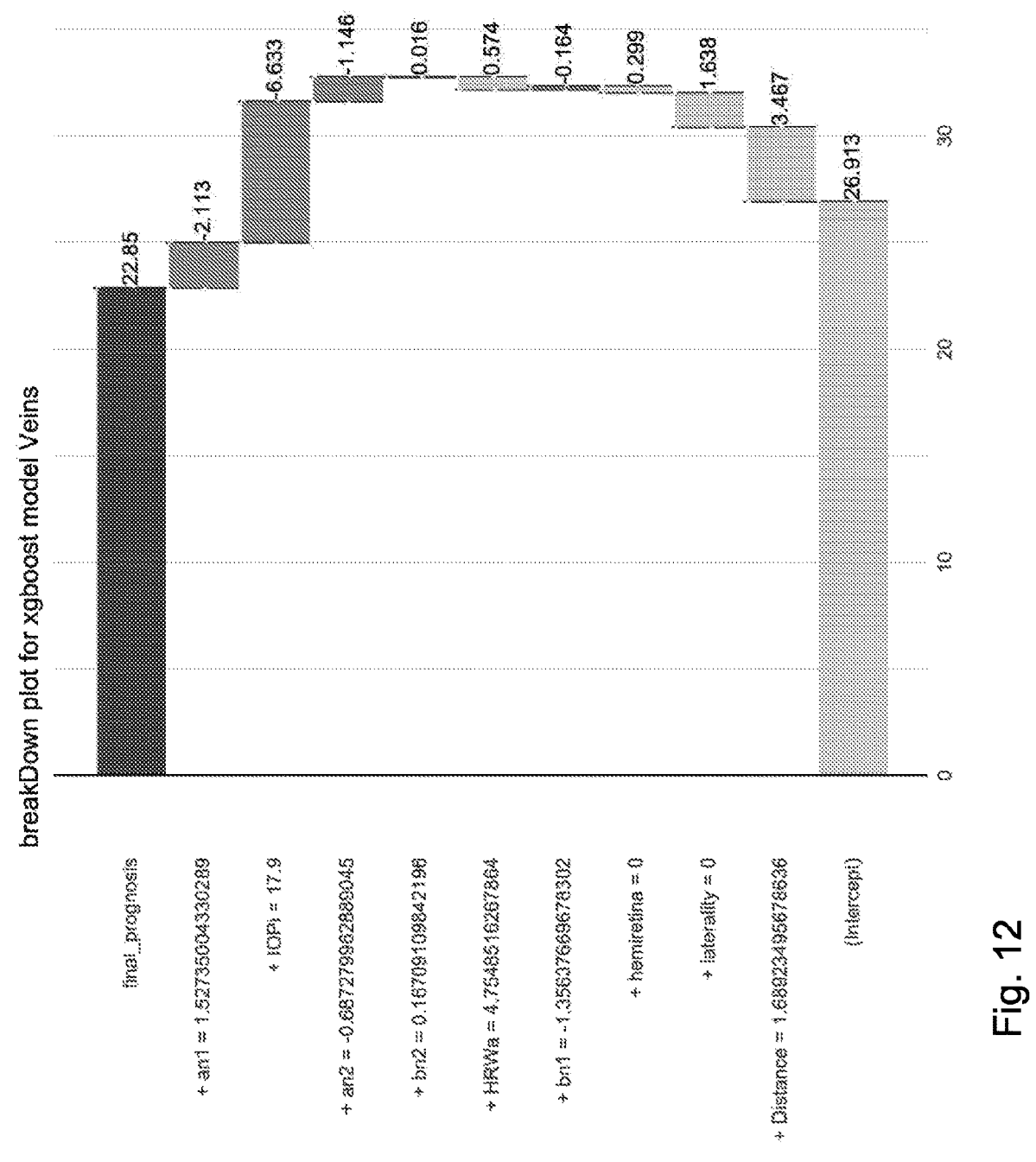
FIG. 12 is a breakdown plot of the retinal vein for XGBoost.

In the preferred embodiment, feature importance is calculated from the gain on each decision tree node, which represents the contribution from the selected feature. Importance provides a ranking score that indicates how valuable each feature was in the construction of the boosted decision trees within the model. The more an attribute is used to make key decisions with decision trees, the higher its relative importance. Importance is calculated for a single decision tree by the amount that each attribute split point improves the performance measure, weighted by the number of observations for which the node is responsible. There are three options for measuring feature importance in XGBoost, weight, which is the number of times a feature is used to split the data across all trees. Cover is the number of times a feature is used to split the data across all trees weighted by the number of training data points that go through those splits, and gain is the average training loss gained when using a feature for splitting. Breakdown plots were used to estimate the contribution of an explanatory variable to the model's prediction by computing the shift in the expected value of (y), while fixing the values of other variables (FIGS. 11 and 12). In this plot explanatory variables can have a positive or a negative contribution with respect to the mean model prediction. SHapley Additive exPlanations (SHAP) values were computed (details provided in the following paragraphs), these reverse engineer the output of a predictive algorithm by quantifying the contribution each feature offers to the prediction made by the model. It differs from other methods of interpretation in that its output concerns local rather than global interpretation. It is based on the game theoretically optimal, which calculates the importance of a feature by comparing what a model predicts with and without the feature.

The validation set consisted of seven cases, mean and median and peak density of the predicted ICP were compared to the measured ICP. The peak density was measured from the density plot, which uses a kernel density estimate to plot the probability density function of the predicted ICP. The bandwidth of the plot determines the smoothing function, the higher the bandwidth the more the plot smoothing effect. The peak density represents the highest count of the predicted ICP values in the distribution. Bland-Altman plots were generated and t-tests were used to measure agreement between measured and the mean and peak density of the estimated ICP for both the arteries and the veins.

Study Results

There were a total twenty females (95.2%) and one male (4.8%) in the study population. The age demonstrated a bimodal distribution with a mean of 32 years (sd 8.32, range 17-47 years). The median ICP the $ICP_n$ group was 18.50 cm water (min 9.50, max=24, IQR=6), the corresponding values in $ICP_h$ group was 31 cm water (min 25.50, max=68, IQR=10). Descriptive statistical parameters of the Fourier waves of both groups are shown in Table 1. Within ICP group differences represented the differences between the $HRW_a$ and the Fourier coefficients compared by vessel type, which achieved statistical significance (p<0.0001) for all except the $b_{n2}$ in the $ICP_h$ group. Between ICP group differences represented differences of between the $HRW_a$ and the Fourier coefficients in a single vascular system classified by ICP, this achieved statistical significance (p<0.001) for all except the retinal venous $b_{n1}$, and arterial $a_{n2}$ coefficients.

TABLE 1

| Parameter | Site | Median | IQR | Min | Max | Range |
|---|---|---|---|---|---|---|
| $ICP_h$ | | | | | | |
| $HRW_a$ | Vein | 4.743 | 3.875 | 0.62 | 11.983 | 11.363 |
| $b_{n1}$ | Vein | $-1.418^b$ | 1.268 | -5.6 | 5.081 | 10.681 |
| $a_{n1}$ | Vein | 1.079 | 2.507 | -5.519 | 5.755 | 11.274 |
| $b_{n2}$ | Vein | $0.114^w$ | 0.594 | -3.723 | 2.525 | 6.249 |
| $a_{n2}$ | Vein | -0.132 | .684 | -2.703 | 2.881 | 5.585 |
| $HRW_a$ | Artery | 4.559 | 2.958 | 0.665 | 9.983 | 9.317 |
| $b_{n1}$ | Artery | -1.385 | 1.047 | -4.659 | 4.096 | 8.755 |
| $a_{n1}$ | Artery | 0.896 | 2.381 | -4.568 | 4.485 | 9.054 |
| $b_{n2}$ | Artery | $0.111^w$ | 0.655 | -2.572 | 2.606 | 5.178 |
| $a_{n2}$ | Artery | $-0.110^b$ | 0.691 | -2.169 | 2.217 | 4.386 |
| $ICP_n$ | | | | | | |
| $HRW_a$ | Vein | 5.314 | 4.218 | 0.695 | 14.434 | 13.739 |
| $b_{n1}$ | Vein | $-1.646^b$ | 1.511 | -6.988 | 5.148 | 12.137 |
| $a_{n1}$ | Vein | 1.087 | 2.675 | -5.162 | 6.727 | 11.89 |
| $b_{n2}$ | Vein | 0.15 | 0.598 | -3.741 | 3.417 | 7.158 |
| $a_{n2}$ | Vein | -0.173 | 0.735 | -3.07 | 2.702 | 5.772 |
| $HRW_a$ | Artery | 4.139 | 2.712 | 0.75 | 9.233 | 8.483 |
| $b_{n1}$ | Artery | -1.276 | 1.048 | -4.432 | 3.843 | 8.275 |
| $a_{n1}$ | Artery | 0.64 | 2.148 | -3.824 | 4.103 | 8.027 |
| $b_{n2}$ | Artery | 0.093 | 0.545 | -2.291 | 2.248 | 4.539 |
| $a_{n2}$ | Artery | $-0.086^b$ | 0.663 | -2.172 | 2.133 | 4.305 |

Table 1 is a summary of the descriptive statistics for the high intracranial pressure ($ICP_h$) and normal intracranial pressure ($ICP_n$) groups. $HRW_a$=harmonic regression wave amplitude. $a_{n1,}2$=first and second cosine coefficient, $b_{n1,}$ 2=first and second sine coefficients. Min=minimum, Max=maximum. Superscripts denote that statistical significance was not achieved for within([w]), and between[b] group differences.

Figure 6A:
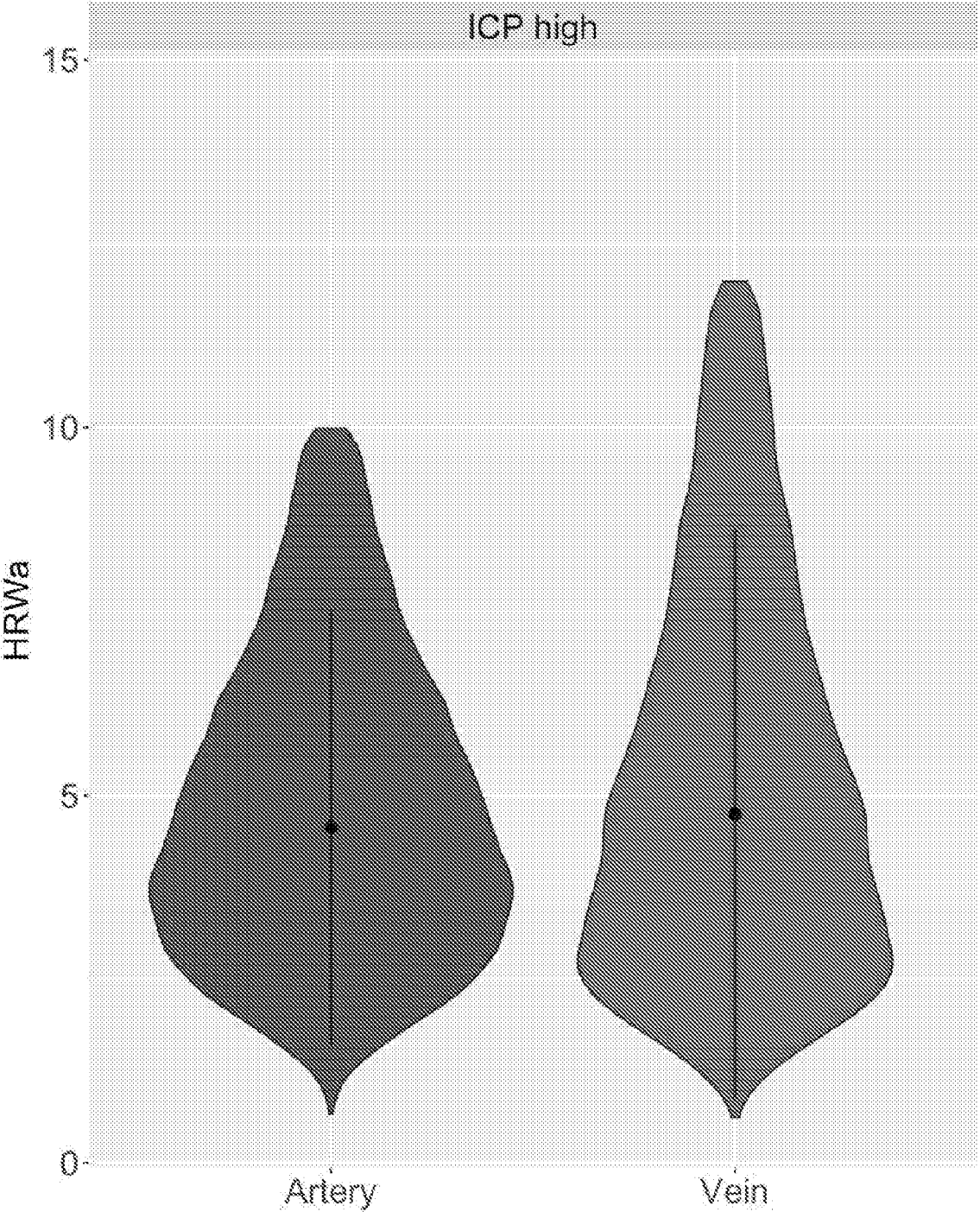
FIG. 6 shows violin plots of the distribution of $HRW_a$ with respect to normal ICP and high ICP.
Figure 6B:
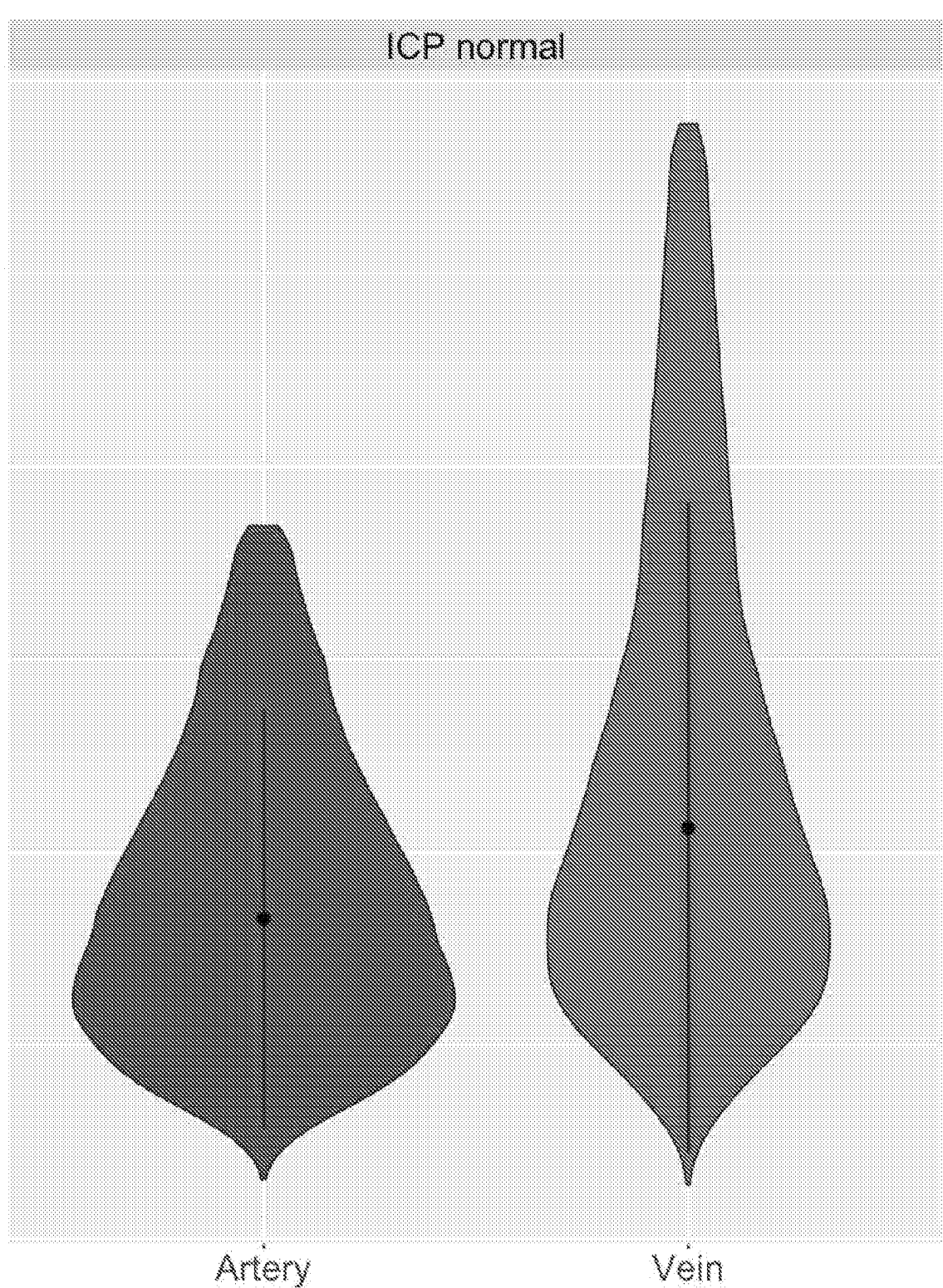
Figure 7A:
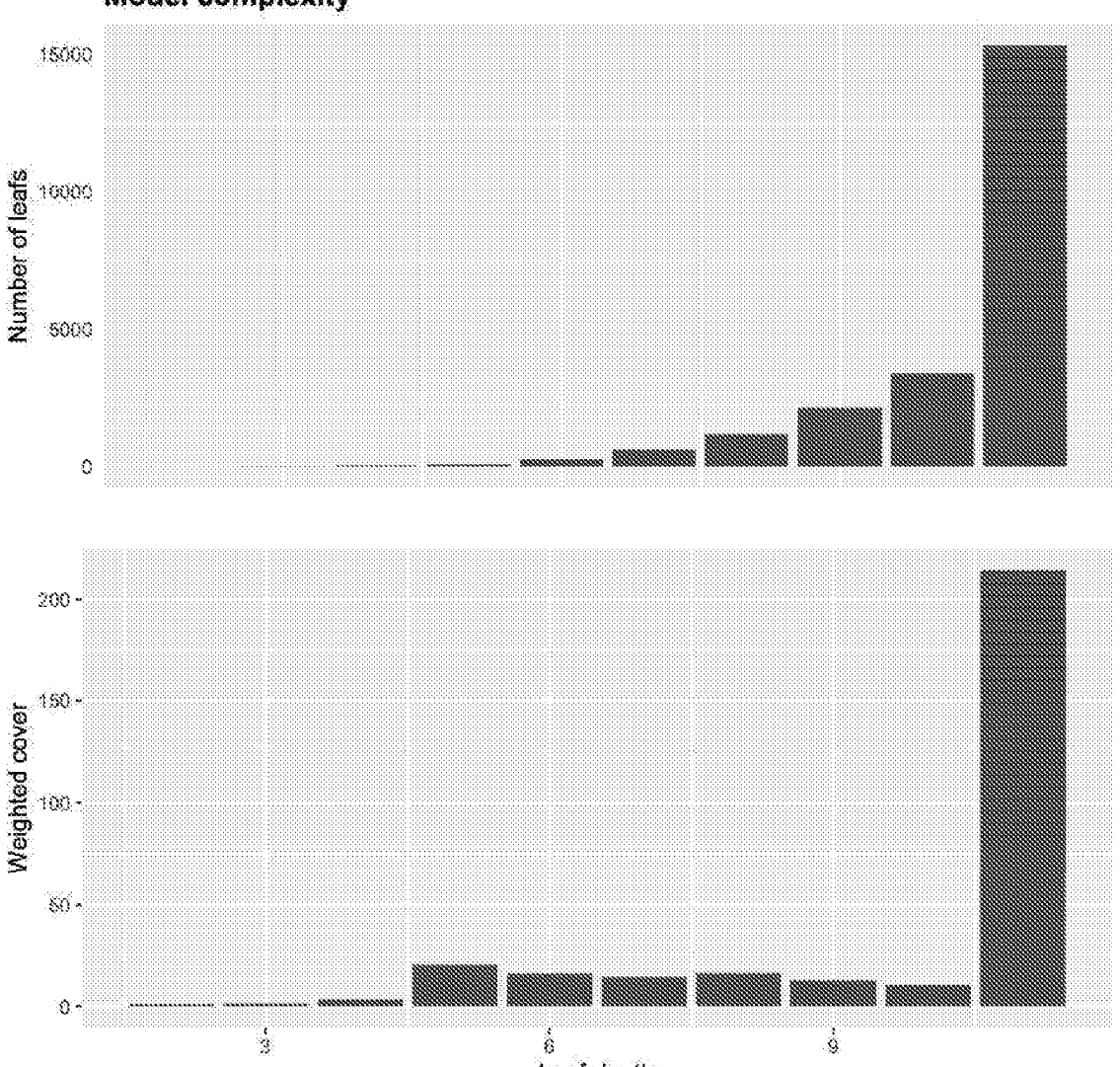
FIG. 7A shows a graph of retinal arterial model complexity.
Figure 7B:
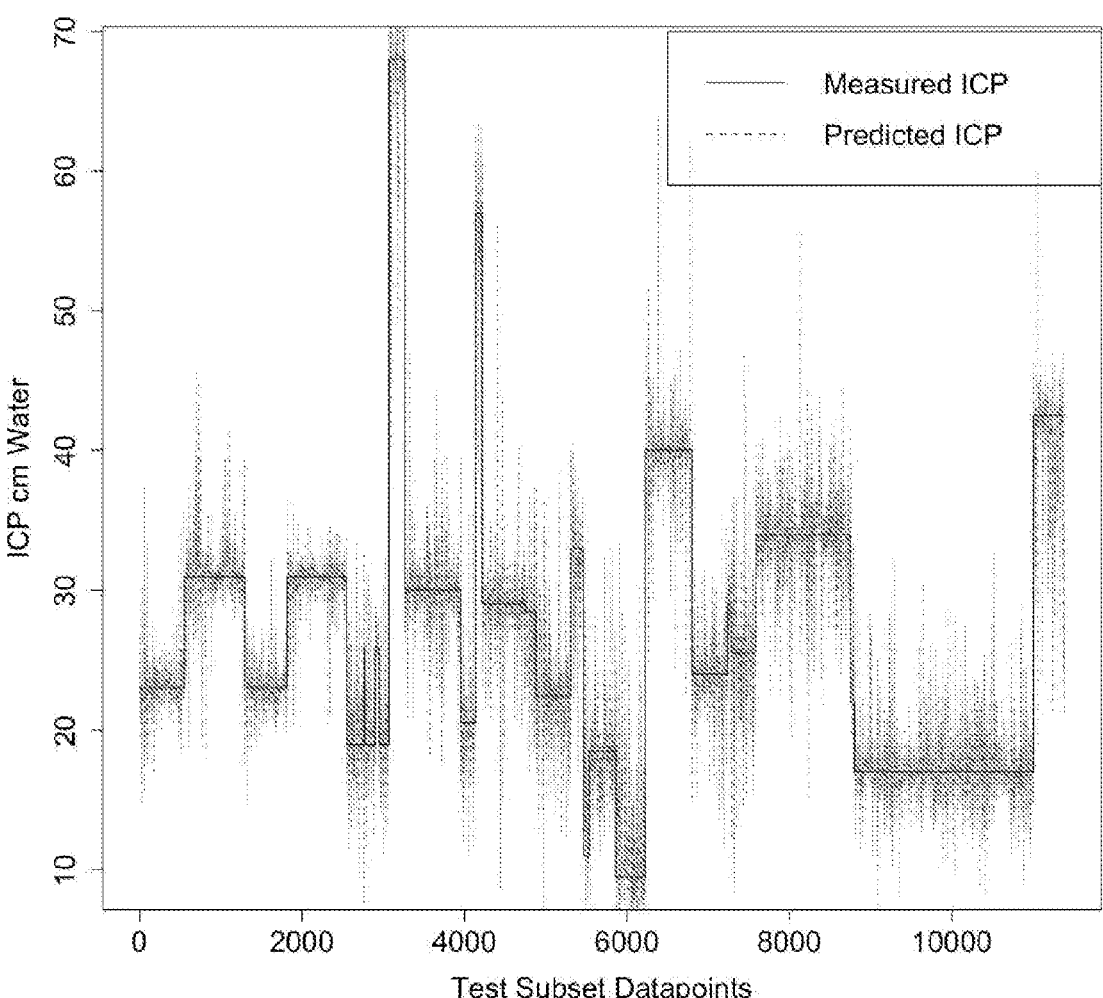
FIG. 7B shows the extreme gradient boost model first of the retinal arteries.
Figure 8A:
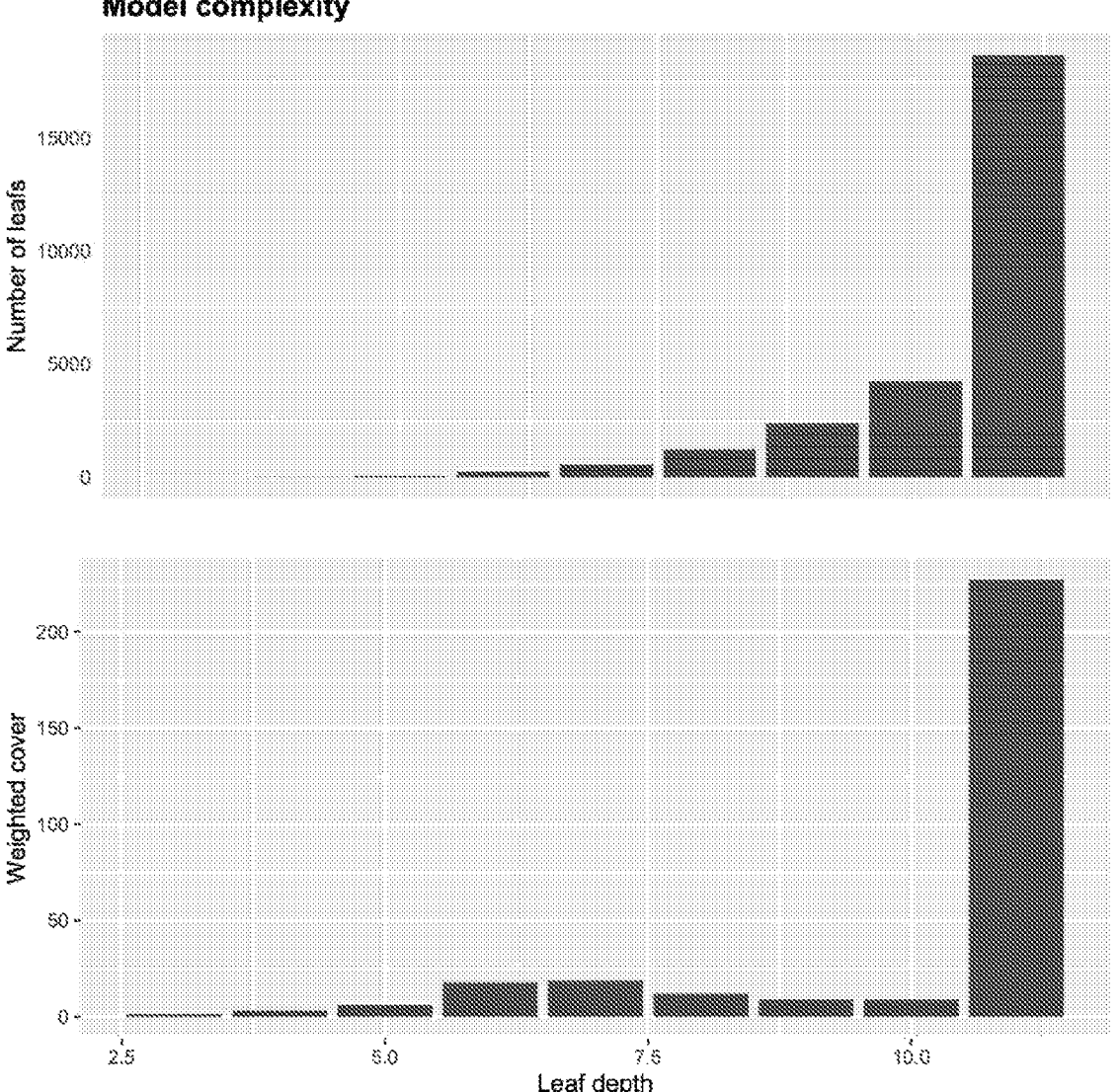
FIG. 8A shows a graph of retinal venous model complexity.
Figure 8B:
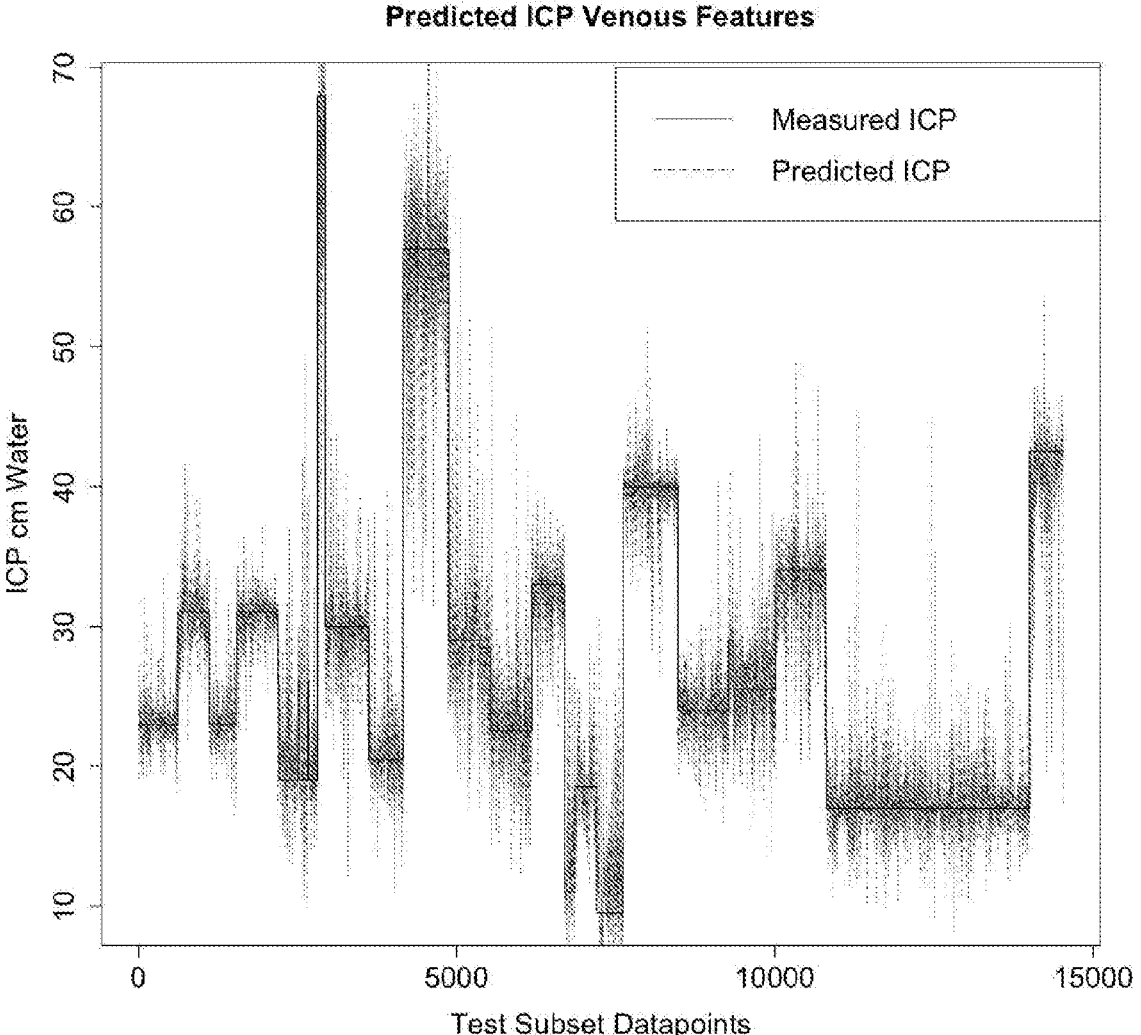
FIG. 8B shows the extreme gradient boost model first of the retinal veins.

It can be noted that there was a reduction of the median retinal venous pulsation amplitude in the $ICP_h$ group, FIG. 6 are violin plots of the harmonic regression wave amplitude for the arterial, venous and in the high ICP and normal ICP groups, and which demonstrates an increase in the median arterial pulse amplitude compared to the $ICP_n$ cases. The central marker in the violin plots indicate the median and interquartile range. The reduction of the difference in maximum and median retinal vascular pulsation amplitudes within the ICP groups is a consequence of a reduction of the venous and increase in the arterial pulsation amplitudes within the $ICP_h$ group.

Machine Learning Model Training Data Set

Model complexity and fit of the arterial and venous models is demonstrated in (FIGS. 7A to 8B) respectively, where the weighted cover in the image represents the distribution of average weighted number of residuals ending up in leafs at certain depth of the decision tree model. Whereas the venous model was composed of a total of 2,972 nodes, 2,968 edges and 54,766 leaves, the arterial model consisted of a total of 2,552 nodes, 2,548 edges and 46,126 leaves. The model fit was better for the arteries than the veins as indicated by an R2=0.96 and R2=0.95 respectively. Additionally, the arterial model demonstrated higher accuracy parameters (MSE=3.5, MAE=1.01, RSME=1.87) compared to the venous model (MSE=6.5, MAE=1.25, RSME=2.56). Thus advantageously, in the preferred embodiments, the retinal arterial pulsation data may preferably be used over the venous pulsation data because of the superior model fit and higher accuracy parameters. Also, advantageously, the retinal pulsation data can be modelled for the venous and arterial systems separately to provide a measurement of accuracy of the non-invasive intracranial pressure determination.

In steps 110 and 112 of the method discussed in FIG. 2, training data sets are used to train the executed model learning process i.e. to determine the model parameters of this machine learning process separately for the arterial and venous systems. The first training data set relating to the retinal arterial vascular data is used to determine the relationship between the intracranial pressure and data basis of the arterial system, and a second training data set is used to determine the relationship between the intracranial pressure and data basis of the venous system. In an embodiment, appropriate processing of the training data set can be conducted so as to improve the accuracy of the training data. The parameters used in the training data sets are induced intraocular pressure $IOP_i$, $HRW_a$, the four frequency components ($a_{n1}$, $a_{n2}$, $b_{n,1}$, $b_{n,2}$), laterality, hemiretina, measured ICP (for example by lumbar puncture) and distance of the recorded segment of artery or vein from the central optic nerve. FIGS. 9 and 10 show the feature importance of the retinal arteries and veins, summarised in Table 2. From this, at least one parameter, i.e. the induced ocular pressure, can be used, as it is the most important of the features. However, at least one or more of the other features may also be used for greater accuracy, such as $HRW_a$, the four frequency components ($a_{n1}$, $a_{n2}$, $b_{n,1}$, $b_{n,2}$), laterality, hemiretina, distance of the recorded segment of artery or vein from the central optic nerve, and a previous measurement of ICP (taken for example by lumbar puncture).

Global feature importance (FIG. 9, FIG. 10) ranks the nine features, i.e. the 9 main parameters used in the two training data sets to predict ICP, whereas for the venous model $IOP_i$, $HRW_a$, and $a_{n1}$ had the highest importance for the XGB predictor, for the arterial model these were $IOP_i$, $a_{n1}$ and laterality. When feature weights were considered $IOP_i$, $a_{n1}$ and $HRW_a$ dominated the feature importance of both models, altogether accounting for approximately 25% of the model's feature importance (see Table 2).

TABLE 2

| Feature Arterial Model | Gain | Cover | Weight | Feature Venous Model | Gain | Cover | Weight |
|---|---|---|---|---|---|---|---|
| $IOP_i$ | 0.727 | 0.585 | 0.221 | $IOP_i$ | 0.624 | 0.0598 | 0.217 |
| $a_{n1}$ | 0.076 | 0.053 | 0.121 | $a_{n1}$ | 0.092 | 0.072 | 0.119 |

TABLE 2-continued

| Feature Arterial Model | Gain | Cover | Weight | Feature Venous Model | Gain | Cover | Weight |
|---|---|---|---|---|---|---|---|
| Laterality | 0.055 | 0.012 | 0.025 | Laterality | 0.039 | 0.014 | 0.024 |
| Distance | 0.045 | 0.127 | 0.149 | Distance | 0.059 | 0.098 | 0.144 |
| $HRW_a$ | 0.033 | 0.057 | 0.186 | $HRW_a$ | 0.124 | 0.069 | 0.197 |
| $b_{n2}$ | 0.023 | 0.059 | 0.104 | $b_{n2}$ | 0.024 | 0.051 | 0.097 |
| $a_{n2}$ | 0.019 | 0.052 | 0.087 | $a_{n2}$ | 0.018 | 0.053 | 0.093 |
| $b_{n1}$ | 0.019 | 0.043 | 0.085 | $b_{n1}$ | 0.014 | 0.037 | 0.090 |
| Hemiretina | 0.003 | 0.011 | 0.021 | Hemiretina | 0.004 | 0.008 | 0.019 |

Table 2 shows the feature/parameter importance of training data sets used in the machine learning models. Model weight represents the ratio of the number of times a feature is used to split the data across the whole tree, this parameter indicates that $IOP_i$, $a_{n1}$ and $HRW_a$ dominated the feature importance of both models. The model gain is the difference between the calculated similarity scores for successive leafs in the decision tree, it represents the average training loss gained when using a feature for further branching. Cover is the number of times a feature is used to split the data across all trees weighted by the number of training data points that go through those splits.

Feature/Parameter importance of each training data set for the venous and arterial models are demonstrated graphically in FIG. 9 and FIG. 10. Breakdown plots demonstrate the direction of shift of the mean prediction by the feature of interest, which signifies model behaviour rather than real world interpretation of the physiologic behaviour of the features (see FIGS. 11 and 12). In both plots, XGB requires converting factors to numerical values: hemiretina (0)=inferior retina, laterality (0)=Left side. The underlying intuition is to capture the contribution of an explanatory variable to the model's prediction by computing the shift in the expected value of the predicted variable, while fixing the values of other variables. These demonstrate the positive and negative contributions of the features to the model. The intercept sets the model baseline, which is the average model prediction, and the final prognosis takes into account the intercept and the model features. For the arterial model the $a_{n1}$ is the only feature that showed a positive contribution to the mean model prediction. The venous model showed that only the $HRW_a$ and the $b_{n2}$ shift the mean prediction in the positive direction among the components of the Fourier equation in the model (Table 3).

TABLE 3

| | Value Arterial Model | Contribution | Value Venous Model | Contribution |
|---|---|---|---|---|
| (Intercept) | | 26.988 | | 26.926 |
| IOPi | 17.900 | −3.343 | 17.900 | −6.632 |
| $HRW_a$ | 5.764 | −0.546 | 4.755 | 0.584 |
| Hemiretina | 0 | 0.123 | 0 | 0.300 |
| $b_{n2}$ | 0.874 | −0.015 | 0.167 | 0.011 |
| Distance | 1.048 | −0.404 | 1.689 | 3.465 |
| $b_{n1}$ | −1.904 | −0.329 | −1.356 | −0.166 |
| $a_{n2}$ | −0.506 | −0.029 | −0.687 | −1.151 |
| Laterality | 0 | −0.354 | 0 | 1.625 |
| $a_{n1}$ | 1.529 | 1.071 | 1.527 | −2.111 |
| Final prognosis | | 22.916 | | 22.850 |
| baseline | 0 | | 0 | |

Table 3 shows the breakdown plot parameters. Breakdown plots (FIGS. 11 and 12) display how contributions attributed to individual explanatory variables change the mean model's prediction to yield the actual prediction for a particular single observation. The plots offer a summary of the effects of particular explanatory variables on a model's prediction.

Mean SHAP Values

Figure 14:
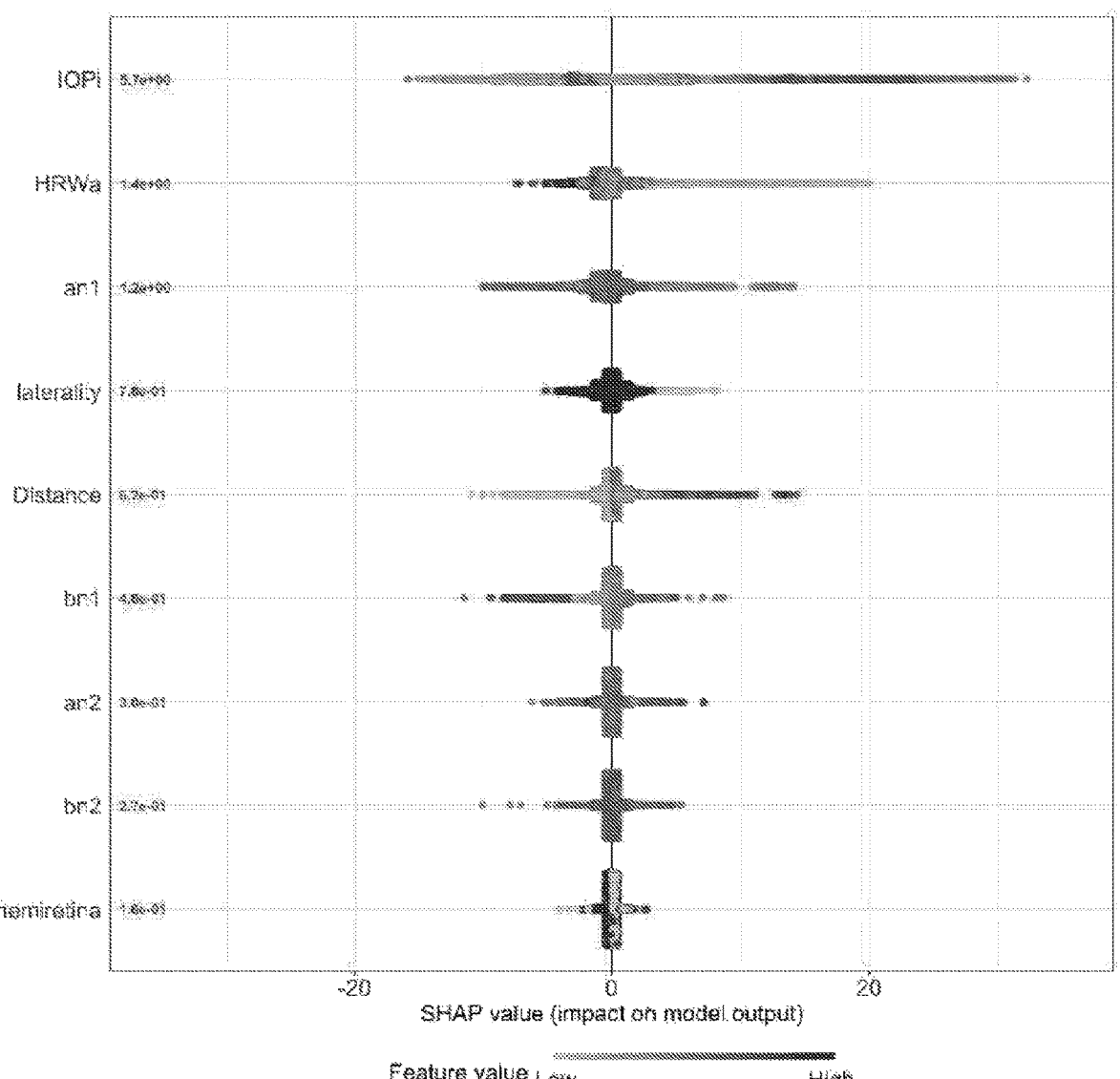
FIG. 14 is the SHAP plot of the retinal vein.
Figure 15A:
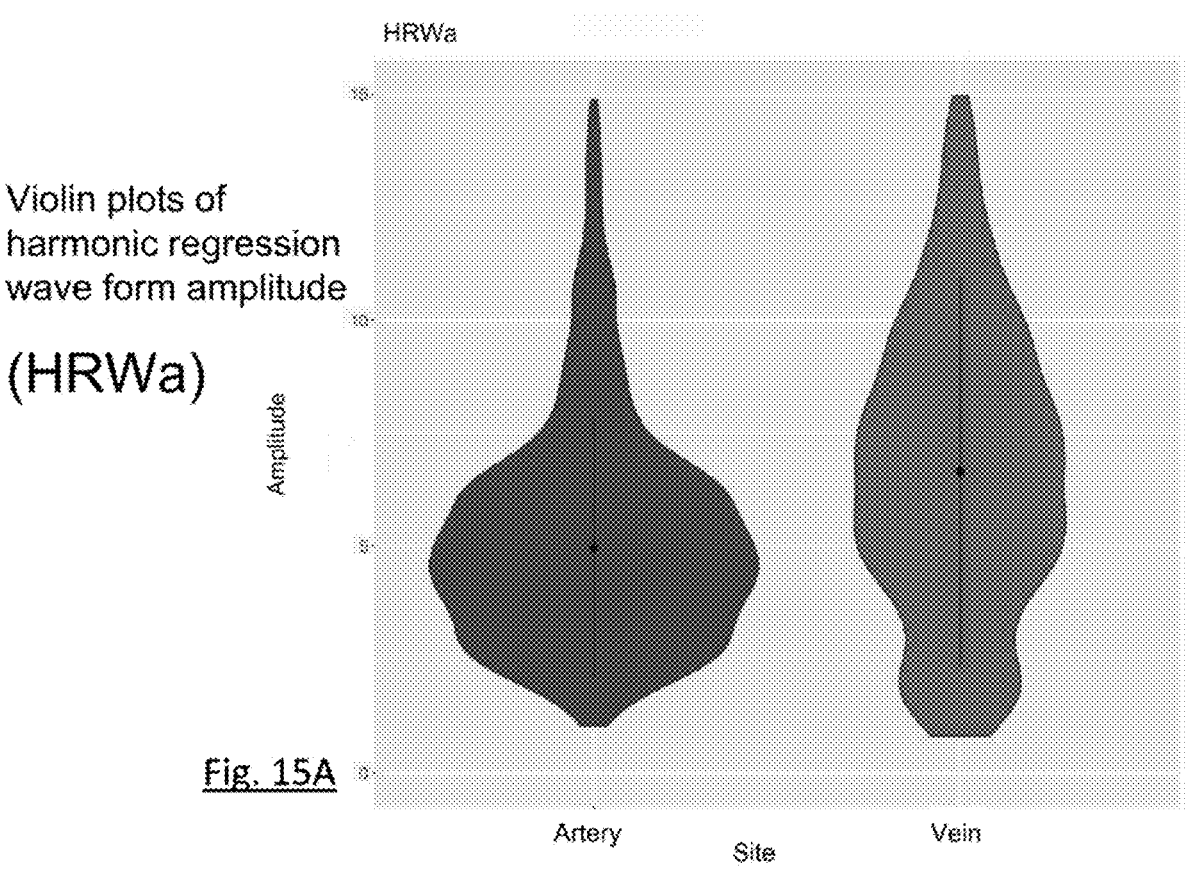
FIG. 15A shows the violin plots of the distribution of harmonic regression waveform amplitude ($HRW_a$).
Figure 15B:
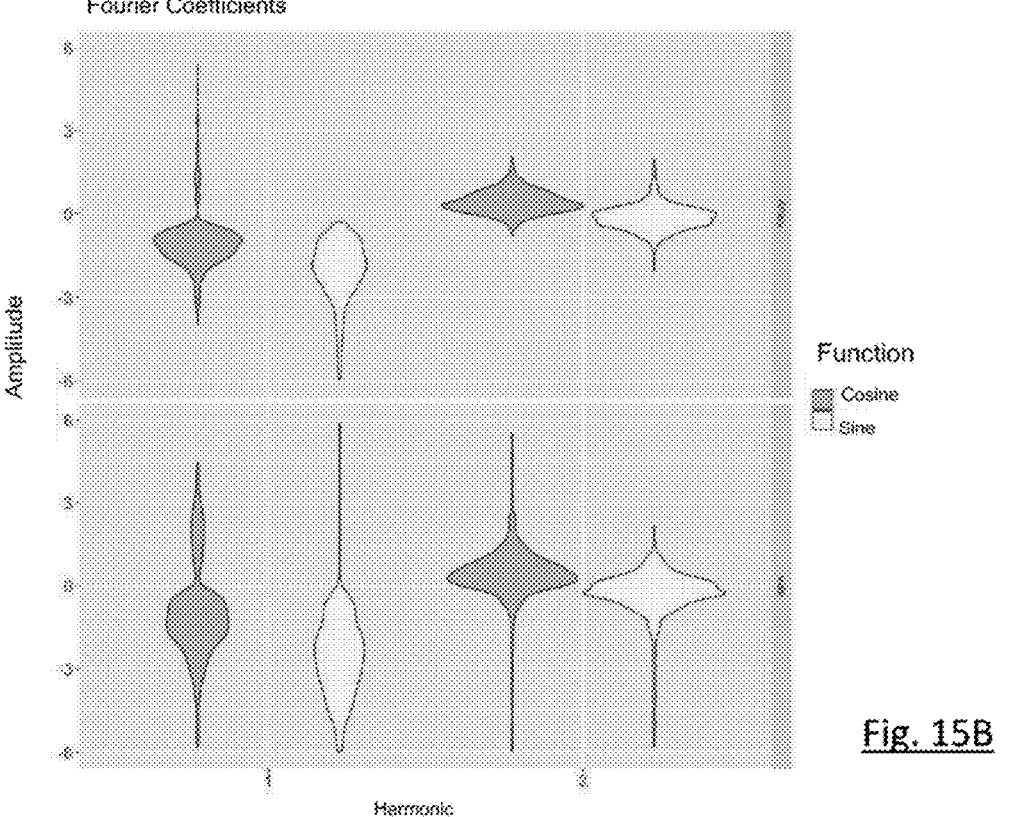
FIG. 15B shows the violin plots of the distribution of Fourier coefficients of the harmonic regression waveform amplitude ($HRW_a$).

The SHAP summary plot combines feature importance with feature effects in FIGS. 14 and 15. The features are ordered according to their importance in the prediction of ICP from each vascular model. SHAP measures the impact of variables taking into account the interaction with other variables of the model. This is accomplished by calculating the importance of a feature by comparing what a model predicts with and without the feature in every possible combination. The position on the y-axis is determined by the feature and on the x-axis by the SHAP value, which indicates the change in model output in log-odds. The colour represents the original value of the feature from low to high, where every point represents a row from the original dataset. Overlapping points are jittered in the y-axis direction (FIG. 14 and FIG. 15). From both plots, it can be observed that the impact of $IOP_i$ on the model prediction depends on the value, i.e. low $IOP_i$ values had no discriminatory power in predicting ICP, and high $IOP_i$ values were required to generate accurate predictions. This feature also showed higher dispersion of the data points than any other of the tested features. Whereas the hemiretinal location of the tested vessel did not show any influence on the model ICP predictability, there was a higher impact on the model from vascular pulsations from the left eye compared to the right. Pulsation values obtained from vascular points in proximity to the optic disc were more favourable in terms of predictive value as were lower HRWa data points. Other than $a_{n1}$, the other Fourier coefficients had a low impact on the model predictability. Mean SHAP values are listed in Table 4, where IOPi demonstrates the highest mean SHAP values in both vascular models (arterial=5.331 and venous=5.723), this was approximately four times the mean value of and (arterial=1.174 and venous=1.196) and the others among the three most significant features (arterial laterality=1.161, venous HRWa=1.43).

TABLE 4

| Feature | Mean Shap Value Arterial Model | Mean Shap Value Venous Model |
|---|---|---|
| $IOP_i$ | 5.3307340 | 5.7227394 |
| $a_{n1}$ | 1.1743062 | 1.1961696 |
| Laterality | 1.1617681 | 0.7563101 |
| Distance | 0.4341689 | 0.6204986 |
| $HRW_a$ | 0.3517103 | 1.4250308 |
| $b_{n2}$ | 0.2603140 | 0.2696922 |
| $b_{n1}$ | 0.2566837 | 0.4626346 |
| $a_{n2}$ | 0.1977119 | 0.3004885 |
| Hemiretina | 0.1098916 | 0.1621388 |

Figure 13:
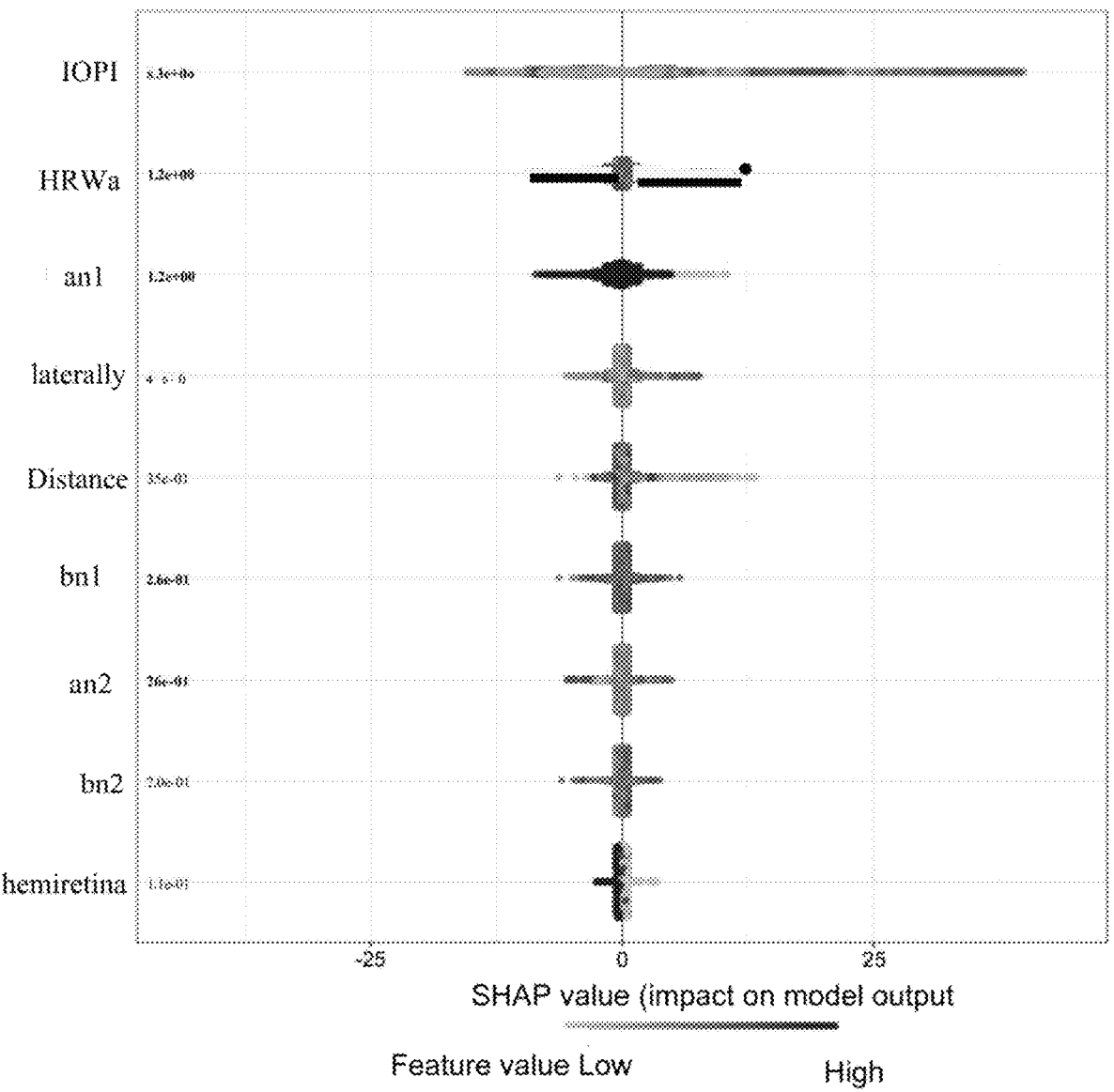
FIG. 13 is the SHAP plot of the retinal artery.

Table 4 shows the Mean SHAP values for the arterial and venous models. SHAP values are based on a game theoretic approach to estimate the contribution of a feature to the model's prediction by considering all possible combinations of the feature to the outcome in what is called a power set. The summary plot combines feature importance with feature effects (FIG. 12 and FIG. 13). Each point on the summary plot is a SHAP value for a feature and an instance. The position on the y-axis is determined by the feature and on the x-axis by the SHAP value. The colour represents the value of the feature from low to high. Overlapping points are jittered in y-axis direction. The features are ordered according to their importance for each model. All effects describe the behaviour of the model and are not necessarily physiologically causal.

After executing the learning model process in step 112, the trained model can be retrieved which has been trained to define the relationship between the intracranial pressure and training data set as discussed in detail above (step 114). By applying the trained model (step 116), the intracranial pressure can be determined non-invasively from a basis which includes retinal vascular pulsation amplitude data in the form of information associated with the frequency components (step 118). Advantageously the Applicant, by use of a validation data set, discussed below, which is different to the training data sets, that the intracranial pressure can be predicted non-invasively and more precisely than previously known methods. The applicant has shown that this method and system of the embodiments of the present invention thereby allow accurate predictions of the intracranial pressure by addressing the disadvantages discussed in the background section above, including that of heteroscedasticity.

Model Validation

In an even more preferred embodiment, the trained model is validated via a validation data set. The validation set consisted of seven cases, all cases underwent lumbar puncture and none of the data in these cases were used to test or train the model as summarised in Table 5.

TABLE 5

| | | Mean Predicted ICP (se) | | Predicted ICP Peak Density | |
| | Measured | | | | |
| Case | ICP | Arterial | Venous | Arterial | Venous |
|---|---|---|---|---|---|
| Case-1 | 22 | 25.79 (0.11) | 26.45 (0.16) | 25.38 | 26.94 |
| Case-2 | 32 | 25.01 (0.41) | 28.87 (0.22) | 27.38 | 27.00 |
| Case-3 | 20 | 22.97 (0.24) | 23.39 (0.16) | 20.06 | 24.61 |
| Case-4 | 32 | 29.82 (0.25) | 31.15 (0.25) | 28.43 | 30.16 |
| Case-5 | 17 | 21.86 (0.18) | 20.56 (0.12) | 23.57 | 20.33 |
| Case-6 | 27 | 31.97 (0.37) | 25.73 (0.12) | 28.36 | 24.01 |
| Case-7 | 26 | 27.82 (0.51) | 22.41 (0.21) | 22.71 | 19.01 |

Violin plots (FIGS. 15A and 15B) show the distribution of the retinal vascular $HRW_a$ and coefficients respectively. Mean and median and peak density of the predicted ICP were compared to the measured ICP. The peak density was measured from the density plot, which uses a kernel density estimate to plot the probability density function of the predicted ICP (FIGS. 16A and 16B). The bandwidth of the plot determines the smoothing function, the higher the bandwidth the more the plot smoothing effect. The peak density represents the highest count of the predicted ICP values in the distribution. A comparison of measured and estimated ICP is demonstrated graphically in Bland-Altman plots (FIGS. 17 and 18) using XGBoost were generated and t-tests were used to measure agreement between measured and the mean and peak density of the estimated ICP for both the arteries and the veins. T-test statistics and Bland-Altman bias measures are reported in Table 6. The arterial peak density provided the closest estimate of measured ICP (Bland-Altman bias −0.03, p<0.99).

TABLE 6

| Predicted ICP | t-test statistic | P value | Bland Altman Bias |
|---|---|---|---|
| Mean arterial model | −0.287 | 0.46 | −1.32 |
| Mean venous model | −0.018 | 0.78 | −0.366 |
| Peak density arterial model | −0.018 | 0.99 | −0.03 |
| Peak density venous model | 0.308 | 0.77 | 0.563 |

Thus, the applicant has found by use of the training and validation data set a method 200 of determining accuracy of predicted intracranial pressure according to another preferred embodiment of the present invention. This method is illustrated as an example flowchart in FIG. 3. First, video images are from a subject taken via modified the photoplethysmographic technique (i.e. step 202) and processed to produce retinal vascular pulsation data (step 204). It is expected that each trained model learning process will be able to output a plurality of predicted intracranial pressures for each model, i.e. the arterial model based primarily on the arterial pulsation data (step 206) and the venous model based primarily on the venous pulsation data (step 208). The plurality of data basis values used that can be used are one or more nine parameters also used in the training data sets are $IOP_i$, $HRW_a$, information associated with the frequency components, i.e. $a_{n1}$, $a_{n2}$, $b_{n,1}$, $b_{n,2}$, laterality, hemiretina, induced intracranial pressure, and distance of the recorded segment of artery or vein from the central optic nerve. However, it can be seen that from FIGS. 9 and 10 that some features are more important than others, therefore at least the induced ocular pressure can be used as one of the features, with one or more of the other information are also able to be used.

Statistical analysis can be conducted on first and second pluralities of predicted intracranial pressure values which are output from the trained arterial and venous models. It is preferred that statistical processing can be conducted on the pluralities of predicted intracranial pressure values, such as measures of central tendency. As discussed in Table 6, the mean and peak density of the pluralities of predicted intracranial pressure values. However, as the distribution of the $HRW_a$ and/or coefficients of the frequency components is non-normal, it is preferable to use the median or peak density as the measure of central tendency. In the preferred embodiment illustrated in FIG. 3, the peak density of ICP from the arterial and venous models are calculated in steps 210 and 212.

In a most preferred embodiment, the peak densities of the determined intracranial pressure values from the arterial model and venous models can be compared to determine the accuracy of the non-invasive determination of intracranial pressure (step 214). Specifically, it can be seen that the peak density of the determined intracranial pressure values from the arterial model provides the closest fit to measured intracranial pressure value (for example taken by an invasive method such as lumbar puncture). However, comparing the peak density of predicted ICP by both trained models, in both arterial and venous systems, as plotted in FIGS. 16A and 16B (Table 5) can be used to give an indication of the accuracy of the arterial model. Specifically, where the venous and arterial trained models predict intracranial pressure peak density values which are in better agreement, the predicted intracranial pressure from the arterial model is more accurate.

Discussion

The applicant has applied an XGB decision tree algorithm to solve the regression problem in the prediction of ICP using the Fourier decomposition of the retinal vascular pulse amplitude. The arterial model demonstrated a higher predictive accuracy than the venous model. Although a number of studies described non-invasive prior methods of ICP prediction, it appears that these methods are either not sufficiently accurate, reliable, or robust enough for widespread clinical adoption or require additional independent validation, in spite of the high linear correlation reported between the tested variables and ICP. Heteroscedasticity, the variance between individuals, limits the practicality of linear models to estimate CSF non-invasively and may explain the discrepancy between reported high correlations in non-invasive techniques and inability of these methods to supersede invasive prior art methods. The main advantage of regression trees is that they have the ability of generating a prediction without ever specifying a structure for the mean model. Although for most approaches the method implicitly assumes homogeneous variance across the entire explanatory-variable space. The pruning algorithm is the limiting factor in the ability of the algorithm in addressing this limitation. The unique solution offered by the XGB algorithm appears to address the inter-individual variance and a reasonably accurate prediction can be generated in our sample.

Feature importance showed that $IOP_i$ was the most important parameter for use in the training data sets for training both the arterial and venous models (FIG. 9 and FIG. 10), this may be related to the correlation between venous opening pressure and ICP. It is interesting to note that although $a_{n1}$ was a significant feature for both vascular models, laterality rather than the $HRW_a$ was a more important feature in the arterial model, and the hemiretinal location of the blood vessel was the least important feature in both models, this may be reflected in the fact that asymmetrical vessel trees dominate in circulatory system, as lateral asymmetry in the cardiovascular system plays an important role with respect to optimization of functions. This is demonstrated as well in the SHAP summary plots (FIG. 13 and FIG. 14), where there is a high impact of laterality on the model output in both vascular models.

The XGB algorithm showed high accuracy in the non-invasive prediction of intracranial pressure. The arterial model showed higher predictive accuracy compared to the venous. The peak density of the estimated ICP generated from the arterial model showed the highest agreement with measured ICP.

Using a Linear Model to Interpret Intracranial Pressure Results

In this example, the applicant details the use of a hierarchical linear mixed-effects model to analyse the photoplethysmographic data in the Fourier domain, i.e. by decomposing it into frequency components and using it to understand the interactions between the vascular pulsation data and intracranial pressure. The linear model provides insight into the response of the vascular system to changes in intracranial pressure, and also attempts to address heteroscedasticity such as weighted regression and transformation. Also, the photoplethysmographic data structure is hierarchical (nested), which requires one to account for the random effects in the analysis. Photoplethysmographic information is essentially a time series, which can be analysed in both the time and frequency (Fourier) domains. There are several advantages to performing the analysis in the Fourier domain, most importantly, through its sine and cosine coefficient magnitudes, it standardizes comparisons between different series, and expresses the contribution from a single frequency.

Similar to those discussed above, all the vascular datapoints generated from the captured images from a blood vessel measuring of approximately 2 mm in length from the centre of the optic disc to build a separate model from each of the arterial and venous systems. The use of the hierarchical linear mixed-effects model provides insight into, and allows interpretation, of the response of the vascular system to changes in intracranial pressure.

The applicant compared the retinal vascular pulsatile characteristics in subjects with normal ($ICP_n$) and high ($ICP_h$) intracranial pressure and quantified the interactions between intraocular pressure, intracranial pressure, and retinal vascular pulse amplitude in the Fourier domain.

Materials and Methods

Figure 20:
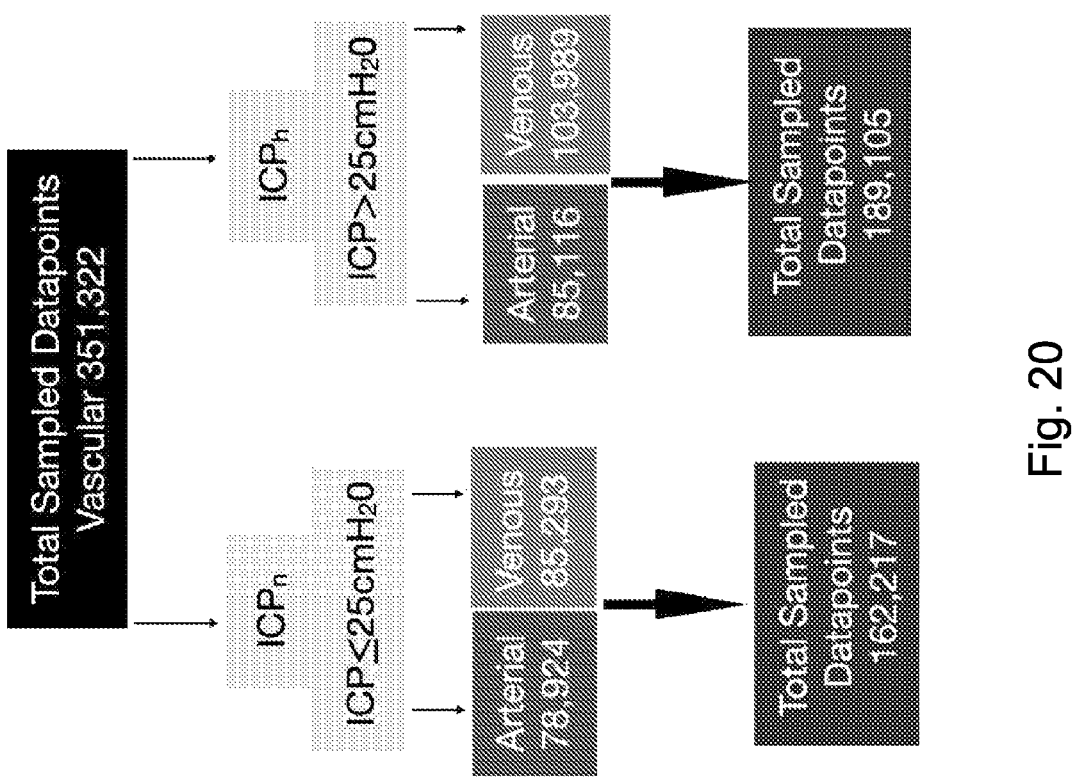
FIG. 20 shows the data points of training and test study groups according to the first example of the present invention.
Figure 19:
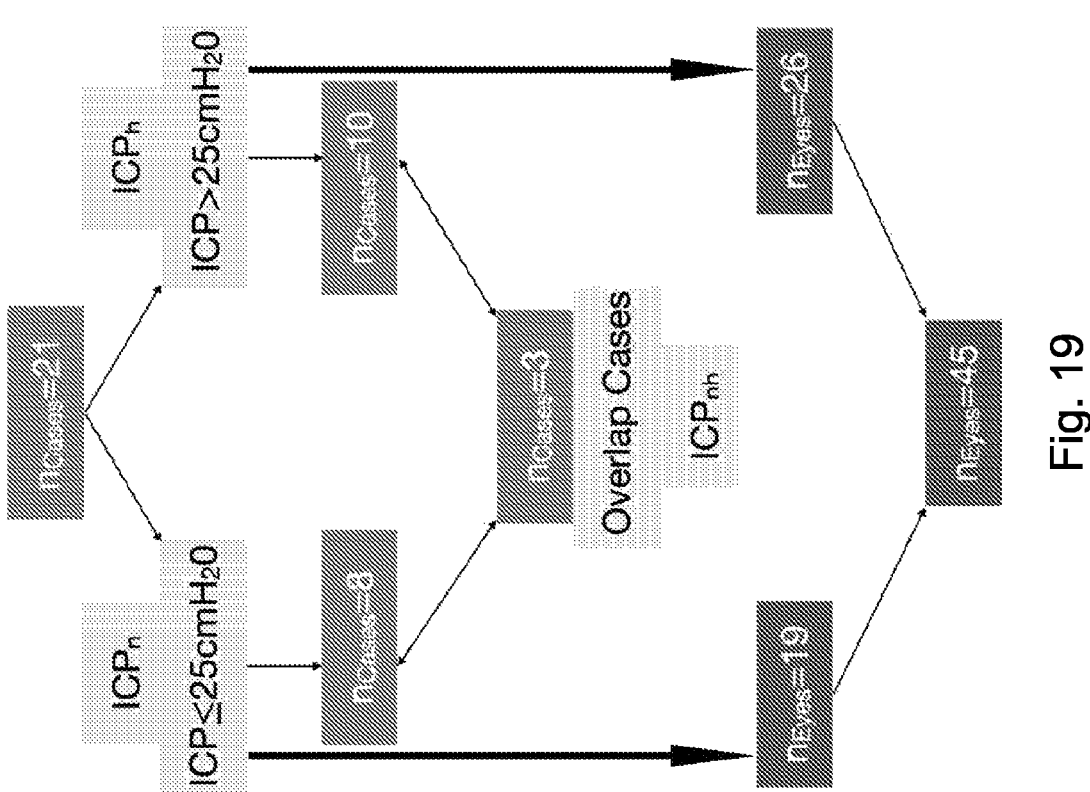
FIG. 19 shows the classification of the study population according to a first example of the present invention.

Twenty-one subjects were examined using modified retinal photoplethysmography with simultaneous measurement of venous pulsation pressure using ophthalmodynamometry (see FIGS. 19 and 20). Pulse amplitude distribution along the retinal vessels was calculated using harmonic regression analysis. The pulse wave attenuation was measured under different ranges of induced intraocular pressure (IOPi, in mmHg), as a function of distance along the vessel ($V_{Dist}$), which in turn was measured in millimetres from the centre of the optic disc. Intracranial pressure (ICP) was measured in centimetres water ($cm_{H2O}$) using lumbar puncture. A five-level hierarchical linear mixed-effects model randomized by intercepts was used to estimate the correlations between the Yeo-Johnson transformed harmonic regression wave amplitude ($HRW_{a-YJt}$) in the retinal arteries and veins and the first two Fourier trigonometric coefficients with the variables, $IOP_i$, $V_{Dist}$, and ICP.

Results

There were 10 subjects in the high intracranial pressure group ($ICP_h$>25 cmH2O), 8 cases in the normal intracranial pressure group ($ICP_n$≤25 cmH2O), three cases overlapped both groups throughout the observation period. The median $HRW_a$ in the $ICP_n$ group was higher in the retinal veins (4.563, interquartile range (IQR)=3.656) compared to the retinal arteries (3.475, IQR=2.458), the difference between the median amplitudes was statistically significant (p<0.0001). The Yeo-Johnson-transformed Fourier sine coefficient ($b_{n1,2}$) showed strong interaction with ICP and loss of the main effect in the $ICP_h$ group. This suggests that this coefficient is likely to be a mediator of the retinal vascular response to the ICP wave. A five-level hierarchical linear mixed-effects model showed the decay in the venous ($HRW_{a-YJt}$, −0.067±0.002) was almost twice that in the retinal arteries (−0.028±0.0021, p<0.00001). Similarly, the damping influence of ICP on vascular pulsation was twice that in the retinal veins (−0.0059±0.0004, p<0.00001) compared to the retinal arteries (−0.0031±0.0004, p<0.00001). There was a reversal of the ICP/$IOP_i$ linear coefficient ratio in the retinal arteries (0.44) compared to the retinal veins (1.16). The LME with interactions between the predictors for the $HRW_{a-YJt}$ achieved statistical significance (p<0.001) for all terms, except the $IOP_i$ term, whereas it achieved statistical significance in the retinal veins (p<0.01), it failed to do so in the retinal arteries. The overall interaction model had a total explanatory power of (conditional R2) of 38.7%, and 42%, in which the fixed effects explained 8.8%, and 5.8% of the variance (marginal R2) for the venous and arterial models respectively. The low explanatory power for the tested variables was due to heteroscedasticity of the $HRW_{a\text{-}YJt}$ and its coefficients in the study group.

Participants were recruited over four years (2015-2019). Subjects undergoing lumbar puncture or continuous ICP monitoring via external ventricular drain underwent modified photoplethysmography consisting of contact lens ophthalmodynamometry to vary induced intraocular pressure (IOP) and consequently venous pulsation pressure, with concomitant imaging of the optic disc. Written consent was obtained from each of the participants. Study approval was obtained from the University of Western Australia Human Ethics Committee adhering to the tenets of the Declaration of Helsinki. Participants were required to have clear ocular media. Exclusion criteria included any previous history of retinal or optic nerve pathology, optical media opacity, and inability to cooperate with the imaging technique.

Image Acquisition

After measuring visual acuity and performing a slit-lamp examination, baseline intraocular pressure was measured with Goldmann contact tonometry. The Meditron ophthalmodynamometer (Meditron GmbH, Poststrasse, Volklingen, Germany) was used to induce an increase in baseline intraocular pressure (IOPb). This device consists of a sensor ring, which measures the force surrounding a central Goldmann three-mirror contact lens. The optic nerve head was continuously imaged bio-microscopically during the examination through the Meditron Ophthalmodynamometer central contact lens. The examination was repeated over a range of induced intraocular pressures (IOPi) for each subject to attain a range of IOPi values for each eye. Videos showing excessive motion artifact, reflection from the optical media, or decentration of the optic nerve in the image sequence for less than three consecutive cardiac cycles were rejected from the analysis. The ophthalmodynamometric force (ODF) displayed as Meditron units (mu) were converted to induced intraocular pressure (IOPi) using the following formula (1):

$$IOP_i = 0.89 \cdot ODF + IOP_b$$

where $IOP_b$ is the baseline intraocular pressure in millimetres mercury (mmHg).

An imaging slit-lamp (Carl Zeiss, Germany) with a mounted digital camera (Canon 5D Mark III, Japan) was used to capture the video of the optic nerve, and thereby image the retinal vascular pulsation of the eye of the subject. Several sequences of at least three cardiac cycles in length were taken, each at a rate of 25 frames/second. Sequences of one cardiac cycle can be taken, although may produce results with less accuracy. When possible, recordings were taken from both eyes. A pulse oximeter (Nellcor N65, Covidien, Mansfield, MA) was applied to the right index finger; the audio signal from the pulse oximeter was recorded with the video sequence of the optic nerve. This allowed synchronisation of the retinal vascular pulsation with the cardiac cycle. Timing of the cardiac cycle was generated from the audio signal from the subject's pulse oximetry recorded on the audio trace of the video segment, which in turn enabled the mathematical analysis of the periodic component from green channel transmittance. A single high quality three cardiac cycle length video recording was extracted from each recording session.

Image Analysis

Image processing of the retinal vascular pulsation images was conducted (in Adobe Photoshop CS6) to produce retinal vascular pulsation data as a time-varying signal. In particular, individual image frames were extracted from each video sequence of the optic nerve and saved as Tagged Image File Format (TIFF) files. Each of these images was cropped to an array of pixels. All images from three cardiac cycles were analysed in R statistical package using custom software. Each point of the retinal vascular pulsation data can also be presented in time (for example, in seconds thereby presenting a time-varying signal) and can also be represented (by the mean of the green channel intensity) at time measured as a fraction of the cardiac cycle.

The retinal vascular pulsation data representation as a time-varying signal can then be decomposed into frequency components. This decomposition is modelled separately for the arteries and veins. The decomposition into frequency (periodic) components is preferably a $$\mathcal{F}(f(t)_p) = a_0 + \sum_{n=1}^{\infty} a_n \cdot \cos(n\pi t) + b_n \cdot \sin(n\pi t)$$

harmonic regression waveform expansion, also known as a Fourier series expansion, represented by the following equation (2):

wherein $f(t)_p$=The periodic component of the time series, $a_0$=Coefficient representing the mean of $f(t)_p$, $a_n$=coefficient of the cosine function of $f(t)_p$, $b_n$=coefficient of the sine function of $f(t)_p$, n=integer 0, 1, 2 . . . etc representing the harmonic component $\epsilon$=error term. It is preferred that decomposition is made on the basis of at least two of the frequency components, n≥2, i.e. the first and second order frequencies. Higher harmonic frequency model comparisons were conducted using Akaike Information Criterion (AIC) which showed models with first and second order frequencies were preferred so final analysis was thus limited to the first and second harmonics. However, the applicant considers higher orders could also be utilised. The amplitude of the composite (combined first and second harmonic waveforms) was termed the harmonic regression wave amplitude ($HRW_a$).

Statistical Analysis

The harmonic regression model is a time series, with both a harmonic trigonometric series and autoregressive error terms. The amplitude of the composite (combined first and second harmonic waveforms) was termed the harmonic regression wave amplitude ($HRW_a$), which was modelled for the arteries and veins separately. The distribution of the $HRW_a$ and the majority of the Fourier coefficients were non-normal, therefore the median was used as a measure of central tendency and the interquartile range (IQR) was used to estimate dispersion. The range, minimum, maximum, skew, and kurtosis of these parameters were also computed. The Wilcoxon test with Bonferroni correction was used in the hypothesis test of the differences in the medians of the non-transformed data. Yeo-Johnson transformation (YJt) was used to normalise the harmonic regression waveform amplitude ($HRW_a$), the cosine ($a_{n1,2}$) and the sine ($b_{n1,2}$) coefficients of the Fourier trigonometric series. The justification of this approach was supported by the Estimated Normality Statistics (Pearson P/df), which showed favourable transformation criteria when compared against non-transformed and $log_{10}$ transformed data (Table 7). This transformation is a suitable approach for negative values, unlike the logarithmic transform. Adding a constant to negative values to translate the scale of values for a log transform will impact the results of the hypothesis test p-values. Yeo and Johnson proposed a family of distributions that can be used without the restrictions of the properties of the Box-Cox power family. These transformations are defined by:

$$\psi(\lambda, y) = \begin{cases} \dfrac{(y+1)^{\lambda}}{\lambda} & \text{if } \lambda \neq 0, y \geq 0 \\ \log(y+1) & \text{if } \lambda = 0, y \geq 0 \\ \dfrac{(-[y+1])^{2-\lambda} - 1}{2-\lambda} & \text{if } \lambda \neq 2, y < 0 \\ -\log(-y+1) & \text{if } \lambda = 2, y < 0 \end{cases}$$

$$\psi(\lambda, y) = \begin{cases} \dfrac{(y+1)^{\lambda}}{\lambda} & \text{if } \lambda \neq 0, y \geq 0 \\ \log(y+1) & \text{if } \lambda = 0, y \geq 0 \\ \dfrac{(-[y+1])^{2-\lambda} - 1}{2-\lambda} & \text{if } \lambda \neq 2, y < 0 \\ -\log(-y+1) & \text{if } \lambda = 2, y < 0 \end{cases}$$

Unlike a logarithmic transform, $YJ_t$ is suitable for negative values, which requires translation with a constant. If strictly positive, then the $YJ_t$ is the same as the Box-Cox power transformation of (y+1). If strictly negative, then the $YJ_t$ is the Box-Cox power transformation of (−y+1), but with power 2-$\lambda$. With both negative and positive values, the transformation is a mixture of these two, so different powers are used for positive and negative values. Translation with a constant can be problematic when a different constant is required for the $a_{n1,2}$ and the $b_{n1,2}$ coefficients. The Estimated Normality Statistics (Pearson P/degrees of freedom) were used, this showed favourable transformation criteria for $YJ_t$ data when compared against both non-transformed and Logarithmic transformation with translation (Table 7). The lower the normality statistic the more favourable approximation to a normal distribution. The mean±standard error (SE) and standard deviation (SD) were used as a measure of central tendency and dispersion respectively for the $YJ_t$ data.

Multivariate analysis of variance (MANOVA) was used to test the differences between the means in the transformed dataset. Multifactoral Homogeneity of variance was tested using the Levene test.

Table 7: Estimated normality statistics (Pearson P/df) comparing non-transformed with Yeo-Johnson Power transformed parameters of the Fourier series. The lower the normality statistic the more favourable approximation to a normal distribution. $\lambda$ is the critical parameter for the Yeo-Johnson transformation.

Study Population

There were a total of 21 patients in the study group, 10 cases were in the high intracranial pressure group ($ICP_h$>25 $cmH_2O$) and 8 cases in the normal intracranial pressure group ($ICP_n$≤25 $cmH_2O$). Three cases overlapped between the two groups as a result of interchanging between the $ICP_n$ to the $ICP_h$ groups over four years (2015-2019) of observation. Therefore, there was a total of 19 eyes in the $ICP_n$ group and 26 eyes in the $ICP_h$ group, giving a total of 45 eyes in the study as three eyes were excluded from the analysis due to poor image quality (FIG. 19). A total of 351,322 data points was sampled from the images of the study group 162,217 arterial and 189,105 venous datapoints (FIG. 20). The age of the population demonstrated a bimodal distribution with a mean of 30 years (range 17-47 years). There were 20 (95.2%) females and 1(4.8%) male. An ICP of 25 cm $H_2O$ was considered the upper normal limit. Whereas in the $ICP_n$ group the median was 18.50 cm $H_2O$ (min 9.50, max=24, IQR=5.5), the corresponding values in $ICP_h$ group was 31 cm $H_2O$ (min 25.50, max=68, IQR=11).

FIGS. 19 and 20 are schematic diagrams of the classification of the study population and image sampling respectively. FIG. 19 shows the study group with normal intracranial pressure $ICP_n$ ($ICP$≤25 cm $H_2O$) and FIG. 20 shows the study group with high intracranial pressure $ICP_h$ ($ICP$>25 cm $H_2O$). The median±IQR (line and centre dot) and range (end dots) are highlighted for each group. The change in distribution characteristics is quantified using the Anderson-Darling statistic. There was a reduction of the venous and an increase in the arterial median and range of the vascular pulsation amplitudes. FIG. 21 demonstrates the decay in the venous Yeo-Johnson transformed $HRW_{a-YJtV}$ with both predictors $V_{Dist}$ and ICP. The slope of regression line correlating the $HRW_a$ with $V_{Dist}$ was −0.071±0.002 (p-value<0.00001) whereas that correlating with ICP was −0.0059±0.0004 (p-value<0.00001). There was amplification of the $HRW_a$ as indicated by a positive slope of regression with $IOP_i$, was 0.0051±0.00006 (p-value<0.00001). The corresponding values for the retinal arterial system were −0.028±0.0021, 0.0031±0.0004 and 0.0071±0.000065 (p-value<0.00001) respectively.

The Harmonic Regression Waveform and Coefficients

For both study groups, the distribution of the harmonic regression waveform amplitude ($HRW_a$) and the components of the Fourier trigonometric series cosine ($a_{n1,2}$) and sine coefficients ($b_{n1,2}$) of the first and second Fourier harmonics respectively in both the retinal arteries and veins is summarised in Table 8. The largest difference in the distribution between both study groups as indicated by the Anderson-Darling statistic of the terms of the Fourier series is noted in the venous first Fourier harmonics ($a_{n1}$, $b_{n1}$) followed by the arterial first Fourier harmonics $a_{n1}$, $b_{n1}$).

TABLE 7

| Artery | Non-transformed | Yeo-Johnson Transformed | $\lambda$ | Vein | Non-transformed | Yeo-Johnson Transformed | $\lambda$ |
|---|---|---|---|---|---|---|---|
| $HRW_a$ | 35.5325 | 6.5197 | −0.635 | $HRW_a$ | 63.0409 | 7.5351 | −0.1684 |
| $a_{n1}$ | 2.6041 | 1.9499 | 0.9406 | $a_{n1}$ | 21.6354 | 5.9935 | 0.7561 |
| $b_{n1}$ | 12.5317 | 12.7153 | 0.9747 | $b_{n1}$ | 23.2509 | 23.0105 | 1.0128 |
| $a_{n2}$ | 5.6896 | 5.7172 | 0.8976 | $a_{n2}$ | 11.1054 | 9.856 | 1.0871 |
| $b_{n2}$ | 5.9913 | 5.8878 | 1.0475 | $b_{n2}$ | 12.5743 | 12.338 | 1.0561 |

TABLE 8

| Artery | ICP$_n$ | ICP$_h$ | Vein | ICP$_n$ | ICP$_h$ |
|---|---|---|---|---|---|
| HRW$_a$ | Lognormal (97.30) | Lognormal (110.81) | HRW$_a$ | Lognormal (87.71) | Lognormal (171.18) |
| a$_{n1}$ | Normal (69.02) | Normal (43.32) | a$_{n1}$ | Logistic (325.11) | Normal (1.19) |
| b$_{n1}$ | Logistic (108.01) | Logistic (262.02) | b$_{n1}$ | Logistic (205.11) | Normal (1.02) |
| a$_{n2}$ | Logistic (32.11) | Logistic (30.26) | a$_{n2}$ | Logistic (139.12) | Logistic (86.16) |
| b$_{n2}$ | Logistic (10.37) | Logistic (7.26) | b$_{n2}$ | Logistic (70.77) | Logistic (80.32) |

The descriptive statistical parameters were computed for both the ICP$_n$ and ICP$_h$ groups for both retinal vascular systems are shown in Table 9. Data from this table could be summarised graphically in FIG. 21, from which the following conclusions can be drawn: The median venous HRW$_a$ was higher in the ICP$_n$ group (4.563, IQR=3.656, range=0.228-14.434) compared to the ICP$_h$ group (3.655, IQR=3.223, range=0.339-11.983), this was in contrast to the arterial pulsation amplitudes where the median arterial HRW$_a$ was higher in the ICP$_h$ group (3.616, IQR=2.715, cosine coefficient of the first harmonic, b$_{n1}$=Fourier sine coefficient of the first harmonic, a$_{n2}$=Fourier cosine coefficient of the second harmonic, b$_{n2}$=Fourier sine coefficient of the second harmonic, ICP$_n$=normal intracranial pressure, ICP$_h$=high intracranial pressure, IQR=interquartile range, SD=standard deviation, SE=standard error. x$^w$=Within group x$^b$=between group median differences failed to achieve statistical significance at a level of p<0.05.

TABLE 9

| Parameter | Site | Mean | SD | Median | IQR | Min | Max | Range | Skew | Kurtosis | SE |
|---|---|---|---|---|---|---|---|---|---|---|---|
| ICP$_n$ | | | | | | | | | | | |
| HRW$_a$ | Artery | 3.832 | 1.797 | 3.475 | 2.458 | 0.353 | 9.233 | 8.88 | 0.786 | 0.045 | 0.006 |
| a$_{n1}$ | Artery | 0.121 | 1.113 | 0.078 | 1.469 | -3.924 | 4.446 | 8.37 | 0.209 | 0.188 | 0.004 |
| b$_{n1}$ | Artery | -1.034 | 1.047 | -1.001 | 1.153 | 4.61 | -4.088 | 8.699 | 0.112 | 0.729 | 0.004 |
| a$_{n2}$ | Artery | -0.006 | 0.483 | 0.011 | 0.574 | -2.505 | 2.755 | 5.26 | 0.012 | 1.072 | 0.002 |
| b$_{n2}$ | Artery | 0.078 | 0.485 | 0.083 | 0.561 | -3.388 | 3.258 | 6.647 | -0.104 | 1.801 | 0.002 |
| HRW$_a$ | Vein | 5.335 | 2.915 | 4.563 | 3.656 | 0.228 | 14.434 | 14.207 | 1.037 | 0.477 | 0.01 |
| a$_{n1}$ | Vein | 0.611 | 1.688 | 0.440b | 2.057 | -6.405 | 7.045 | 13.45 | 0.639 | 0.716 | 0.006 |
| b$_{n1}$ | Vein | -1.412 | 1.538 | -1.324 | 1.596 | -7.211 | 5.573 | 12.785 | -0.11 | 1.161 | 0.005 |
| a$_{n2}$ | Vein | -0.114 | 0.604 | -0.072 | 0.685 | -4.335 | 4.248 | 8.583 | -0.199 | 2.217 | 0.002 |
| b$_{n2}$ | Vein | 0.125 | 0.580 | 0.130 | 0.623 | -3.741 | 4.064 | 7.805 | -0.066 | 2.493 | 0.002 |
| ICP$_h$ | | | | | | | | | | | |
| HRW$_a$ | Artery | 4.047 | 1.995 | 3.616 | 2.715 | 0.338 | 9.983 | 9.645 | 0.801 | 0.016 | 0.007 |
| a$_{n1}$ | Artery | 0.214 | 1.249 | 0.179 | 1.666 | -4.826 | 4.749 | 9.576 | 0.032 | 0.230 | 0.004 |
| b$_{n1}$ | Artery | -1.127 | 0.994 | -1.029w | 1.120 | -4.937 | 4.37 | 9.307 | -0.247 | 1.191 | 0.003 |
| a$_{n2}$ | Artery | 0.002 | -0.0002 | 0.522 | -0.015 | 0.605 | -2.911 | 3.158 | 6.069 | 0.286 | 1.149 |
| b$_{n2}$ | Artery | 0.06 | 0.529 | 0.063w | 0.622 | -3.022 | 3.256 | 6.277 | -0.028 | 1.149 | 0.002 |
| HRW$_a$ | Vein | 4.321 | 2.468 | 3.655 | 3.223 | 0.339 | 11.983 | 11.645 | 1.009 | 0.37 | 0.008 |
| a$_{n1}$ | Vein | 0.585 | 1.406 | 0.364b | 1.711 | -5.707 | 5.963 | 11.67 | 0.635 | 0.817 | 0.004 |
| b$_{n1}$ | Vein | -1.147 | 1.108 | -1.018w | 1.198 | -5.918 | 5.769 | 11.687 | -0.184 | 2.073 | 0.003 |
| a$_{n2}$ | Vein | -0.041 | 0.541 | -0.016 | 0.613 | -3.797 | 3.731 | 7.528 | -0.053 | 1.761 | 0.002 |
| b$_{n2}$ | Vein | 0.056 | 0.55 | 0.061w | 0.597 | -3.723 | 4.246 | 7.969 | -0.126 | 2.071 | 0.00 | range=0.338-9.983) compared to the ICP$_n$ group (3.475, IQR=2.458, range=0.353-9.233). Between (ICP$_h$ and ICP$_n$) and within (artery and vein) group differences in the median pulsation amplitudes achieved statistical significance (p<0.0001) for all, except the venous and coefficient between groups and the b$_{n1,2}$ within in the ICP$_h$ group.

FIG. 21 shows violin plots of the distribution of the HRW$_a$. The top plot is the study group with normal intracranial pressure ICP, (ICP≤25 cm H$_2$O) while the bottom plot shows the study group with high intracranial pressure ICP$_h$ (ICP>25 cm H$_2$O). The median±IQR (line and centre dot) and range (end dots) are highlighted for each group. The change in distribution characteristics is quantified using the Anderson-Darling statistic. There was attenuation of the HRW$_a$ in the retinal venous system with increased distance along the vessel (V$_{Dist}$) and with increasing intracranial pressure (ICP). An amplification of the HRW$_a$ with increase in the induced intraocular pressure (IOP$_i$) is noted.

Table 9 show the descriptive statistics of the harmonic regression wave amplitude, the cosine and sine coefficients of the first and second harmonics of the two study groups. HRW$_a$=harmonic regression wave amplitude, a$_{n1}$=Fourier Yeo-Johnson Power Transformation Yeo-Johnson transformation (YJ$_t$) was undertaken to normalize the HRW$_a$ and other parameters of the Fourier equation. The descriptive statistics are highlighted in Table 10 demonstrate the reduction of the skew for the majority of the trigonometric terms and especially the HRW$_a$. For some terms where the skew increased after transformation, especially all the ICP$_h$ arterial terms, was negligible. As in the non-transformed Fourier terms, statistical significance in the differences between the mean of the YJ$_t$ parameters was sustained (p<0.001) in all except the b$_{n1,2}$ in the ICP$_h$ group. Between-group differences were statistically significant in all (p<0.001) except the arterial a$_{n2}$ coefficient. Both within and between-group heterogeneity of the variances was demonstrated using the Levene test (p<0.0001) for the transformed and non-transformed Fourier terms.

Table 10 shows the descriptive statistics of the Yeo-Johnson transformed harmonic regression wave amplitude, the cosine and sine coefficients of the first and second harmonics of the two study groups. Yeo-Johnson transformed HRW$_a$=harmonic regression wave amplitude, a$_{n1}$=Fourier cosine coefficient of the first harmonic, $b_{n1}$=Fourier sine coefficient of the first harmonic, $a_{n2}$=Fourier cosine coefficient of the second harmonic, $b_{n2}$=Fourier sine coefficient of the second harmonic, $ICP_n$=normal intracranial pressure, $ICP_h$=high intracranial pressure, IQR=interquartile range, SD=standard deviation, SE=standard error. $x^w$=Within group $x^b$=between group median differences failed to achieve statistical significance at a level of p<0.05.

10.2 times that of ICP (11.3 in the retinal veins and 9.1 in the retinal arteries). Whereas the ratio of $ICP/IOP_i$ is almost a 1:1 ratio (1.16) in the retinal veins, the influence of the damping effect of ICP on vessel wall oscillation is reduced as indicated by the reduction of the latter ratio to 0.44 in the retinal arteries, likely as a consequence of cerebral auto-regulatory mechanisms.

TABLE 10

| Parameter | Site | Mean | SD | Min | Max | Range | Skew | Kurtosis | SE |
|---|---|---|---|---|---|---|---|---|---|
| $ICP_n$ | | | | | | | | | |
| $HRW_a$ | Artery | 1.435 | 0.332 | 0.299 | 2.162 | 1.863 | 0.008 | −0.627 | 0.001 |
| $a_{n1}$ | Artery | 0.096 | 1.105 | −4.165 | 4.172 | 8.338 | 0.084 | 0.155 | 0.004 |
| $b_{n1}$ | Artery | −1.052 | 1.062 | −4.74 | 3.985 | 8.724 | 0.055 | 0.683 | 0.004 |
| $a_{n2}$ | Artery | −0.016b | 0.484 | −2.708 | 2.539 | 5.248 | −0.15 | 1.016 | 0.002 |
| $b_{n2}$ | Artery | 0.083 | 0.487 | −3.245 | 3.4 | 6.645 | −0.013 | 1.784 | 0.002 |
| $HRW_a$ | Vein | 1.502 | 0.326 | 0.202 | 2.193 | 1.991 | 0.015 | −0.564 | 0.001 |
| $a_{n1}$ | Vein | 0.404 | 1.53 | −8.898 | 5.076 | 13.974 | −0.062 | 0.6 | 0.005 |
| $b_{n1}$ | Vein | −1.396 | 1.524 | −7.083 | 5.661 | 12.745 | −0.069 | 1.181 | 0.005 |
| $a_{n2}$ | Vein | −0.102 | 0.598 | −3.956 | 4.657 | 8.613 | 0.015 | 2.446 | 0.002 |
| $b_{n2}$ | Vein | 0.133 | 0.583 | −3.544 | 4.304 | 7.848 | 0.076 | 2.538 | 0.002 |
| $ICP_h$ | | | | | | | | | |
| $HRW_a$ | Artery | 1.466 | 0.353 | 0.288 | 2.223 | 1.935 | −0.012 | −0.618 | 0.001 |
| $a_{n1}$ | Artery | 0.182 | 1.241 | −5.163 | 4.446 | 9.609 | −0.108 | 0.297 | 0.004 |
| $b_{n1}$ | Artery | −1.145w | 1.011 | −5.082 | 4.255 | 9.336 | −0.305 | 1.144 | 0.003 |
| $a_{n2}$ | Artery | −0.011b | 0.52 | −3.173 | 2.889 | 6.062 | 0.114 | 1.022 | 0.002 |
| $b_{n2}$ | Artery | 0.065w | 0.531 | −2.902 | 3.397 | 6.299 | 0.055 | 1.145 | 0.002 |
| $HRW_a$ | Vein | 1.368 | 0.338 | 0.285 | 2.082 | 1.797 | 0.054 | −0.719 | 0.001 |
| $a_{n1}$ | Vein | 0.429 | 1.268 | −7.773 | 4.414 | 12.187 | −0.054 | 1.296 | 0.004 |
| $b_{n1}$ | Vein | −1.137w | 1.098 | −5.823 | 5.862 | 11.685 | −0.143 | 2.143 | 0.003 |
| $a_{n2}$ | Vein | −0.031 | 0.54 | −3.488 | 4.062 | 7.551 | 0.128 | 1.894 | 0.002 |
| $b_{n2}$ | Vein | 0.063w | 0.551 | −3.527 | 4.505 | 8.032 | −0.001 | 2.017 | 0.002 |

Mixed Effects Linear Regression Model

Correlations between the predictors of the hierarchical multivariate linear regression were undertaken in the YJt transformation space. In a mixed-effects linear regression model correlating the amplitude of the terms of the Fourier equation with three predictors distance along the vessel ($V_{Dist}$) measured in millimetres (mm) from the centre of the optic disc, intracranial pressure (ICP) measured in centimetres water (cmH2O) and induced intraocular pressure ($IOP_i$) measured in millimetres mercury (mmHg). The equations of the regression lines for both the venous $HRW_{a-YJtV}$, and arterial $HRW_{a-YJtA}$ can be derived (where the p<0.00001 for the coefficients of all equations):

$$HRW_{a-YJtV}=-0.0667 \cdot V_{Dist}(\pm0.002)+1.4823(\pm0.04)$$

$$HRW_{a-YJtV}=0.0051 \cdot IOP_i(\pm0.00006)+1.3156(\pm0.04)$$

$$HRW_{a-YJtV}=-0.0059 \cdot ICP(\pm0.0004)+1.5472(\pm0.04) \quad (1)$$

$$HRW_{a-YJtA}=-0.0282 \cdot V_{Dist}(\pm0.002)+1.4564(\pm0.05)$$

$$HRW_{a-YJtA}=0.0071 \cdot IOP_i(\pm0.00007)+1.2746(\pm0.05)$$

$$HRW_{a-YJtA}=-0.0031 \cdot ICP(\pm0.0004)+1.4864(\pm0.05) \quad (2)$$

Figure 24:
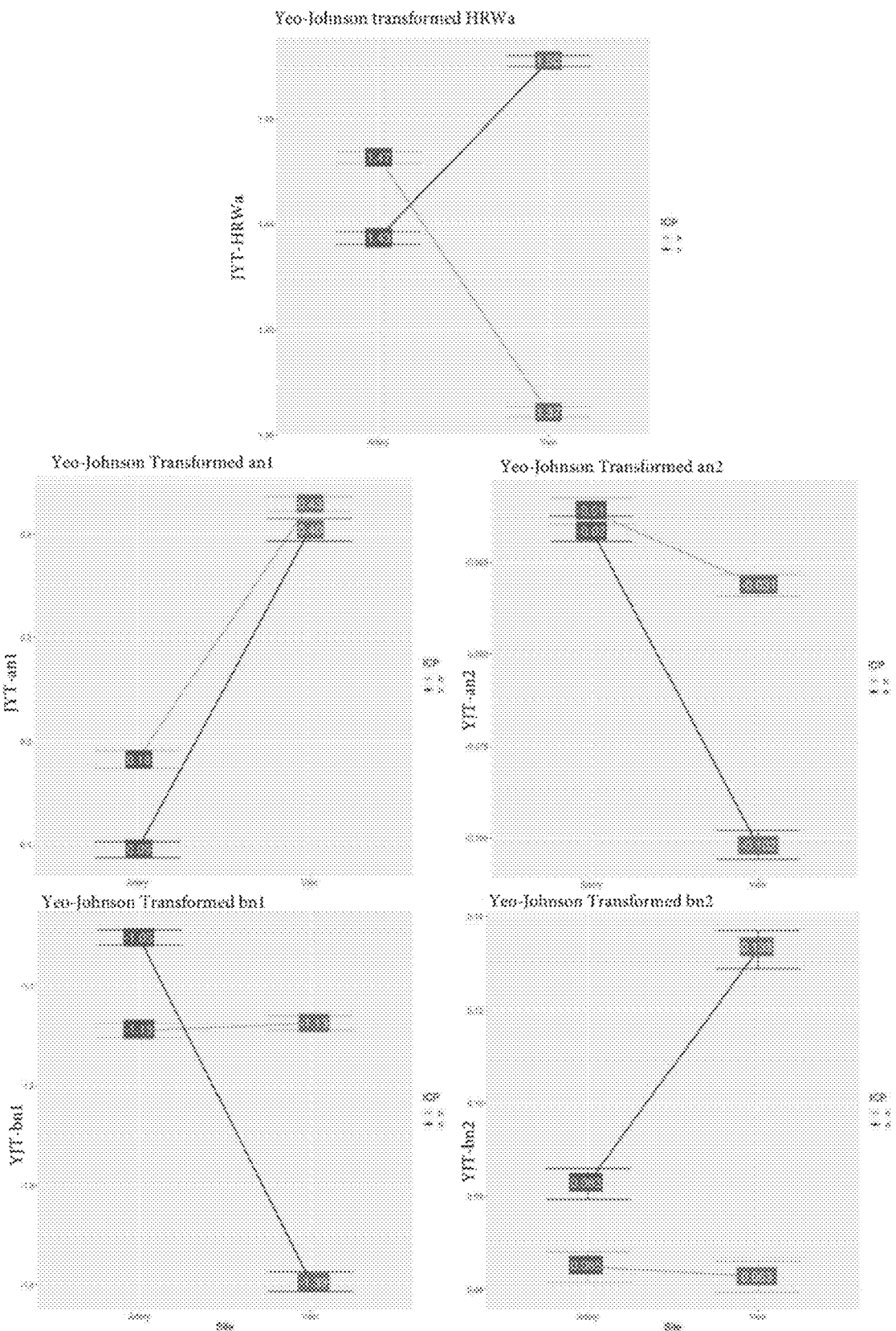
FIG. 24 shows interaction plots of the harmonic regression waveform amplitude ($HRW_a$), cosine ($a_{n1,2}$) and sine ($b_{n1,2}$) coefficients of the first and second harmonics respectively.

For both retinal vascular systems the negative coefficients of $V_{Dist}$ and ICP indicate that decay in retinal venous pulsation amplitude in response to these predictors and a positive correlation with $IOP_i$. From equation (1) and equation (2) it can be noted that due to the difference in vessel wall viscoelasticity the retinal vascular pulse wave attenuation of the retinal veins is approximately 2.5 times that of the retinal arteries. From the ratio of the coefficient of $V_{Dist}$/ICP, the damping effect of the vessel wall is on average Analysis of the interaction of the $YJ_t$ $HRW_a$ and Fourier coefficients where the main effects are ICP and vessel type is demonstrated in FIG. 24. The statistically significant difference in the mean $HRW_{a-YJt}$ pulsation amplitudes resulted in significant main effects in this plot, where the lines connecting the mean pulsation values within an ICP group are not parallel to the x-axis. Also, there was significant disordinal interaction between the two groups demonstrated by the presence of an intersection of the plot lines, which indicates a high mean arterial and low mean venous $HRW_{a-YJt}$ pulsation amplitude in the $ICP_h$ group and conversely for the ICP group. As these findings are similar to that in FIG. 21, it, therefore, forms a basis for comparison of the interactions of the Fourier coefficients. Whereas the $an1-Y_{Jt}$ showed no significant interaction between the ICP groups there was a significant main effect, the $a_{n2}$ showed ordinal interaction where between-group differences in the value of this coefficient existed only in the retinal veins (FIG. 24). Based on the strong correlation with both $V_{Dist}$ and $IOP_i$ and the lack of interaction with ICP, the coefficient likely mediates the IOP wave, and therefore the effects of $IOP_i$ on the retinal vessel wall. The interaction plots the sine ($b_{n1,2}$) coefficients strong interactions between ICP groups and the loss of main effects in the $ICP_h$ group as indicated by the parallel line joining the mean pulsation values to the x-axis (FIG. 24). Based on these observations this coefficient is likely to be the mediator of the retinal vascular response to ICP wave.

FIG. 24 shows an interaction plot of the harmonic regression waveform amplitude ($HRW_a$), cosine ($a_{n1,2}$) and sine ($b_{n1,2}$) coefficients of the first and second harmonics respectively. In both the high (h) and normal (n) intracranial pressure groups for both vascular systems there was high interaction of the $HRW_a$ and $b_{n1,2}$, between both groups, no interaction of the and term and ordinal interaction of the $a_{n2}$ term. On the basis of these findings the sine component ($b_{n1,2}$) of the Fourier wave is the coefficient likely mediating the retinal vascular pulse response to ICP changes and the cosine component ($a_{n1,2}$) likely mediates the IOP pulse wave response on the vessel wall.

A mixed-effects linear regression hierarchal model was used to numerically quantify the interactions between the predictors for the $HRW_{a-YJt}$, for the retinal veins (FIG. 25) and arteries (FIG. 26). The following regression equations (3) and (4) are expressed in terms of ICP (cm H2O), where $HRW_{a-YJt}$ is the Yeo-Johnson transformed value, $IOP_i$ is the induced IOP in mmHg, $V_{Dist}$ is in mm from the centre of the optic disc.

$$HRW_{a-YJtV} = -0.3638(\pm 0.013) \cdot V_{Dist} + 0.00091$$
$$(\pm 0.00029) \cdot IOP_i - 0.01149(\pm 0.00052) \cdot ICP +$$
$$0.0071(\pm 0.00036) \cdot V_{Dist} \cdot IOP_i + 0.0085(\pm 0.00041)$$
$$\cdot V_{Dist} \cdot ICP + 0.000094(\pm 0.0000093) \cdot IOP_i \cdot ICP -$$
$$0.0001612(\pm 0.000012) \cdot V_{Dist} \cdot IOP_i \cdot ICP + 1.69 \quad (3)$$

$$HRW_{a-YJtA} = -0.2374(\pm 0.017) \cdot V_{Dist} + -0.00038$$
$$(\pm 0.00038) \cdot IOP_i - 0.00708(\pm 0.00057) \cdot ICP +$$
$$0.0089(\pm 0.00053) \cdot V_{Dist} \cdot IOP_i +$$
$$0.00376(\pm 0.00059) \cdot V_{Dist} \cdot ICP + 0.000188$$
$$(\pm 0.000013) \cdot IOP_i \cdot ICP - 0.0002(\pm 0.000018)$$
$$\cdot V_{Dist} \cdot IOP_i \cdot ICP + 1.50 \quad (4)$$

Both equations (3) and (4) can be rearranged in terms of $V_{Dist}$, which allows the interaction terms to be eliminated if the measurement is done at the centre of the optic disc. The equations for the Harmonic Regression Waveform Amplitude—Venous (5) and Arterial (6) are as follows and displayed graphically in FIGS. 25 and 26:

$$HRW_{YJt-V} = +1.6943862 + V_{Dist} \cdot [-0.3638445 +$$
$$0.0070505 \cdot IOP_i + 0.0076471 \cdot ICP -$$
$$0.0001612 \cdot IOP_i \cdot ICP] + 0.0009149 \cdot IOP_i -$$
$$0.0114921 \cdot ICP + 0.0000943 \cdot IOP_i \cdot ICP \quad (5)$$

$$HRW_{YJt-A} = +1.5004466 + V_{Dist} \cdot [-0.2373716 +$$
$$0.0088757 \cdot IOP_i + 0.0037635 \cdot ICP -$$
$$0.0002001 \cdot IOP_i \cdot ICP] - 0.0003786 \cdot IOP_i -$$
$$0.0070824 \cdot ICP + 0.0001880 \cdot IOP_i \cdot ICP \quad (6)$$

FIG. 25 is a Trellis graph demonstrating the mixed-effects linear regression model with interactions of the Yeo-Johnson transformed venous harmonic regression waveform amplitude ($HRW_{a-YJt}$). Distance is measured in millimetres (mm) from the centre of the optic disc. The 95% confidence intervals are shown around the regression lines. Noted is a reduction of the slope of the regression with increased ICP (columns) and $IOP_i$ (rows). Whereas the y-intercepts of the regression lines are reduced with increased ICP, they are increased with higher $IOP_i$. The progressively lower y-intercepts of the regression lines along the lower left to upper right diagonal indicate that a higher $IOP_i$ is required to induce a venous pulsation with higher ICP, which will be of lower amplitude.

FIG. 26 is a Trellis graph demonstrating the mixed-effects linear regression model with interactions of the Yeo-Johnson transformed arterial harmonic regression waveform amplitude ($HRW_{a-YJt}$). Distance is measured in millimetres (mm) from the centre of the optic disc. The 95% confidence intervals are shown around the regression lines. Noted is the increase of the slope of the regression with increased ICP (columns) and $IOP_i$ (rows) particularly with ICP in the pathological range. Contrary to the retinal veins the progressively higher y-intercepts of the regression lines along the lower left to upper right diagonal indicate that amplification of the retinal arterial pulsation occurs with a higher ICP. A reversal of the slope of the regression at ICP 10-20 at an IOPi>30 mmHg. This is likely a spurious result as a consequence of the boundary conditions of the mixed-effects linear model.

All coefficients of the regression equations with interactions achieved statistical significance (p<0.001), except the arterial $IOP_i$ coefficient (p=0.32). The overall interaction model predicting the $HRW_{a-YJtw}$ had a total explanatory power (conditional $R^2$) of 38.7%, in which the fixed effects explained 8.8% of the variance (marginal $R^2$). Within this model the effect of $V_{Dist}$ and ICP were significant ($\beta_{V_{Dist}} = -0.42$, se=±0.015, p<0.00001) and ($\beta_{ICP} = -0.42$, se=±0.019, p<0.00001). Whereas that for $IOP_i$ was small ($\beta_{IOPi} = 0.031$, se=±0.0097, p<0.00001).

It can be observed from FIG. 25 that there is a reduction of the slope of the regression line with increased ICP (columns) and $IOP_i$ (rows) as a consequence of reduced venous wall viscoelasticity. Whereas the intercept of the regression lines is reduced with increased ICP, observed as a progressive reduction in venous pulsation, the converse occurs with raised $IOP_i$. Following a diagonal of the trellis graph (FIG. 25) from the lower left to the upper right, where both ICP and $IOP_i$ increase, it can be observed that a higher $IOP_i$ is required to induce venous pulsations of progressively lower amplitude in the presence of a higher ICP. The interactions in the retinal arteries seen in (FIG. 26) depend on whether ICP is pathologic or physiologic. Where ICP is pathological, the intercept of the regression lines is increased with increased $IOP_i$, this amplification of the retinal vascular pulse is likely due to the positive combined effects of $IOP_i$ and cerebral auto-regulatory mechanisms particularly raised mean arterial pressure. At the physiologic ICP range, there is an increase in the intercept therefore an increase in retinal arterial pulse amplitude with increasing $IOP_i$, however, this increase in intercept is less than that in the pathological ICP range. A reversal of the slope of the regression at ICP 10-20 at an IOPi>30 mmHg. This is likely a spurious result as a consequence of the boundary conditions of the mixed-effects linear model. Contrary to the retinal veins when a diagonal of the trellis graph (FIG. 23) is followed from the lower left to the upper right, where both ICP and $IOP_i$ increase, a corresponding increase in retinal arterial pulse amplitude can be observed.

The overall interaction model predicting the $HRW_{a-YJtA}$ has a total explanatory power (conditional $R^2$) of 42%, in which the fixed effects explained 5.8% of the variance (marginal $R^2$). Within this model the effect of $V_{Dist}$ and ICP were significant ($\beta_{V_{Dist}} = -0.26$, se=±0.019, p<0.00001) and ($\beta_{ICP} = -0.21$, se=±0.017, p<0.00001). Whereas that for $IOP_i$ was small and did not achieve statistical significance ($\beta_{IOP_i} = -0.013$, se=±0.013, p<0.32). The statistical significance of the coefficients of the linear regression model with interactions of the $HRW_{a-YJt}$ and the terms of the Fourier series are summarised in Table 11. Table 11 shows the estimated interaction model coefficients of the terms of the first two harmonics of the Fourier series. CS=computationally singular. Highlighted cells (*) represent coefficients that failed to achieve statistical significance. p-value<0.001 for the rest of the coefficients.

TABLE 11

| | $HRW_a$ | $a_{n1}$ | $b_{n1}$ | $a_{n2}$ | $b_{n2}$ |
|---|---|---|---|---|---|
| Artery | −0.237 ± 0.017 | −0.193 ± 0.05171 | 0.3681 ± 0.0551 | 0.2315 ± 0.028 | −0.1451 ± 0.0303 |
| $V_{dist}$ | −0.00038 ± 0.00038* | 0.0084 ± 0.00113 | −0.001155 ± 0.0012 | −0.00228 ± 0.00061 | −0.0047 ± 0.00066 |
| $IOP_i$ | −0.0071 ± 0.00057 | −0.0073 ± 0.0017 | 0.002934 ± 0.0018 | 0.0069 ± 0.00091 | −0.0248 ± 0.00099 |
| ICP | 0.0089 ± 0.00053 | −0.0155 ± 0.0016 | −0.0042 ± 0.00167 | 0.00051 ± 0.00084* | 0.0041 ± 0.00091 |
| $V_{Dist} \cdot IOP_i$ | 0.0037635 ± 0.00059 | 0.00221 ± 0.0018* | 0.0049 ± 0.0019 | 0.00088 ± 0.000021 | −0.000013 ± 0.000031* |
| $V_{Dist} \cdot ICP$ | 0.0037635 ± 0.00059 | 0.00221 ± 0.0018* | −0.0049 ± 0.0019 | −0.00624 ± 0.00095 | 0.00094 ± 0.001035* |
| $IOP_i \cdot ICP$ | 0.0001880 ± 0.000013 | 0.00013 ± 0.000039 | −0.000156 ± 0.000041 | 0.000088 ± 0.000021 | 0.00015 ± 0.000023 |
| $V_{Dist} \cdot IOP_i \cdot ICP$ | −0.0002 ± 0.000018 | 0.000267 ± 0.000053 | 0.000124 ± 0.000056 | 0.00001 ± 0.000029 | −0.000013 ± 0.000031* |
| Vein | | | | | |
| $V_{dist}$ | −0.3638 ± 0.013 | −0.0847 ± 0.051* | −0.5504 ± 0.0541 | −0.0431 ± 0.0242 | −0.1225 ± 0.0254 |
| $IOP_i$ | 0.00091 ± 0.00029 | 0.0232 ± 0.0011 | −0.048 ± 0.0012 | −0.0032 ± 0.00054 | −0.0000195 ± 0.00056* |
| ICP | −0.0115 ± 0.00052 | 0.0181 ± 0.0020 | 0.0031 ± 0.0022* | 0.01795 ± 0.00097 | −0.00682 ± 0.001 |
| $V_{Dist} \cdot IOP_i$ | 0.0071 ± 0.0036 | −0.0083 ± 0.0014* | 0.0395 ± 0.0015 | 0.00156 ± 0.00067* | 0.001−± 0.0007* |
| $V_{Dist} \cdot ICP$ | 0.0076 ± 0.00041 | −0.0026 ± 0.0016* | 0.0271 ± 0.00173 | −0.00092 ± 0.00077* | −0.00184 ± 0.00081 |
| $IOP_i \cdot ICP$ | 0.000094 ± 0.0000093 | −0.00023 ± 0.00036 | 0.0011 ± 0.00004 | −0.000013 ± 0.000018* | −0.00012 ± 0.000018 |
| $V_{Dist} \cdot IOP_i \cdot ICP$ | −0.00016 ± 0.000011 | 0.00019 ± 0.000041 | −0.0011 ± 0.000045 | 0.000023 ± 0.00002* | 0.000088 ± 0.000021 |

Discussion

Figure 22:
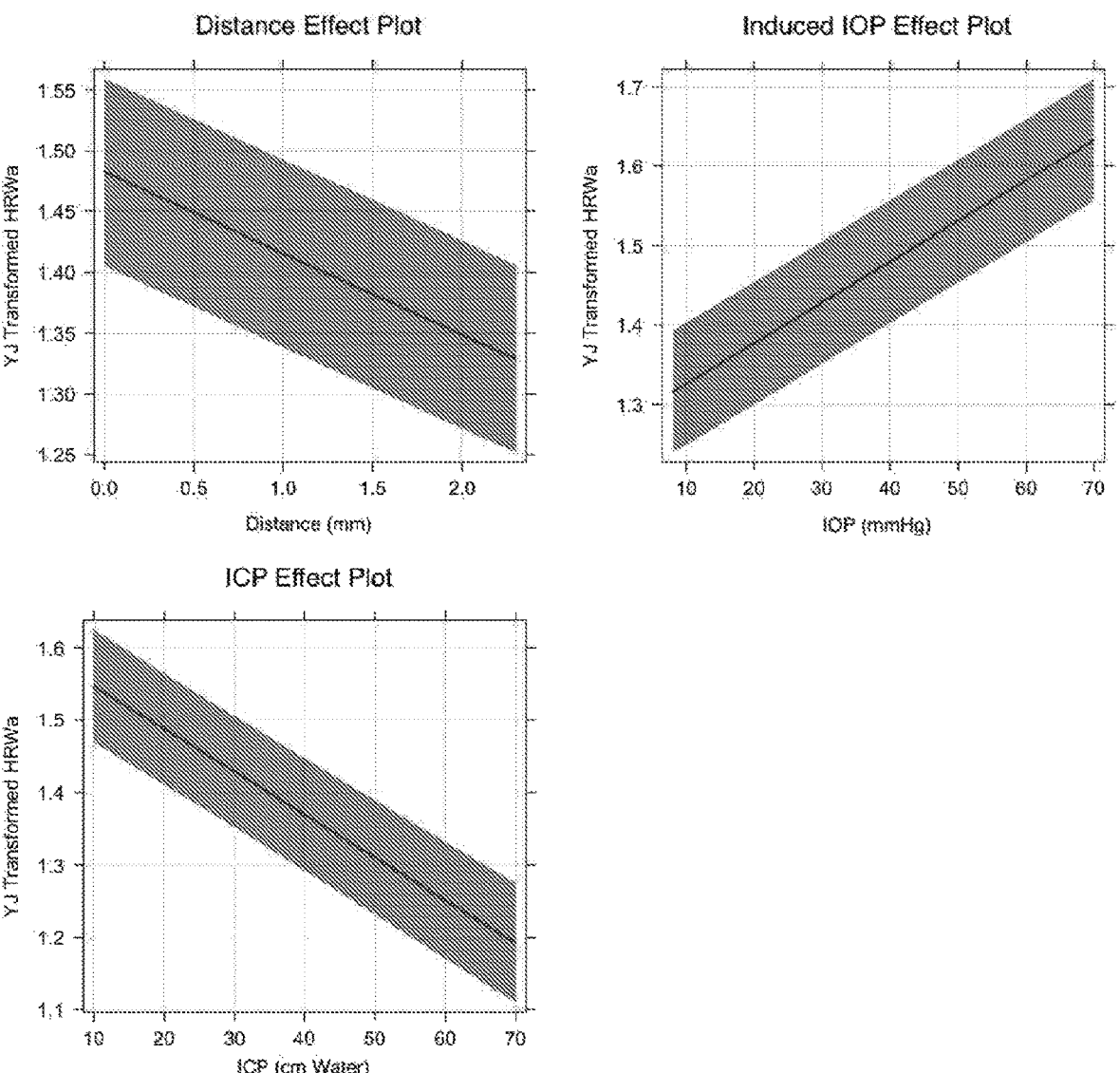
FIG. 22 shows Effect plots of the retinal venous harmonic regression waveform amplitude ($HRW_a$).
Figure 23:
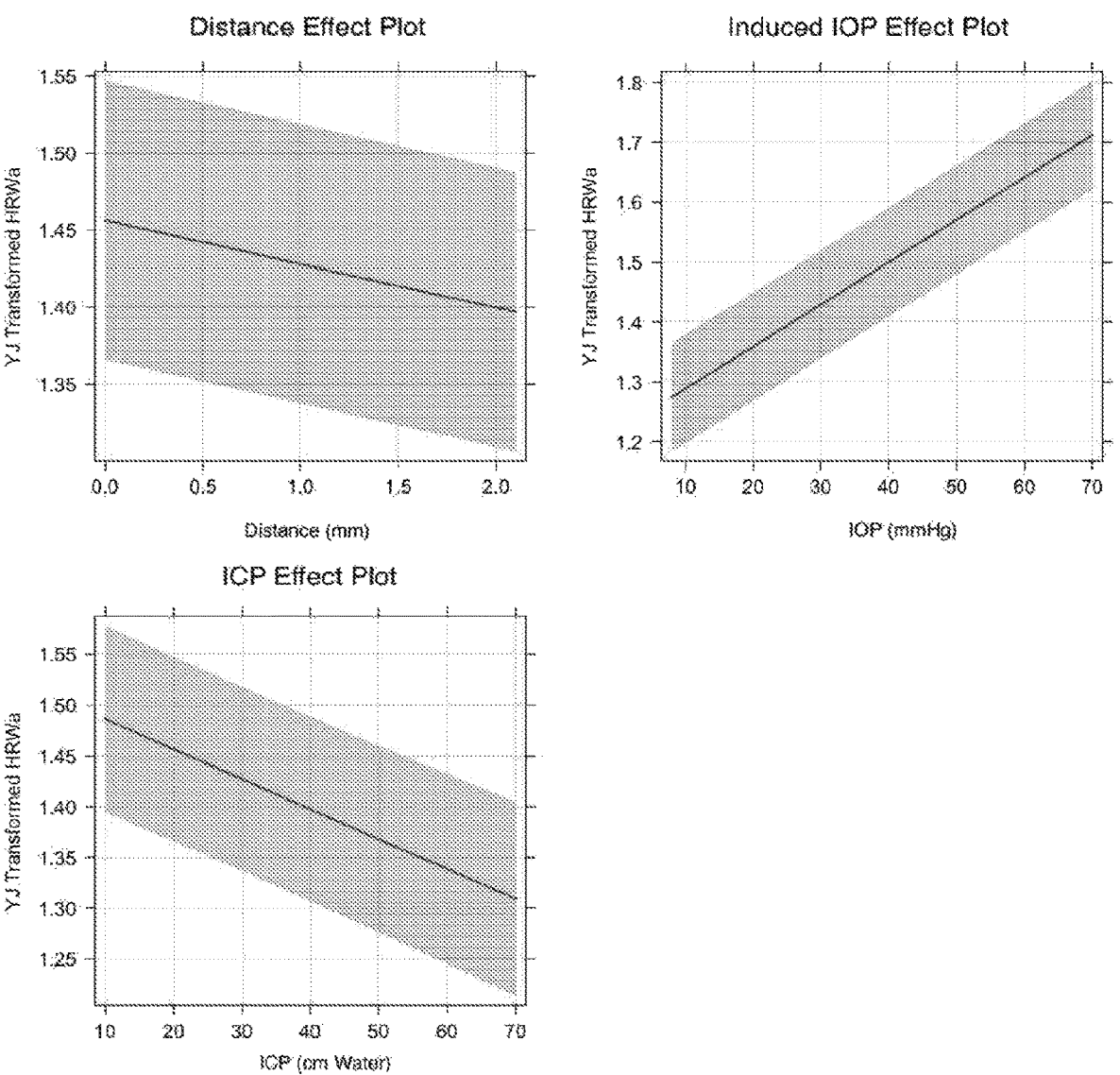
FIG. 23 shows Effect plots of the retinal arterial harmonic regression waveform amplitude ($HRW_a$).

The Applicant quantified the difference in both retinal venous and arterial pulse amplitudes between subjects with high and normal intracranial pressures over a dynamic range of induced intraocular pressures (Table 11). The most significant findings were the reduction in the mean venous and the increase in the mean arterial $HRW_{a-y,t}$ in the $ICP_h$ group (FIG. 24). Additionally, there was a normalization of the distribution of the non-transformed first Fourier harmonic coefficients in the retinal venous system, especially the $a_{n1}$ coefficient with high ICP (Table 9), interestingly ICP did not influence the median value of this coefficient between the two study groups (Table 10). In addition, the interaction plots comparing the main effects (ICP, vessel type) between the two study groups has allowed for a supposition of the origins of the Fourier coefficient components (FIG. 24), where the cosine ($a_{n1,2}$) is likely the mediator of the effects of $IOP_t$, and the sine coefficient ($b_{n1,2}$) is likely the mediator of ICP wave on the retinal vessel walls. the Applicant quantified the linear components of the interactions between the predictors assuming the simplest mathematical interrelationship. Also, it appears that currently available non-invasive methods of which the Applicant is aware are either not sufficiently accurate, reliable, or robust enough for widespread clinical adoption or require additional independent validation, in spite of the reported high linear correlation between the tested variables and ICP. In the current invention, both the fixed effects and the random factors in the mixed-effects models accounted for approximately 40% and the predictors accounted for less than 10% of the variance in the study population. Although the linear models' coefficients achieved a high level of statistical significance the variance between individuals (heteroscedasticity) in the vascular pulsation amplitudes. The limited explanatory power of a linear model explained may limit the practicality of linear models to estimate CSF non-invasively. Loss of spontaneous venous pulsation is a recognized categorical sign of increased ICP. FIG. 22 quantifies this decay in retinal venous pulsation amplitude with both $V_{Dist}$ and ICP, which were both greater than that detected in the retinal arterial system in FIG. 26. These differences are due to the higher venous vessel wall distensibility and compliance compared to that of retinal arteries. Vascular distensibility (change in cross-sectional area for a change in pressure) and compliance (change in volume for a change in pressure) both have non-linear dimension-pressure responses. From the previous work, the distensibility is known to follow a non-linear function in the larger veins, where the tension of the vessel wall is inversely related to vessel wall compliance and distensibility. Compliance of a vessel segment varies with vessel wall viscoelasticity and tension in the wall of the blood vessel per unit length (T); expressed through Laplace's law. In this equation the relationship between the tension in the wall of the blood vessel (T), is directly related to the product of the radius of the blood vessel (r) and transmural pressure ($P_{tm}$): $T=P_m \cdot r$.

In previous work, the Applicant quantified the decay in pulsation amplitude in the retinal blood vessels from a sample of normal subjects and reported that the coefficient of decay in venous pulsation amplitude is twice that of the arterial. The Applicant's results from a different population demonstrated a similar arterio-venous attenuation ratio of 1:2, which indicated a higher attenuation of the pulsation amplitude in the retinal veins compared to the retinal arteries likely because of the higher vessel wall viscoelasticity in the former.

To summarise, the retinal vascular changes are a consequence of a complex interaction between the retinal hemodynamics (retinal vascular flow rate, retinal intravascular pressure and the retinal arterio-venous (A/V) ratio, IOP, ICP, and systemic hemodynamics, resulting in an increase in intravascular pressure in the retinal vascular system. With increased ICP the retinal veins show a reduction in pulsation amplitude likely because of reduced vessel wall viscoelasticity and venous distension, whereas the retinal arteries demonstrate an increase in pulsatile amplitude likely as a consequence of increase mean arterial pressure, cerebral vasodilation, and alteration in the CSF pulsatile characteristics. The independent IOP and ICP pressure waves although driven by the cardiac cycle are modified by specific anatomic and physiological factors, therefore the wave effect on the vessel wall would likely to be mediated by separate Fourier coefficients.

CONCLUSION

The retinal vascular pulsation characteristics in the $ICP_h$ group showed high retinal arterial and low venous pulsation amplitudes. The interaction between retinal vascular pulsation measured using modified photoplethysmography over a dynamic range of intraocular pressures suggested that the Fourier sine coefficient $b_{n1,2}$ is likely a mediator of the retinal vascular response to ICP. Although a family of regression lines showed high linear characteristics, the low explanatory power of the predictors because of the high variability of retinal vascular pulsations between individuals limited the linear model as a predictor of cerebrospinal fluid pressure in the assessed population.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of determining accuracy of a non-invasive determination of intracranial pressure, comprising:

applying at least one selected controlled force to an eye of a subject;

taking a first plurality of measurements associated with retinal arterial pulsation amplitude data taken from the eye of the subject at the at least one selected controlled force, wherein the retinal arterial pulsation amplitude data is taken as a retinal arterial pulsation amplitude time-varying signal at multiple locations of a segment of an artery in the eye of the subject and the first plurality of measurements are obtained by decomposing the retinal arterial pulsation amplitude time varying signal into at least two frequency components for each of the multiple locations of the segment of the artery in the eye of the subject, and form a first data basis comprising at least information associated with the at least two frequency components of the first plurality of measurements;

taking a second plurality of measurements associated with retinal venous pulsation amplitude data taken from the eye of the subject at the at least one selected controlled force, wherein the retinal venous pulsation amplitude data taken as a retinal venous pulsation amplitude time-varying signal at multiple locations of a segment of a vein in the eye of the subject and the second plurality of measurements are obtained by decomposing the retinal venous pulsation amplitude time varying signal into at least two frequency components for each of the multiple locations of the segment of the vein in the eye of the subject, and forming a second data basis comprising at least information associated with the at least two frequency components of the second plurality of measurements;

determining each intracranial pressure of a first plurality of determined intracranial pressures from the retinal arterial pulsation amplitude data by a first trained model which has been trained to define a relationship between the intracranial pressure and primarily arterial venous pulsation data of the first data basis;

determining each intracranial pressure of a second plurality of determined intracranial pressures from the retinal venous pulsation amplitude data by a second trained model which has been trained to define a relationship between the intracranial pressure and primarily retinal venous pulsation data of the second data basis; and determining the accuracy of the intracranial pressure by comparing the first and second pluralities of intracranial pressures.

2. The method according to claim 1, comprising:

comparing the first and second pluralities of intracranial pressure using a mode of central tendency.

3. The method according to claim 1, comprising:

comparing peak densities of the first and second pluralities of determined intracranial pressures.

4. The method according to claim 1, wherein, prior to applying the first trained model or the second trained model, the method further comprises:

retrieving a training data set for the first trained model or the second trained model; and executing a model learning process to train the first trained model or the second trained model based on the training data set to define the relationship between the intracranial pressure and the first data basis or the second data basis.

5. The method according to claim 1, wherein each of the at least two frequency components is a harmonic of the retinal arterial pulsation amplitude data.

6. The method according to claim 1 wherein decomposition with respect to frequency includes the at least two frequency components that are harmonics of a Fourier series expansion and the Fourier series expansion has first and second harmonics as follows:

$$\mathcal{F}\left(f(t)_p\right) = a_0 + \sum_{n=1}^{\infty} a_n \cdot \cos(n\pi t) + b_n \cdot \sin(n\pi t)$$

wherein $f(t)_p$=the periodic component of the time series, $a_0$=coefficient representing the mean of $f(t)_p$, $a_n$=coefficient of the cosine function of $f(t)_p$, $b_n$=coefficient of the sine function of $f(t)_p$ and n=integer 0, 1, 2 . . . etc representing the harmonic component.

7. The method according to claim 1, wherein the first data basis and/or the second data basis includes:

retinal vascular pulsation amplitude data as a function of different distances relative to a center of an optic nerve of the eye of the subject.

8. The method according to claim 1, further comprising imaging retinal vascular pulsation of the eye of the subject over at least three cardiac cycles.

9. The method according to claim 1, comprising imaging retinal vascular pulsation of the eye of the subject using an ophthalmodynamometer force (ODF) device for applying the selected force to the eye of the subject, and further comprising imaging retinal vascular pulsation at a range of selected force (ODF) values to obtain a range of induced intraocular pressures.

10. The method according to claim 4, wherein the model learning process is a decision tree regression model learning process.

11. The method according to claim 6, wherein the Fourier series expansion comprises third and/or higher order harmonics.

12. One or more non-transitory computer readable media comprising computer readable program instructions embodied therein, the computer readable program instructions comprising a set of instructions that, when executed by at least one processor, cause the at least one processor to:

in connection with at least one selected controlled force applied to an eye of a subject, process a first plurality of measurements associated with retinal arterial pulsation amplitude data taken from the eye of the subject at the at least one selected controlled force, wherein the retinal arterial pulsation amplitude data is taken as a retinal arterial pulsation amplitude time-varying signal at multiple locations of a segment of an artery in the eye of the subject and the first plurality of measurements are obtained by decomposing the retinal arterial pulsation amplitude time varying signal into at least two frequency components for each of the multiple locations of the segment of the artery in the eye of the subject, and form a first data basis comprising at least information associated with the at least two frequency components of the first plurality of measurements;

process a second plurality of measurements associated with retinal venous pulsation amplitude data taken from the eye of the subject at the at least one selected controlled force, wherein the retinal venous pulsation amplitude data taken as a retinal venous pulsation amplitude time-varying signal at multiple locations of a segment of a vein in the eye of the subject and the second plurality of measurements are obtained by decomposing the retinal venous pulsation amplitude time varying signal into at least two frequency components for each of the multiple locations of the segment of the vein in the eye of the subject, and forming a second data basis comprising at least information associated with the at least two frequency components of the second plurality of measurements;

determine each intracranial pressure of a first plurality of determined intracranial pressures from the retinal arterial pulsation amplitude data by a first trained model which has been trained to define a relationship between the intracranial pressure and primarily arterial venous pulsation data of the first data basis;

determine each intracranial pressure of a second plurality of determined intracranial pressures from the retinal venous pulsation amplitude data by a second trained model which has been trained to define a relationship between the intracranial pressure and primarily retinal venous pulsation data of the second data basis; and determine the accuracy of the intracranial pressure by comparing the first and second pluralities of intracranial pressures.

13. The computer readable media according to claim 12, wherein the first trained model or the second trained model has been trained using a training data set that comprises one or more values of the following: induced intraocular pressure ($IOP_i$), at least one coefficient of the at least two frequency components, harmonic regression waveform amplitude data ($HRW_a$) information on laterality location of the recorded segment of artery or vein of the eye of the subject, information on the hemiretina location of the recorded segment of artery or vein of the eye, location of the recorded segment of the artery or vein of the eye of the subject measured intracranial pressure, and distance of the recorded segment of the artery or vein of the subject from the central optic nerve.

14. The computer readable media of claim 12, wherein the first data basis and/or second data basis includes:

at least one coefficient associated with the at least two frequency components.

15. The computer readable media of claim 12, wherein the first data basis and/or second data basis includes:

one or more measured intracranial pressure of the subject.

16. The method according to claim 12, wherein the first data basis and/or second data basis includes:

a measured intraocular pressure of the eye of the subject, or induced intraocular pressure of the eye of the subject calculated from at least one selected controlled force applied to the eye of the subject.

17. The computer readable media of claim 12, wherein the first data basis and/or second data basis includes:

harmonic regression waveform amplitude data, $HRW_A$, which is defined as the combination of the coefficients $a_{n,1}$, $a_{n,2}$ $b_{n,1}$ and $b_{n,2}$ of the at least two frequency components.

18. The computer readable media of claim 12, wherein the first data basis and/or second data basis includes:

waveform amplitude data which is based on a combination of one or more of the coefficients $a_{n,1}$, $a_{n,2}$ $b_{n,1}$ and $b_{n,2}$ of the at least two frequency components.

19. The computer readable media of claim 12, wherein the first data basis and/or second data basis includes:

retinal vascular pulsation amplitude data as a function of different distances relative to a center of an optic nerve of the eye of the subject.

20. The computer readable media of claim 12, wherein the first data basis and/or second data basis includes:

distance relative to a center of an optic nerve of the eye of the subject of the recorded segment of the artery or vein of the eye of the subject.

21. The computer readable media of claim 12, wherein the first data basis and/or second data basis includes:

multiple retinal vascular pulsation amplitude data as a function of different distances relative to a center of an optic nerve of the eye of the subject of the recorded segment of the artery or vein of the eye of the subject.

22. The computer readable media of claim 12, wherein the first data basis and/or second data basis includes:

information on a laterality location of the recorded segment of the artery or vein of the eye of the subject.

\* \* \* \* \*